US011939584B2

(12) United States Patent
Zhao et al.

(10) Patent No.: US 11,939,584 B2
(45) **Date of Patent: *Mar. 26, 2024**

(54) METHODS AND MICROORGANISMS FOR MAKING 2,3-BUTANEDIOL AND DERIVATIVES THEREOF FROM C1 CARBONS

(71) Applicant: PRECIGEN, INC., Germantown, MD (US)

(72) Inventors: Xinhua Zhao, Dublin, CA (US); Mark Anton Held, Emeryville, CA (US); Tina Huynh, Oakland, CA (US); Lily Yuin Chao, San Francisco, CA (US); Na Trinh, Walnut Creek, CA (US); Matthias Helmut Schmalisch, South San Francisco, CA (US); Bryan Yeh, Walnut Creek, CA (US); James Kealey, Sebastopol, CA (US); Kevin Lee Dietzel, Pacifica, CA (US)

(73) Assignee: PRECIGEN, INC., Germantown, MD (US)

( * ) Notice: Subject to any disclaimer, the term of this patent is extended or adjusted under 35 U.S.C. 154(b) by 53 days.

This patent is subject to a terminal disclaimer.

(21) Appl. No.: 17/444,188

(22) Filed: Jul. 31, 2021

(65) Prior Publication Data

US 2022/0049259 A1 Feb. 17, 2022

Related U.S. Application Data

(62) Division of application No. 16/481,799, filed as application No. PCT/US2018/015909 on Jan. 30, 2018, now Pat. No. 11,111,496.

(60) Provisional application No. 62/588,985, filed on Nov. 21, 2017, provisional application No. 62/512,312, filed on May 30, 2017, provisional application No. 62/504,626, filed on May 11, 2017, provisional application No. 62/451,819, filed on Jan. 30, 2017.

(51) Int. Cl.

| | |
|---|---|
| ***C12N 15/52*** | (2006.01) |
| ***C12N 1/20*** | (2006.01) |
| ***C12N 9/04*** | (2006.01) |
| ***C12N 9/10*** | (2006.01) |
| ***C12N 9/88*** | (2006.01) |
| ***C12N 15/74*** | (2006.01) |
| ***C12P 5/02*** | (2006.01) |
| ***C12P 7/16*** | (2006.01) |
| ***C12P 7/18*** | (2006.01) |

(52) U.S. Cl.

CPC ............... *C12N 15/52* (2013.01); *C12N 1/20* (2013.01); *C12N 9/0006* (2013.01); *C12N 9/1022* (2013.01); *C12N 9/88* (2013.01); *C12N 15/74* (2013.01); *C12P 5/023* (2013.01); *C12P 7/16* (2013.01); *C12P 7/18* (2013.01); *C12Y 101/01304* (2013.01); *C12Y 202/01006* (2013.01); *C12Y 401/01004* (2013.01); *C12Y 401/01005* (2013.01)

(58) Field of Classification Search

CPC ..................................................... C12N 15/52

See application file for complete search history.

(56) References Cited

U.S. PATENT DOCUMENTS

| | | | |
|---|---|---|---|
| 2007/0259410 | A1 | 11/2007 | Donaldson et al. |
| 2007/0292927 | A1 | 12/2007 | Donaldson et al. |
| 2008/0014619 | A1 | 1/2008 | Huang et al. |
| 2011/0008861 | A1 | 1/2011 | Berry et al. |
| 2011/0086407 | A1 | 4/2011 | Berka et al. |
| 2014/0273128 | A1 | 9/2014 | Coleman et al. |
| 2016/0160223 | A1 | 6/2016 | Koepke et al. |

FOREIGN PATENT DOCUMENTS

| | | | | |
|---|---|---|---|---|
| WO | 2013102147 | A2 | | 7/2013 |
| WO | 2014092562 | | | 6/2014 |
| WO | WO 2015/195972 | | * | 12/2015 |
| WO | 2018/131898 | | | 7/2018 |
| WO | 2018/200894 | | | 11/2018 |

OTHER PUBLICATIONS

Kim, S. & Hahn, J-S., "Efficient production of 2,3-butanediol in *Saccharomyces cerevisiae* by eliminating ethanol and glycerol production and redox rebalancing", Metabolic Engineering, 2015, vol. 31, pp. 94-101.*

Zhang et al., Green Chem. (2012), 14:3441-3450.

Hu et al., China Biotechnology (2016), 36: 57-64 (Translation of Abstract).

Zhang et al., Green Chemistry, 14:3441-3450 (2012).

EC 4.1.1.5—Acetolactate Decarboxylase, IntEz, 2015.

International Search Report issued in PCT/US2018/015909.

Written Opinion of the ISA issued in PCT/US2018/015909.

Kopke et al., Applied and Environmental Microbiology, 77:5467-5475 (2011).

Campbell et al., Cell Calcium, 41:97-106 (2006).

Cui et al., Journal of Applies Microbiology, 117:690-698 (2014).

Nguyen et al., Metab Eng (2018), 47:323-333.

Vecherskaya et al., Environmental Microbiology Reports (2009), 1: 442-449.

* cited by examiner

*Primary Examiner* — Suzanne M Noakes

(74) *Attorney, Agent, or Firm* — Gene J. Yao; Barnes & Thornburg LLP

(57) ABSTRACT

Genetically modified microorganisms that have the ability to convert carbon substrates into chemical products such as 2,3-BDO are disclosed. For example, genetically modified methanotrophs that are capable of generating 2,3-BDO at high titers from a methane source are disclosed. Methods of making these genetically modified microorganisms and methods of using them are also disclosed.

15 Claims, 17 Drawing Sheets

Specification includes a Sequence Listing.

Expression Cassette for XZ58 (SEQ ID. NO: 15)

AAGAAACCAATTGTCCATATTGCATCAGACATTGCCGTCACTGCGTCTTTTACTGGCTCTTCTCGCTAACCAAACCGGTAACCCCGCTTATTAAAAGCATTCTGTAACAAAGCG
GGACCAAAGCCATGACAAAAACGCGTAACAAAAGTGTCTATAATCACGGCAGAAAAGTCCACATTGATTATTTGCACGGCGTCACACTTTGCTATGCCATAGCATTTTTATCC
ATAAGATTAGCGGATCCTACCTGACGCTTTTTATCGCAACTCTCTACTGTTTCTCCATACCCGTTTTTTTGGGCTAACAGGAGGAATTAACCATGaccaaggccaccaaggaacagaa
aagcctggtcaagaaccgcggtgctgaactggttgtggactgcctcgtggaacagggcgtgacccatgtcttcggcatcccgggcgccaagatcgacgccgtcttcgacgccctgcaggataaaggtccggaaatcatcgtggc
acgccatgagcagaacgcagccttcatggcccaggccgtcggtcggctgacgggtaagcccggcgtggtgctggtcacctccggtccgggagcctcgaacctggccacggactgctcaccgccaacaccgaaggcgacccg
gtggtcgccctggccggtaatgtcatccgggcggatcgcctgaagcgcacccatcagtccctggataacgcggccctgttccagccaatcaccaaatatagtgtcgaagtgcaggatgtgaagaacatcccggaagccgtcacc
aatgcgttccgaatcgcgtccgccggccaagcaggggcagcattcgtgagcttcccccaggacgtggtcaatgaagtgaccaacaccaaaaacgtcagagccgtagccgccccgaagctgggccctgcagcagatgacgcca
tctccgctgccatcgcgaagatccagaccgcaaagctgccggtcgtgctggtcggaatgaagggcggacgcccggaggccatcaaggccgtgcgtaaactgctgaagaaggtgcagctaccgttcgtggaaacctaccaggcc
gccggcaccctgagtcgggacttggaagaccagtatttcggccgtatcggcctgttccgcaaccagccgggcgacctgctcctggaacaagccgatgtggtgctgaccatcggctacgacccgatcgaatatgacccgaagttct
ggaacatcaatggcgaccgcacgatcatccatctggacgaaatcatcgccgacatcgaccatgcctatcagccggacctggaactgatcggcgacatcccgagcaccatcaaccacatcgaacacgatgccgtgaaggtggaa
tttgccgaacgcgaacagaagatcctgtcggacctgaagcagtatatgcatgagggcgaacaggtgcctgccgactggaagtcggacagagcccatccgctggaaatcgtgaaggaactgcgtaacgccgtcgacgaccatg
tcaccgtcacctgcgatatcggcagccatgccatttggatgagccgctacttccggagctatgaaccgctgaccctgatgatctccaacggtatgcagaccctcggcgtcgccctcccgtgggccatcggcgcaagtctggtgaa
gccgggcgaaaaagtggtcagcgtgtccggcgacggcggcttcctgttctccgctatggaactggaaaccgcggtccgcctgaaggccccgatcgtgcatatcgtgtggaacgacagcacctacgacatggtcgccttccagca
gctgaaaaagtacaaccgcaccagcgccgtggacttcggcaatatcgacatcgtgaagtatgccgaatccttcggagccaccggactgcgcgtggaatccccggaccagctggcggacgttctgcgtcagggcatgaatgccg
aaggtcccgtgattatcgatgtgcccgtcgactacagcgacaacatcaacctggcctcggacaaattgccgaaggagttcggcgaactgatgaaaacaaaagcactaTAAAAAGGAGGTACGTATGaaccactcggc
cgaatgcacctgcgaagagagcctctgcgaaaccctccgggccttctcggcccagcacccggagagcgtcctgtaccagacgagcctgatgtcggcgctgctgtcgggcgtgtatgaaggctcgacgaccatcgccgac
ctgctgaagcatggcgacttcggcctgggcaccttcaatgaactggacggcgagctcatcgccttcagctcgcaggtgtatcagctccgggccgatggctccgcccggaaggcccagcccgaacagaagaccccgttcg
ccgtgatgacctggttccagccgcagtatcggaagaccttcgaccaccccgtgagccgccagcagctccacgaggtgatcgaccagcagatcccgagcgacaacctcttctgcgccctgcgcatcgacggccatttccgcc
acgcgcatacccgcaccgtcccgcggcagaccccgccctaccgcgccatgaccgatgtcctggatgaccagccggtcttccggttcaaccagcgcgagggcgtcctggtcggcttccgcaccccgcagcacatgcagggc
atcaacgtcgcgggctatcatgaacacttcatcaccgatgatcgcaagggcggcggccacctcctcgactaccagctggaccacggcgtcctgaccttcggcgaaatccataagctgatgatcgacctccccgccgacag
cgccttcctgcaggcgaatctgcatccggacaacctcgatgccgccatccgctccgtcgagtcgTGATTTCAGCCTGATACAGATTAAATCAGAACGCAGAAGCGGTCTGATAAAACAGAATTTGC
CTGGCGGCAGTAGCGCGGTGGTCCCACCTGACCCCATGCCGAACTCAGAAGTGAAACGCCGTAGCGCCGATGGTAGTGTGGGGTCTCCCCATGCGAGAGTAGGGAACTGC
CAGGCATCAAATAAAACGAAAGGCTCAGTCGAAAGACTGGGCCTTTCGTTTTATCTGTTGTTTGTCGGTGAACGCTCTCCTGAGTAGGACAAATCCGCCGGGAGCGGATTTG
AACGTTGCGAAGCAACGGCCCGGAGGGTGGCGGGCAGGACGCCCGCCATAAACTGCCAGGCATCAAATTAAGCAGAAGGCCATCCTGACGGATGGCCTTTTTGCGTTTCTG
AGGTTCAGGCGAAACCGCAGACTCAAGGGCGCTTGCTCCCGGGAAAGATCGTATTAGTTTGCCTCGATCGGCGGTCCTTGTGACAGGGAGATATTCCCGACGGATCCGGGG
CATTCGAGCGGAACCGCCCGCCGTGGGAGTTTTTCCAGCGAGCATTCGAGAGTTTTTCAAGGCGGCTTCGAGGGGTTATTCCGTAACGCCGCCGACATGATCTGTCCCAGAAT
CTCCGCCGCTGTTCGTAGAGCGCCGATGCAGGGTCGGCATCAATCATTCTTGGAGGAGACACATGaaggccgtcctgtggtacgacaaaaaggatgtccgcgtggaagaaatcgaggaac
cgaaggtgaaagaaaacgccgtgaagatcaaagtcaagtggtgcggcatctgcggctcggacctgcatgagtatctcggcggcccgatcttcatcccggtcggcacccccacccgctgtcgaagagcaccgcgcc
cgtcgtgctgggccacgagttctcgggcgaagtggtggagatcggcagcaaagtgaccaagttcaaggcgggcgaccgcgtcatcgtggaaccgatcgtcgcctgcggcaaatgcccggcctgcctggaaggca
agtacaatctgtgcgaggcgctgggcttccacggcctgtgcggcagcggcggcggcttcgccgagtacacggtgttcccggaagatttcgtgcacaagatccccgacacgatggattatgaacaggccgcgctggt
ggagccgatggcggtcgcgctgcactccctgcgggtgggcaacttcaccacgggcaacaccgccctggtcctgggcgcgggcccgatcggcctggccaccatccagtgcctcaaagcgtcgggcgcccggatcgtca
tcgtcttccagcgcaaatcggtgcggcaggaatacgccaagaagttcggcgcggacgtggtcctcgacccgaatgaggtggacgtgatcgaggaaatcaaaaagctgaccggcggcgtgggcgtggacacgag
cttcgaaaccaccggcgccaacgtcggcatcaacaccgcgatccaggcgctgaaatatgagggcaccgccgtcatcacctccgtctgggagaagaacgccgagatcaatccgaacgacctggtcttcaccgaaaa
gaaggtcgtcggcaccctcgcgtaccggcacgagttcccgtcgaccatcgccctgatgaacgacggccgcatcaagaccgatggctatatcaccaagcggatcgccctggaagacatcgtcaaggagggcttcga
aaccctgaccggcccggagaagaaaaagcacgtcaaaatcatcgtcacgcccgataaagcctcctgTGAGACTCCTGTTGATAGATCCAGTAATGACCTCAGAACTCCATCTGGATTTGTTCA
GAACGCTCGGTTGCCGCCGGGCGTTTTTATTGGTGAGAATC

FIG. 3

Expression Cassette for XZ59 (SEQ ID. NO: 16)

AAGAAACCAATTGTCCATATTGCATCAGACATTGCCGTCACTGCGTCTTTTACTGGCTCTTCTCGCTAACCAAACCGGTAACCCCGCTTATTAAAAGCATTCTGTAACAAAGCG
GGACCAAAGCCATGACAAAAACGCGTAACAAAAGTGTCTATAATCACGGCAGAAAAGTCCACATTGATTATTTGCACGGCGTCACACTTTGCTATGCCATAGCATTTTTATCC
ATAAGATTAGCGGATCCTACCTGACGCTTTTTATCGCAACTCTCTACTGTTTCTCCATACCCGTTTTTTTGGGCTAACAGGAGGAATTAACCATGaccaaggccaccaaggaacagaa
aagcctggtcaagaaccgcggtgctgaactggttgtggactgcctcgtggaacagggcgtgacccatgtcttcggcatcccgggcgccaagatcgacgccgtcttcgacgccctgcaggataaaggtccggaaatcatcgtggc
acgccatgagcagaacgcagccttcatggcccaggccgtcggtcggctgacgggtaagcccggcgtggtgctggtcacctccggtccgggagcctcgaacctggccacgggactgctcaccgccaacaccgaaggcgacccg
gtggtcgccctggccggtaatgtcatccgggcggatcgcctgaagcgcacccatcagtccctggataacgcggccctgttccagccaatcaccaaatatagtgtcgaagtgcaggatgtgaagaacatcccggaagccgtcacc
aatgcgttccgaatcgcgtccgccggccaagcaggggcagcattcgtgagcttcccccaggacgtggtcaatgaagtgaccaacaccaaaaacgtcagagccgtagccgccccgaagctgggccctgcagcagatgacgcca
tctccgctgccatcgcgaagatccagaccgcaaagctgccggtcgtgctggtcggaatgaagggcggacgcccggaggccatcaaggccgtgcgtaaactgctgaagaaggtgcagctaccgttcgtggaaacctaccaggcc
gccggcaccctgagtcgggacttggaagaccagtatttcggccgtatcggcctgttccgcaaccagccgggcgacctgctcctggaacaagccgatgtggtgctgaccatcggctacgacccgatcgaatatgacccgaagttct
ggaacatcaatggcgaccgcacgatcatccatctggacgaaatcatcgccgacatcgaccatgcctatcagccggacctggaactgatcggcgacatcccgagcaccatcaaccacatcgaacacgatgccgtgaaggtggaa
tttgccgaacgcgaacagaagatcctgtcggacctgaagcagtatatgcatgagggcgaacaggtgcctgccgactggaagtcggacagagcccatccgctggaaatcgtgaaggaactgcgtaacgccgtcgacgaccatg
tcaccgtcacctgcgatatcggcagccatgccatttggatgagccgctacttccggagctatgaaccgctgaccctgatgatctccaacggtatgcagaccctcggcgtcgccctcccgtgggccatcggcgcaagtctggtgaa
gccgggcgaaaaagtggtcagcgtgtccggcgacggcggcttcctgttctccgctatggaactggaaaccgcggtccgcctgaaggccccgatcgtgcatatcgtgtggaacgacagcacctacgacatggtcgccttccagca
gctgaaaaagtacaaccgcaccagcgccgtggacttcggcaatatcgacatcgtgaagtatgccgaatccttcggagccaccggactgcgcgtggaatccccggaccagctggcggacgttctgcgtcagggcatgaatgccg
aaggtcccgtgattatcgatgtgcccgtcgactacagcgacaacatcaacctggcctcggacaaattgccgaaggagttcggcgaactgatgaaaacaaaagcactaTAAAAAGGAGGTACGTATGaaccactcggc
cgaatgcacctgcgaagagagcctctgcgaaaccctccgggccttctcggcccagcacccggagagcgtcctgtaccagacgagcctgatgtcggcgctgctgtcgggcgtgtatgaaggctcgacgaccatcgccgac
ctgctgaagcatggcgacttcggcctgggcaccttcaatgaactggacggcgagctcatcgccttcagctcgcaggtgtatcagctccgggccgatggctccgcccggaaggcccagcccgaacagaagaccccgttcg
ccgtgatgacctggttccagccgcagtatcggaagaccttcgaccaccccgtgagccgccagcagctccacgaggtgatcgaccagcagatcccgagcgacaacctcttctgcgccctgcgcatcgacggccatttccgcc
acgcgcatacccgcaccgtcccgcggcagaccccgccctaccgcgccatgaccgatgtcctggatgaccagccggtcttccggttcaaccagcgcgagggcgtcctggtcggcttccgcaccccgcagcacatgcagggc
atcaacgtcgcgggctatcatgaacacttcatcaccgatgatcgcaagggcggcggccacctcctcgactaccagctggaccacggcgtcctgaccttcggcgaaatccataagctgatgatcgacctccccgccgacag
cgccttcctgcaggcgaatctgcatccggacaacctcgatgccgccatccgctccgtcgagtcgTGATTTCAGCCTGATACAGATTAAATCAGAACGCAGAAGCGGTCTGATAAAACAGAATTTGC
CTGGCGGCAGTAGCGCGGTGGTCCCACCTGACCCCATGCCGAACTCAGAAGTGAAACGCCGTAGCGCCGATGGTAGTGTGGGGTCTCCCCATGCGAGAGTAGGGAACTGC
CAGGCATCAAATAAAACGAAAGGCTCAGTCGAAAGACTGGGCCTTTCGTTTTATCTGTTGTTTGTCGGTGAACGCTCTCCTGAGTAGGACAAATCCGCCGGGAGCGGATTTG
AACGTTGCGAAGCAACGGCCCGGAGGGTGGCGGGCAGGACGCCCGCCATAAACTGCCAGGCATCAAATTAAGCAGAAGGCCATCCTGACGGATGGCCTTTTTGCGTTTCG
AGGTTCAGGCGAAACCGCAGACTCAAGGGCGCTTGCTCCCGGGAAAGATCGTATTAGTTTGCCTCGATCGGCGGTCCTTGTGACAGGGAGATATTCCCGACGGATCCGGGG
CATTCGAGCGGAACCGCCCGCCGTGGAGTTTTTCCAGCGAGCATTCGAGAGTTTTTCAAGGCGGCTTCGAGGGGTTATTCCGTAACGCCGCCGACATGATCTGTCCCAGAAT
CTCCGCCGCTGTTCGTAGAGCGCCGATGCAGGGTCGGCATCAATCATTCTTGGAGGAGACACATGaaagccctgctgtggcataaccagcgcgacgtgcgggtggaagaggtcccggagcc
cgccgtccgcagcggcgcggtgaaaatcaaagtgaaatggtgcggcatctgtggcaccgacctgcatgaatatctggccggccccatcttcatcccgacggaggaacatccgctgacgcacgtcaaggccccggtc
atcctcggccatgagttcagcggcgaggtggtggagatcggcgaaggcgtcaccaatcacaaagtcggcgatcgcgtggtcgtcgaaccgatctactcgtgcggcaagtgtgaggcgtgcaagcacggccactat
aatgtctgcgagcagctggtgttccacggcctgggcggcgacggcggcggcttctcggagtacaccgtggtgccggcggatatggtccaccacatcccggatgaaatgacctacgagcagggcgccctggtcgag
ccggccgccgtggcggtgcacgcggtgcgccagagcaaactcaaggagggcgaagccgtggccgtcttcggctgcggcccgatcggcctgctggtcatccaggcggccaaagcggcgggcgcgacccccgtcatc
gcggtcgagctgtcgaaggaacgccaggagctcgccaagctggcgggcgcggattatgtcctgaaccccgccgaacaggacgtggtggcggaaatccggaacctgaccaacggcctgggcgtcaacgtctccttc
gaggtcaccggcgtggaagtcgtcctgcggcaggcgatcgaatcgacctcgttcgagggccagacggtcatcgtgtcggtctgggagaaggacgccaccatcacgcccaataatctggtcctgaaagagaagga
agtggtcggcatcctcggctaccggcatatcttcccgtccgtcatcaagctgatctcgtcgggccagatccaggccgagaaactcatcaccaagaagatcacggtggaccaggtggtcgaagaaggcttcgaagcg
ctggtcaaggataagaagcaggtgaagatcctcgtgtcgccgaagTGAGACTCCTGTTGATAGATCCAGTAATGACCTCAGAACTCCATCTGGATTTGTTCAGAACGCTCGGTTGCCGCC
GGGCGTTTTTTATTGGTGAGAATC

FIG. 4

Expression Cassette for XZ06 (SEQ ID. NO: 17)

AAGAAACCAATTGTCCATATTGCATCAGACATTGCCGTCACTGCGTCTTTTACTGGCTCTTCTCGCTAACCAAACCGGTAACCCCGCTTATTAAAAGCATTCTGTAACAAAGCG
GGACCAAAGCCATGACAAAAACGCGTAACAAAAGTGTCTATAATCACGGCAGAAAAGTCCACATTGATTATTTGCACGGCGTCACACTTTGCTATGCCATAGCATTTTTATCC
ATAAGATTAGCGGATCCTACCTGACGCTTTTTATCGCAACTCTCTACTGTTTCTCCATACCCGTTTTTTTGGGCTAACAGGAGGAATTAACCATGaccaaggccaccaaggaacagaa
aagcctggtcaagaaccgcggtgctgaactggttgtggactgcctcgtggaacagggcgtgacccatgtcttcggcatcccgggcgccaagatcgacgccgtcttcgacgccctgcaggataaaggtccggaaatcatcgtggc
acgccatgagcagaacgcagccttcatggcccaggccgtcggtcggctgacgggtaagcccggcgtggtgctggtcacctccggtccgggagcctcgaacctggccacgggactgctcaccgccaacaccgaaggcgacccg
gtggtcgccctggccggtaatgtcatccgggcggatcgcctgaagcgcacccatcagtccctggataacgcggccctgttccagccaatcaccaaatatagtgtcgaagtgcaggatgtgaagaacatcccggaagccgtcacc
aatgcgttccgaatcgcgtccgccggccaagcaggggcagcattcgtgagcttcccccaggacgtggtcaatgaagtgaccaacaccaaaaacgtcagagccgtagccgccccgaagctgggccctgcagcagatgacgcca
tctccgctgccatcgcgaagatccagaccgcaaagctgccggtcgtgctggtcggaatgaagggcggacgcccggaggccatcaaggccgtgcgtaaactgctgaagaaggtgcagctaccgttcgtggaaacctaccaggcc
gccggcaccctgagtcgggacttggaagaccagtatttcggccgtatcggcctgttccgcaaccagccgggcgacctgctcctggaacaagccgatgtggtgctgaccatcggctacgacccgatcgaatatgacccgaagttct
ggaacatcaatggcgaccgcacgatcatccatctggacgaaatcatcgccgacatcgaccatgcctatcagccggacctggaactgatcggcgacatcccgagcaccatcaaccacatcgaacacgatgccgtgaaggtggaa
tttgccgaacgcgaacagaagatcctgtcggacctgaagcagtatatgcatgagggcgaacaggtgcctgccgactggaagtcggacagagcccatccgctggaaatcgtgaaggaactgcgtaacgccgtcgacgaccatg
tcaccgtcacctgcgatatcggcagccatgccatttggatgagccgctacttccggagctatgaaccgctgaccctgatgatctccaacggtatgcagaccctcggcgtcgccctcccgtgggccatcggcgcaagtctggtgaa
gccgggcgaaaaagtggtcagcgtgtccggcgacggcggcttcctgttctccgctatggaactggaaaccgcggtccgcctgaaggccccgatcgtgcatatcgtgtggaacgacagcacctacgacatggtcgccttccagca
gctgaaaaagtacaaccgcaccagcgccgtggacttcggcaatatcgacatcgtgaagtatgccgaatccttcggagccaccggactgcgcgtggaatccccggaccagctggcggacgttctgcgtcagggcatgaatgccg
aaggtcccgtgattatcgatgtgcccgtcgactacagcgacaacatcaacctggcctcggacaaattgccgaaggagttcggcgaactgatgaaaacaaaagcactaTAAAAGGAGGTACGTATGaaccactcggc
cgaatgcacctgcgaagagagcctctgcgaaaccctccgggccttctcggcccagcacccggagagcgtcctgtaccagacgagcctgatgtcggcgctgctgtcgggcgtgtatgaaggctcgacgaccatcgccgac
ctgctgaagcatggcgacttcggcctgggcaccttcaatgaactggacggcgagctcatcgccttcagctcgcaggtgtatcagctccgggccgatggctccgcccggaaggcccagcccgaacagaagaccccgttcg
ccgtgatgacctggttccagccgcagtatcggaagaccttcgaccaccccgtgagccgccagcagctccacgaggtgatcgaccagcagatcccgagcgacaacctcttctgcgccctgcgcatcgacggccatttccgcc
acgcgcatacccgcaccgtcccgcggcagaccccgccctaccgcgccatgaccgatgtcctggatgaccagccggtcttccggttcaaccagcgcgagggcgtcctggtcggcttccgcaccccgcagcacatgcagggc
atcaacgtcgcgggctatcatgaacacttcatcaccgatgatcgcaagggcggcggccacctcctcgactaccagctggaccacggcgtcctgaccttcggcgaaatccataagctgatgatcgacctccccgccgacag
cgccttcctgcaggcgaatctgcatccggacaacctcgatgccgccatccgctccgtcgagtcgTGAAAGGAGGTACGTATGaaggccgtcctgtggtacgacaaaaaggatgtccgcgtggaagaaatcg
aggaaccgaaggtgaaagaaaacgccgtgaagatcaaagtcaagtggtgcggcatctgcggctcggacctgcatgagtatctcggcggcccgatcttcatcccggtcggcacccccacccgctgtcgaagagca
ccgcgcccgtcgtgctgggccacgagttctcgggcgaagtggtggagatcggcagcaaagtgaccaagttcaaggcgggcgaccgcgtcatcgtggaaccgatcgtcgcctgcggcaaatgcccggcctgcctgg
aaggcaagtacaatctgtgcgaggcgctgggcttccacggcctgtgcggcagcggcggcggcttcgccgagtacacggtgttcccggaagatttcgtgcacaagatccccgacacgatggattatgaacaggccg
cgctggtggagccgatggcggtcgcgctgcactccctgcgggtgggcaacttcaccacgggcaacaccgccctggtcctgggcgcgggcccgatcggcctggccaccatccagtgcctcaaagcgtcgggcgcccgg
atcgtcatcgtcttccagcgcaaatcggtgcggcaggaatacgccaagaagttcggcgcggacgtggtcctcgacccgaatgaggtggacgtgatcgaggaaatcaaaaagctgaccggcggcgtgggcgtgg
acacgagcttcgaaaccaccggcgccaacgtcggcatcaacaccgcgatccaggcgctgaaatatgagggcaccgccgtcatcacctccgtctgggagaagaacgccgagatcaatccgaacgacctggtcttca
ccgaaaagaaggtcgtcggcaccctcgcgtaccggcacgagttcccgtcgaccatcgccctgatgaacgacggccgcatcaagaccgatggctatatcaccaagcggatcgccctggaagacatcgtcaaggagg
gcttcgaaaccctgaccggcccggagaagaaaaagcacgtcaaaatcatcgtcacgcccgataaaagcctcctgTGATTTCAGCCTGATACAGATTAAATCAGAACGCAGAAGCGGTCTGATAA
AACAGAATTTGCCTGGCGGCAGTAGCGCGGTGGTCCCACCTGACCCCATGCCGAACTCAGAAGTGAAACGCCGTAGCGCCGATGGTAGTGTGGGGTCTCCCCATGCGAGA
GTAGGGAACTGCCAGGCATCAAATAAAACGAAAGGCTCAGTCGAAAGACTGGGCCTTTCGTTTTATCTGTTGTTTGTCGGTGAACGCTCTCCTGAGTAGGACAAATCCGCCG
GGAGCGGATTTGAACGTTGCGAAGCAACGGCCCGGAGGGTGGCGGGCAGGACGCCCGCCATAAACTGCCAGGCATCAAATTAAGCAGAAGGCCATCCTGACGGATGGCCT
TTTTGCGTTTC

FIG. 5

Expression Cassette for XZ08 (SEQ ID. NO: 18)

AAGAAACCAATTGTCCATATTGCATCAGACATTGCCGTCACTGCGTCTTTTACTGGCTCTTCTCGCTAACCAAACCGGTAACCCCGCTTATTAAAAGCATTCTGTAACAAAGCG
GGACCAAAGCCATGACAAAAACGCGTAACAAAAGTGTCTATAATCACGGCAGAAAAGTCCACATTGATTATTTGCACGGCGTCACACTTTGCTATGCCATAGCATTTTTATCC
ATAAGATTAGCGGATCCTACCTGACGCTTTTTATCGCAACTCTCTACTGTTTCTCCATACCCGTTTTTTTGGGCTAACAGGAGGAATTAACCATGaccaaggccaccaaggaacagaa
aagcctggtcaagaaccgcggtgctgaactggttgtggactgcctcgtggaacagggcgtgacccatgtcttcggcatcccgggcgccaagatcgacgccgtcttcgacgccctgcaggataaaggtccggaaatcatcgtggc
acgccatgagcagaacgcagccttcatggcccaggccgtcggtcggctgacgggtaagcccggcgtggtgctggtcacctccggtccgggagcctcgaacctggccacgggactgctcaccgccaacaccgaaggcgacccg
gtggtcgccctggccggtaatgtcatccgggcggatcgcctgaagcgcacccatcagtccctggataacgcggccctgttccagccaatcaccaaatatagtgtcgaagtgcaggatgtgaagaacatcccggaagccgtcacc
aatgcgttccgaatcgcgtccgccggccaagcaggggcagcattcgtgagcttcccccaggacgtggtcaatgaagtgaccaacaccaaaaacgtcagagccgtagccgccccgaagctgggccctgcagcagatgacgcca
tctccgctgccatcgcgaagatccagaccgcaaagctgccggtcgtgctggtcggaatgaagggcggacgcccggaggccatcaaggccgtgcgtaaactgctgaagaaggtgcagctaccgttcgtggaaacctaccaggcc
gccggcaccctgagtcgggacttggaagaccagtatttcggccgtatcggcctgttccgcaaccagccgggcgacctgctcctggaacaagccgatgtggtgctgaccatcggctacgacccgatcgaatatgacccgaagttct
ggaacatcaatggcgaccgcacgatcatccatctggacgaaatcatcgccgacatcgaccatgcctatcagccggacctggaactgatcggcgacatcccgagcaccatcaaccacatcgaacacgatgccgtgaaggtggaa
tttgccgaacgcgaacagaagatcctgtcggacctgaagcagtatatgcatgagggcgaacaggtgcctgccgactggaagtcggacagagcccatccgctggaaatcgtgaaggaactgcgtaacgccgtcgacgaccatg
tcaccgtcacctgcgatatcggcagccatgccatttggatgagccgctacttccggagctatgaaccgctgaccctgatgatctccaacggtatgcagaccctcggcgtcgccctcccgtgggccatcggcgcaagtctggtgaa
gccgggcgaaaaagtggtcagcgtgtccggcgacggcggcttcctgttctccgctatggaactggaaaccgcggtccgcctgaaggccccgatcgtgcatatcgtgtggaacgacagcacctacgacatggtcgccttccagca
gctgaaaaagtacaaccgcaccagcgccgtggacttcggcaatatcgacatcgtgaagtatgccgaatccttcggagccaccggactgcgcgtggaatccccggaccagctggcggacgttctgcgtcagggcatgaatgccg
aaggtcccgtgattatcgatgtgcccgtcgactacagcgacaacatcaacctggcctcggacaaattgccgaaggagttcggcgaactgatgaaaacaaaagcactaTAAAAGGAGGTACGTATGaaccactcggc
cgaatgcacctgcgaagagagcctctgcgaaaccctccgggccttctcggcccagcacccggagagcgtcctgtaccagacgagcctgatgtcggcgctgctgtcgggcgtgtatgaaggctcgacgaccatcgccgac
ctgctgaagcatggcgacttcggcctgggcaccttcaatgaactggacggcgagctcatcgccttcagctcgcaggtgtatcagctccgggccgatggctccgcccggaaggcccagcccgaacagaagaccccgttcg
ccgtgatgacctggttccagccgcagtatcggaagaccttcgaccaccccgtgagccgccagcagctccacgaggtgatcgaccagcagatcccgagcgacaacctcttctgcgccctgcgcatcgacggccatttccgcc
acgcgcatacccgcaccgtcccgcggcagaccccgccctaccgcgccatgaccgatgtcctggatgaccagccggtcttccggttcaaccagcgcgagggcgtcctggtcggcttccgcaccccgcagcacatgcagggc
atcaacgtcgcgggctatcatgaacacttcatcaccgatgatcgcaagggcggcggccacctcctcgactaccagctggaccacggcgtcctgaccttcggcgaaatccataagctgatgatcgacctccccgccgacag
cgccttcctgcaggcgaatctgcatccggacaacctcgatgccgccatccgctccgtcgagtcgTGAAAGGAGGTACGTATGaaagccctgctgtggcataaccagcgcgacgtgcgggtggaagaggtccc
ggagcccgccgtccgcagcggcgcggtgaaaatcaaagtgaaatggtgcggcatctgtggcaccgacctgcatgaatatctggccggccccatcttcatcccgacggaggaacatccgctgacgcacgtcaaggc
cccggtcatcctcggccatgagttcagcggcgaggtggtggagatcggcgaaggcgtcaccaatcacaaagtcggcgatcgcgtggtcgtcgaaccgatctactcgtgcggcaagtgtgaggcgtgcaagcacgg
ccactataatgtctgcgagcagctggtgttccacggcctgggcggcgacggcggcttctcggagtacaccgtggtgccggcggatatggtccaccacatcccggatgaaatgacctacgagcagggcgccctg
gtcgagccggccgccgtggcggtgcacgcggtgcgccagagcaaactcaaggagggcgaagccgtggccgtcttcggctgcggcccgatcggcctgctggtcatccaggcggccaaagcggcgggcgcgacccc
cgtcatcgcggtcgagctgtcgaaggaacgccaggagctcgccaagctggcgggcgcggattatgtcctgaaccccgccgaacaggacgtggtggcggaaatccggaacctgaccaacggcctgggcgtcaacg
tctccttcgaggtcaccggcgtggaagtcgtcctgcggcaggcgatcgaatcgacctcgttcgagggccagacggtcatcgtgtcggtctgggagaaggacgccaccatcacgcccaataatctggtcctgaaaga
gaaggaagtggtcggcatcctcggctaccggcatatcttcccgtccgtcatcaagctgatctcgtcgggccagatccaggccgagaaactcatcaccaagaagatcacggtggaccaggtggtcgaagaaggcttc
gaagcgctggtcaaggataagaagcaggtgaagatcctcgtgtcgccgaagTGATTTCAGCCTGATACAGATTAAATCAGAACGCAGAAGCGGTCTGATAAAACAGAATTTGCCTGGCG
GCAGTAGCGCGGTGGTCCCACCTGACCCCATGCCGAACTCAGAAGTGAAACGCCGTAGCGCCGATGGTAGTGTGGGGTCTCCCCATGCGAGAGTAGGGAACTGCCAGGCA
TCAAATAAAACGAAAGGCTCAGTCGAAAGACTGGGCCTTTCGTTTTATCTGTTGTTTGTCGGTGAACGCTCTCCTGAGTAGGACAAATCCGCCGGGAGCGGATTTGAACGTT
GCGAAGCAACGGCCCGGAGGGTGGCGGGCAGGACGCCCGCCATAAACTGCCAGGCATCAAATTAAGCAGAAGGCCATCCTGACGGATGGCCTTTTTGCGTTTC

FIG. 6

| Strain | Chromosomal genoptype | Plasmid genotype |
|---|---|---|
| A | ΔMCA0838 ΔMCA0274::FRT (ΔMCA1474, pmxaF>BsuAlsS>KpnBudA>CauButA) | N/A |
| D | ΔMCA0838 ΔMCA0274::FRT (ΔMCA1474) | pmxaF>BsuAlsS>KpnBudA>CauButA |
| B | ΔMCA0838 ΔMCA0274::FRT (ΔMCA1474, pmxaF>BsuAlsS>KpnBudA>CauButA) | pmxaF>BsuAlsS>KpnBudA>CauButA |
| C | ΔMCA0838 ΔMCA0274::FRT (ΔMCA1474, pmxaF>BsuAlsS>KpnBudA>CauButA) | pmxaF>BsuAlsS>KpnBudA>CauButA |

FIG. 16

METHODS AND MICROORGANISMS FOR MAKING 2,3-BUTANEDIOL AND DERIVATIVES THEREOF FROM C1 CARBONS

CROSS-REFERENCE

This application is a division of U.S. application Ser. No. 16/481,799, filed Jul. 29, 2019, now U.S. Pat. No. 11,111,496, which claims priority benefit of U.S. Provisional Application Nos. 62/451,819, filed Jan. 30, 2017; 62/504,626, filed May 11, 2017; 62/512,312, filed May 30, 2017; and 62/588,985, filed Nov. 21, 2017. Each of these applications is hereby incorporated by reference in their entireties.

SEQUENCE LISTING

This application contains a Sequence Listing, which has been submitted electronically in ASCII format and is hereby incorporated by reference in its entirety. The ASCII copy, created on Nov. 8, 2021, is named 75594-338894_SL.txt and is 65,916 bytes in size.

BACKGROUND OF THE INVENTION

The compound 2,3-butanediol ("2,3-BDO"), also known as 2,3-butylene glycol, dimethylene glycol, dimethylethylene glycol and butane-2,3-diol ($C_4H_{10}O_2$; CAS No. 513-85-9) is a high value chemical that is currently produced mainly from petroleum sources. 2,3-BDO has a large number of industrial applications. For example, 2,3-BDO can be used as a precursor for various plastics, pesticides, synthetic rubber, printing inks, perfumes, fumigants, moistening and softening agents, explosives, plasticizers, food, and pharmaceuticals. (Garg, S. K., and Jain, A., "Fermentative production of 2,3-butanediol," *Bioresource Technology*, p. 103-109 (1995)).

2,3-BDO is currently produced through the use of crude oil. However, 2,3-BDO is also produced by a variety of microorganisms and can be found in cocoa butter, the roots of *Ruta graveolens*, sweet corn, and rotten mussels. 2,3-BDO is also a by-product of alcoholic fermentation by yeast and usually one of the most abundant minor constituent of wine. It originates from the reduction of acetoin. (Romano, P. and Suzzi, G., "Origin and Production of Acetoin during Wine Yeast Fermentation," Applied and Environmental Microbiology, p. 309-315 (1996)).

There has been some interest in recent years to produce 2,3-BDO by fermentation. Fermentation typically involves taking a carbon source (usually sugar) and fermenting it using a microorganism that is capable of converting the carbon source into a desired product.

Numerous attempts have been made to engineer *Saccharomyces cerevisiae* strains with reduced acetoin yields, by re-orienting carbons toward glycerol and 2,3-BDO to obtain low-alcohol yeasts with desirable organoleptic features, permitting the decrease of the ethanol contents in wines by up to 3° C. (Ehsani, M., et al., "Engineering of 2,3-butanediol dehydrogenase to reduce acetoin formation by glycerol-overproducing, low-alcohol *Saccharomyces cerevisiae*," Applied and Environmental Microbiology, p. 3196-3205 (2009)).

Costs to produce chemicals such as 2,3-BDO by fermentation typically depend on the carbon source used. Sugars are generally higher cost carbon sources that also result in a decrease of food supply. One carbon source is currently extremely cost-effective and abundant is natural gas. The primary source of carbon within natural gas is methane ($CH_4$), a C1 carbon. By using cheap carbon sources such as methane, 2,3-BDO can be produced economically.

2,3-BDO is also currently produced by some non-genetically modified microorganisms at very small titers. At these titers, the cost of fermentation would be too great to be economically feasible. Thus, genetic engineering is required to produce 2,3-BDO at an economically viable level. The challenge lies in engineering fermentation methods and microorganisms to efficiently convert cheap carbon sources, such as methane, into 2,3-BDO, using fermentative processes.

The subject matter of the present invention relates to microorganisms, such as methanotrophs or yeast, genetically modified so as to substantially improve 2,3-BDO biosynthesis.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

SUMMARY

Disclosed herein are genetically modified microorganisms that are capable of producing a desired organic compound, starting from a single carbon containing hydrocarbon molecule such as methane. Various methods of producing the desired organic compounds, including by using a genetically modified microorganism are disclosed.

For example, a genetically modified microorganism capable of converting a C1 carbon to 2,3-butanediol (2,3-BDO) is disclosed. Examples of C1 carbons that can be converted by the microorganisms can be carbon monoxide (CO), carbon dioxide ($CO_2$), methane ($CH_4$), or any combination thereof. The genetically modified microorganism can comprise one or more genes encoding heterologous enzymes such as, for example, an acetoin reductase, alpha-acetolactate decarboxylase (budA), and/or acetolactate synthase (AlsS). The AlsS gene in these microorganisms can be temporarily expressed. One or more of the genes can be under the control of a switch, such as an inducible or repressible promoter that is responsive to the presence or absence of a component in the media, e.g., a sugar such as arabinose or a rare earth element such as lanthanum.

The AlsS encoded can, for example, comprise an amino acid sequence that is at least 90% identical to any one of SEQ ID NOs: 1, 3, or 19. The alpha-acetolactate decarboxylase (budA) encoded can, for example, comprise an amino acid sequence that is at least 90% identical to SEQ ID NO: 7. The acetoin reductase encoded can, for example, comprise an amino acid sequence that is at least 90% identical to SEQ ID NO: 9. The acetoin reductase encoded can, for example, be a gram positive bacterium NADPH-dependent acetoin reductase, such as from the genus *Clostridium*, for example,

*Clostridium autoethanogenum*. In some cases the acetoin reductase can be NADPH-dependent. In some cases, the acetoin reductase can be NADH-dependent.

The genetically modified microorganism can, for example, be a methanotroph, such as from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, or *Methyloacidophilum*. The methanotroph can be from the genus *Methylococcus*, for example, from the species *Methylococcus capsulatus.*

The genetically modified microorganism can also be a prokaryote. In some cases, the genetically modified microorganism can be a bacterium, yeast, or algae.

In some cases, the genetically modified microorganisms can also produce a greater amount of 2,3-BDO at 42° C. compared to the same organism at 37° C. In some cases, the genetically modified microorganisms can also produce a greater amount of 2,3-BDO at 41° C. compared to the same organism at 37° C. In some cases, the genetically modified microorganism can produce a greater amount of 2,3-BDO at 42° C. compared to the same organism at 45° C. In some cases, the genetically modified microorganism can produce a greater amount of 2,3-BDO at 41° C. compared to the same organism at 45° C. In some cases, the genetically modified microorganism can produce a greater amount of 2,3-BDO at 37° C. compared to the same organism at 45° C.

In some cases, the heterologous gene encoding for the acetoin reductase, alpha-acetolactate decarboxylase, and/or acetolactate synthase is integrated by an integration vector into the genome of the microorganism. In some cases, the heterologous gene encoding for the acetoin reductase, alpha-acetolactate decarboxylase, and/or acetolactate synthase is expressed on an episomal vector.

In some cases, the heterologous gene encoding the acetolactate synthase is 5' in relation to any other heterologous gene. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene.

The order of the heterologous genes can be present on the vector prior, during, or after contact with the microorganism. For example, a gene can be 5' in relation to any other heterologous gene on the vector prior to contact with the microorganism. However, after contact with the microorganism, the gene can be inserted into a position or another gene can be inserted into the vector where the gene is then neither 5' or 3' in relation to any other heterologous gene on the vector. For instance, the vectors can be modified within a microorganism in such a way that the order of the genes are altered. In some cases, the specific order of the genes can be achieved after one or more heterologous gene(s) have been inserted into the genome of the microorganism. For example, different integration vectors can be used in order to achieve a specific gene order within the genome of the microorganism.

Disclosed herein are also vectors that comprise two or more of: an acetoin reductase (e.g., NADPH-dependent) gene, alpha-acetolactate decarboxylase (budA) gene, and an AlsS gene. In some cases, the gene encoding the acetolactate synthase is 5' in relation to any other heterologous gene. In some cases, the gene encoding the acetoin reductase is 3' in relation to any other heterologous gene. In some cases, the gene encoding the alpha-acetolactate decarboxylase is neither 5' or 3' in relation to any other heterologous gene. In some cases, the different genes can be under the control of a switch, such as an inducible or repressible promoter that is responsive to the presence or absence of a component in the media, e.g., a sugar such as arabinose or a rare earth element such as lanthanum. The different genes can be under the control of different promoters, such as a constitutively expressed promoter or a non-constitutively expressed promoter. The promoters used can also be active within a methanotroph. Examples of such vectors include those that comprise a nucleotide sequence that is at least 90% identical to any one of SEQ ID NOs: 15 to 18. In some cases, the vector is an integration vector, whereas in other cases, the vector is an episomally expressed vector.

Also disclosed herein is a method of making a genetically modified microorganism capable of converting a C1 carbon to 2,3-BDO comprising transforming a microorganism with a nucleic acid that expresses at least one heterologous gene encoding i) an acetoin reductase (e.g., NADPH-dependent); ii) an alpha-acetolactate decarboxylase (budA); iii) an acetolactate synthase (AlsS), or iv) any combination thereof. The at least one heterologous gene can, for example, be under the control of a switch, such as an inducible or repressible promoter that is responsive to the presence or absence of a component in the media, e.g., a sugar such as arabinose or a rare earth element such as lanthanum. In some cases, the method can make genetically modified microorganisms that can produce a greater amount of 2,3-BDO at 42° C. compared to the same organism at 37° C. In some cases, the method can make genetically modified microorganisms that can produce a greater amount of 2,3-BDO at 41° C. compared to the same organism at 37° C. In some cases, the method can make genetically modified microorganisms that can produce a greater amount of 2,3-BDO at 42° C. compared to the same organism at 45° C. In some cases, the method can make genetically modified microorganisms that can produce a greater amount of 2,3-BDO at 41° C. compared to the same organism at 45° C. In some cases, the method can make genetically modified microorganisms that can produce a greater amount of 2,3-BDO at 37° C. compared to the same organism at 45° C.

In some cases, the methods can comprise microorganisms in which the gene(s) encoding for the heterologous acetoin reductase, heterologous alpha-acetolactate decarboxylase, and/or heterologous acetolactate synthase is integrated by an integration vector into the genome of the microorganism. In some cases, the methods can comprise microorganisms in which the gene(s) encoding for the heterologous acetoin reductase, alpha-acetolactate decarboxylase, and/or acetolactate synthase is expressed on an episomal vector. In some cases, the method can comprises microorganism in which the gene(s) encoding for the heterologous acetoin reductase, alpha-acetolactate decarboxylase, and/or acetolactate synthase are expressed on both an episomal vector and integrated into the genome of the microorganism (e.g., by an integration vector).

In some cases, the heterologous gene encoding the acetolactate synthase is 5' in relation to any other heterologous gene. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene.

Further disclosed is a method of making 2,3-BDO comprising (a) contacting a genetically modified microorganism with a C1 carbon, where the microorganism comprises at least one heterologous gene encoding for (i) an acetoin reductase (e.g., NADPH-dependent); (ii) an alpha-acetolactate decarboxylase (budA); (iii) an AlsS; or (iv) any combination thereof; and (b) growing the microorganism to produce 2,3-BDO. In some cases, the heterologous gene encoding for the acetoin reductase, alpha-acetolactate decarboxylase, and/or acetolactate synthase is integrated by an integration vector into the genome of the microorganism. In some cases, the heterologous gene encoding for the acetoin reductase, alpha-acetolactate decarboxylase, and/or acetolactate synthase is expressed on an episomal vector. In some cases, the method can comprises microorganism in which the gene(s) encoding for the heterologous acetoin reductase, alpha-acetolactate decarboxylase, and/or acetolactate synthase are expressed on both an episomal vector and integrated into the genome of the microorganism (e.g., by an integration vector). In some cases, the heterologous gene encoding the acetolactate synthase is 5' in relation to any other heterologous gene. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene. The method can comprise growing the microorganism at a temperature of between 32° C. to 49° C. In some cases, the microorganism can be grown at a temperature of between 37° C. to 42° C. In some cases, the microorganism can be grown at a temperature of about 42° C. In some cases, the microorganism can be grown at a temperature of about 41° C. In some cases, the at least one heterologous gene can, for example, be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal such as lanthanum (e.g., at least 1 μM lanthanum) and then subsequently the rare earth metal such as lanthanum can be diluted. This can occur before growing the microorganism to produce 2,3-BDO. The 2,3-BDO produced from this method can be recovered and, in some cases, be substantially pure.

Additionally disclosed is a method of making acetoin comprising (a) contacting a genetically modified microorganism with a C1 carbon, where the microorganism comprises a heterologous gene encoding for alpha-acetolactate decarboxylase (budA); and (b) growing the microorganism to produce acetoin. In some cases, the heterologous gene encoding for the alpha-acetolactate decarboxylase is integrated by an integration vector into the genome of the microorganism. In some cases, the heterologous gene encoding for the alpha-acetolactate decarboxylase is expressed on an episomal vector. In some cases, the heterologous gene encoding for the alpha-acetolactate decarboxylase is expressed on both an episomal vector and integrated into the genome of the microorganism (e.g., by an integration vector). The method can comprise growing the microorganism at a temperature of between 32° C. to 49° C. In some cases, the microorganism can be grown at a temperature of between 37° C. to 42° C. In some cases, the microorganism can be grown at a temperature of about 42° C. In some cases, the microorganism can be grown at a temperature of about 41° C. In some cases, the budA gene can, for example, be under the control of a switch, such as an inducible or repressible switch, e.g., an arabinose or lanthanum switch. In some cases, the microorganism can be first grown in media containing lanthanum (e.g., at least 1 μM lanthanum). The lanthanum can be subsequently consumed, removed, and/or diluted. This can occur before growing the microorganism to produce acetoin. The acetoin produced from this method can be recovered and, in some cases, be substantially pure. Should the acetoin produced by this method be not substantially pure, the non-acetoin by-products, such as 2,3-BDO, can be recovered as well.

Once 2,3-BDO is made, it can be converted into other desired products, for example, such as butadiene or methyl ethyl ketone (MEK). Thus, also disclosed herein is a method of making butadiene comprising (a) contacting a genetically modified microorganism with a C1 carbon substrate, where the microorganism comprises at least one heterologous gene encoding (i) an NADPH-dependent acetoin reductase; (ii) an alpha-acetolactate decarboxylase (budA); (iii) an AlsS; or (iv) any combination thereof; and (b) growing the microorganism to produce 2,3-BDO; and (c) contacting the 2,3-BDO from (b) with a catalyst to produce butadiene. In some cases, the 2,3-BDO from (b) is removed prior to (c). In some cases, the heterologous gene encoding for the acetoin reductase, alpha-acetolactate decarboxylase, and/or acetolactate synthase is integrated by an integration vector into the genome of the microorganism. In some cases, the heterologous gene encoding for the acetoin reductase, alpha-acetolactate decarboxylase, and/or acetolactate synthase is expressed on an episomal vector. In some cases, the heterologous gene encoding for the acetoin reductase, alpha-acetolactate decarboxylase, and/or acetolactate synthase is expressed on both an episomal vector and integrated into the genome of the microorganism (e.g., by an integration vector). In some cases, the heterologous gene encoding the acetolactate synthase is 5' in relation to any other heterologous gene. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene. The method can comprise growing the microorganism at a temperature of between 32° C. to 49° C. In some cases, the microorganism can be grown at a temperature of between 37° C. to 42° C. In some cases, the microorganism can be grown at a temperature of about 42° C. In some cases, the microorganism can be grown at a temperature of about 41° C. Additionally, the catalyst can be any catalyst that is capable of dehydrating 2,3-BDO, such as a $SiO_2$-supported cesium dihydrogen phosphate ($CsH_2PO_4$) catalyst. The butadiene produced from this method can be recovered and in some cases can be substantially pure. The butadiene can also be further processed into a synthetic rubber.

Disclosed also is a method of making MEK comprising (a) contacting a genetically modified microorganism with a C1 carbon substrate, where the microorganism comprises at least one heterologous gene encoding (i) an NADPH-dependent acetoin reductase; (ii) an alpha-acetolactate decarboxylase (budA); (iii) an acetolactate synthase (AlsS); or (iv) any combination thereof; and (b) growing the microorganism to produce 2,3-BDO; and (c) contacting the 2,3-BDO from (b) with a catalyst to produce MEK. In some cases, the heterologous gene encoding for the acetoin reductase, alpha-acetolactate decarboxylase, and/or acetolactate synthase is integrated by an integration vector into the genome of the microorganism. In some cases, the heterologous gene encoding for the acetoin reductase, alpha-acetolactate decarboxylase, and/or acetolactate synthase is expressed on an episomal vector. In some cases, the heterologous gene encoding for the acetoin reductase, alpha-acetolactate decarboxylase, and/or acetolactate synthase are expressed on both an episomal vector and integrated into the genome of the microorganism (e.g., by an integration vector). In some cases, the heterologous gene encoding the acetolactate synthase is 5' in relation to any other heterologous gene. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene. The method can comprise growing the microorganism at a temperature of between 32° C. to 49° C. In some cases, the microorganism can be grown at a temperature of between 37° C. to 42° C. In some cases, the microorganism can be grown at a temperature of about 42° C. In some cases, the microorganism can be grown at a temperature of about 41° C. In some cases, the catalyst is a solid acid catalyst. The MEK produced from this method can be recovered and in some cases be substantially pure. The MEK can also be further processed into plastics, textiles, paraffin wax, lacquer, varnishes, paint remover, glues, and/or cleaning agents. In some cases, the catalyst from (c) can be a diol dehydratase (B12). In some cases, a diol dehydratase gene can be expressed by the same or different genetically modified microorganism. Thus, disclosed herein is a method of making MEK comprising (a) contacting a genetically modified microorganism with a C1 carbon substrate, where the microorganism comprises at least one heterologous gene encoding (i) an NADPH-dependent acetoin reductase; (ii) an alpha-acetolactate decarboxylase (budA); (iii) an AlsS; (iv) a diol dehydratase or (v) any combination thereof; and (b) growing the microorganism to produce MEK.

Also disclosed are isolated polynucleic acids comprising nucleotide sequences that are at least 84% identical to SEQ ID NO: 2, at least 88% identical to SEQ ID NO: 4, or at least 60% identical to SEQ ID NO: 20. These nucleotide sequences can encode for a protein that has acetolactate synthase activity. Further disclosed are, isolated polynucleic acids comprising a nucleotide sequence that is at least 85% identical to SEQ ID NOs: 6 or 8. These nucleotide sequences can encode a protein that has alpha-acetolactate decarboxylase activity. Additionally disclosed are isolated polynucleic acids that are at least 85% identical to any one of SEQ ID NOs: 10, 12, or 14. These nucleotide sequences can encode a protein that has butanediol dehydrogenase activity.

BRIEF DESCRIPTION OF THE DRAWINGS

FIG. 3 shows the nucleotide sequence of the 2,3-BDO pathway gene expression cassette in strain XZ58 (SEQ ID NO: 15). Proceeding in the 5' to 3' direction, the underlined uppercase sequences represent the pBAD promoter. The initiator ATG and terminator TAA for the g.Bsu AlsS (acetolactate synthase) gene are indicated by bold uppercase while the coding region is indicated in lowercase. The ribosomal binding site rbsGTW001 is indicated by boxed uppercase text. The initiator ATG and terminator TGA for the g.Kpn BudA gene are indicated by bold italics uppercase while the coding region is indicated in italics lowercase. The terminator rrnB is indicated in uppercase, followed by a pmxaF promoter that indicated by underlined italics uppercase. The initiator ATG and terminator TGA for the g.Cau ButA gene are indicated by bold italics uppercase while the coding region is indicated in bold italics lowercase. The terminator lambda TO is indicated in italics uppercase.

FIG. 4 shows the nucleotide sequence of the 2,3-BDO pathway genes expression cassette in strain XZ59 (SEQ ID NO: 16). Proceeding in the 5' to 3' direction, the underlined uppercase sequences represent the pBAD promoter. The initiator ATG and terminator TAA for the g.Bsu AlsS gene are indicated by bold uppercase while the coding region is indicated in lowercase. The ribosomal binding site rbsGTW001 is indicated by boxed uppercase text. The initiator ATG and terminator TGA for the g.Kpn BudA gene are indicated by bold italics uppercase while the coding region is indicated in italics lowercase. The terminator rrnB is indicated in uppercase, followed by a pmxaF promoter that indicated by underlined italics uppercase. The initiator ATG and terminator TGA for the g.Bsu ButA gene are indicated by bold italics uppercase while the coding region is indicated in bold italics lowercase. The terminator lambda TO is indicated in italics uppercase.

FIG. 5 shows the nucleotide sequence of the 2,3-BDO pathway genes expression cassette in strain XZ06 (SEQ ID NO: 17). Proceeding in the 5' to 3' direction, the underlined uppercase sequences represent the pBAD promoter. The initiator ATG and terminator TAA for the g.Bsu AlsS gene are indicated by bold uppercase while the coding region is indicated in lowercase. The ribosomal binding site rbsGTW001 is indicated by boxed uppercase text. The initiator ATG and terminator TGA for the g.Kpn BudA gene are indicated by bold italics uppercase while the coding region is indicated in italics lowercase, followed by an additional ribosomal binding site rbsGTW001 that is indicated by boxed uppercase text. The initiator ATG and terminator TGA for the g.Cau ButA gene are indicated by bold italics uppercase while the coding region is indicated in bold italics lowercase. The terminator rrnB is indicated in uppercase.

FIG. 6 demonstrates the nucleotide sequence of the 2,3-BDO pathway genes expression cassette in strain XZ08 (SEQ ID NO: 18). Proceeding in the 5' to 3' direction, the underlined uppercase sequences represent the pBAD promoter. The initiator ATG and terminator TAA for the g.Bsu AlsS gene are indicated by bold uppercase while the coding region is indicated in lowercase. The ribosomal binding site rbsGTW001 is indicated by boxed uppercase text. The initiator ATG and terminator TGA for the g.Kpn BudA gene are indicated by bold italics uppercase while the coding region is indicated in italics lowercase, followed by an additional ribosomal binding site rbsGTW001 that is indicated by boxed uppercase text. The initiator ATG and terminator TGA for the g.Bsu ButA gene are indicated by bold italics uppercase while the coding region is indicated in bold italics lowercase. The terminator rrnB is indicated in uppercase.

FIG. 7A demonstrates acetoin and 2,3-BDO production of 21 different strains after 96 hours following dilution of lanthanum containing media. The strains and genotypes of the strains are listed in Table 3 and 4. For strains 1 to 21, production titers were measured 96 hours after a 1:10 (10×) dilution of the culture into fresh medium whereas for strains 22 to 42 production titers were measured after a 1:50 (50×) dilution. Strains 22 to 27 produced high levels of 2,3-BDO, compared to strains subjected to less dilution prior to the 2,3-BDO production phase. FIG. 7B demonstrates acetoin and 2,3-BDO production of 21 different strains after 120 hours following dilution of lanthanum containing media. The strains and genotypes of the strains are listed in Table 3 and 4. For strains 1 to 21, production titers were measured 120 hours after a 1:10 (10×) dilution of the culture into fresh medium, whereas for strains 22 to 42 production titers were measured after a 1:50 (50×) dilution. Strains 22 to 27 produced high levels of 2,3-BDO, compared to strains subjected to less dilution prior to the 2,3-BDO production phase.

FIG. 16 shows a summary of the genotypes of the Strains A, B, C, and D.

DETAILED DESCRIPTION OF THE INVENTION

Figure 1:
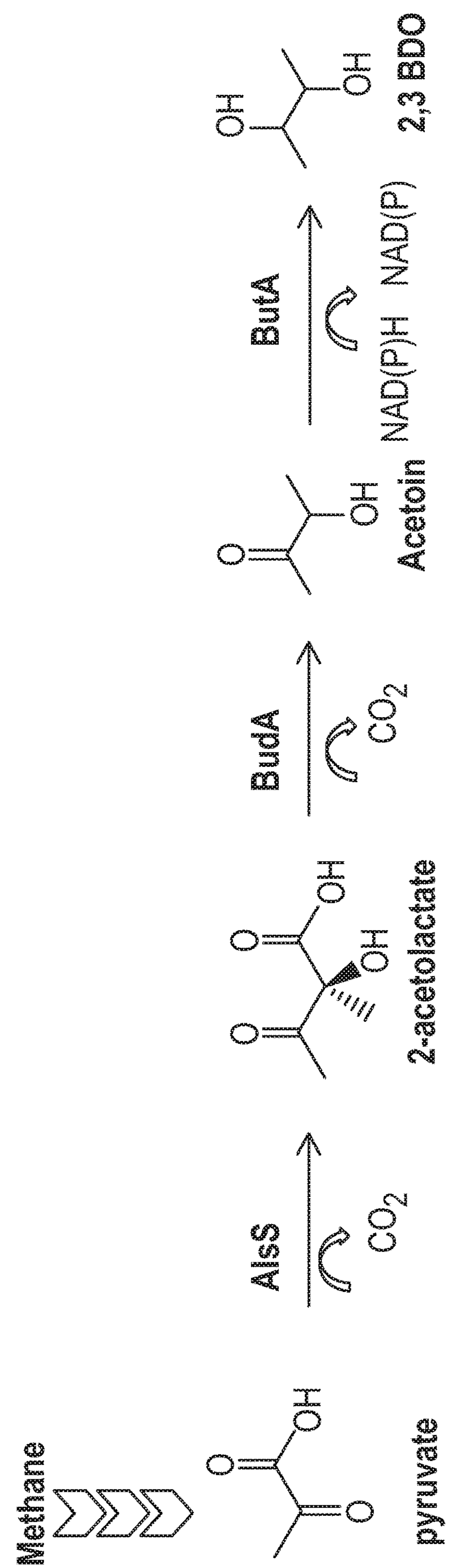
FIG. 1 shows a metabolic pathway from methane ($CH_4$) to 2,3-BDO.

As summarized above, aspects of the invention include genetically modified microorganisms that can convert carbon substrates into chemical products such as 2,3-BDO. The genetically modified microorganisms include methanotrophs, which are capable of generating 2,3-BDO at high titers from a methane source. Also disclosed are methods of making and using such genetically modified microorganisms.

Before the present invention is described in greater detail, it is to be understood that this invention is not limited to particular cases described, as such can, of course, vary. It is also to be understood that the terminology used herein is for the purpose of describing particular cases only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

I. Definitions

The term "2,3-butanediol" or "2,3-BDO" and their grammatical equivalents as used herein can refer to all enantiomeric and diastereomeric forms of the compound, including (R,R), (S,S) and mesa forms, in racemic, partially stereoisomerically pure and/or substantially stereoisomerically pure forms.

The term "butene" or "butylene" and their grammatical equivalents as used herein can refer to all structural isomers of the alkene including 2-butene, but-1-ene, 2-methylpropene, and all stereoisomeric and geometric isomeric forms of the compound, including Z-but-2-ene, E-but-2-ene, in mixtures of isomers and pure and/or substantially pure forms.

The term "butadiene" and their grammatical equivalents as used herein can refer to all geometric isomers of the diene including cis and trans 1,3-butadiene, in mixtures of isomers and pure and/or substantially pure forms.

The term "methyl ethyl ketone" or "MEK" or "butanone" and their grammatical equivalents as used herein can refer to all isomers of the ketone in partially pure and/or substantially pure forms.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical value disclosed throughout can be "about" that numerical value even without specifically mentioning the term "about."

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The term "genetic modification" or "genetically modified" and their grammatical equivalents as used herein can refer to one or more alterations of a nucleic acid, e.g., the nucleic acid within a microorganism's genome. For example, genetic modification can refer to alterations, additions, and/or deletion of nucleic acid (e.g., whole genes or fragments of genes).

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

As will be apparent to those of skill in the art upon reading this disclosure, each of the individual cases described and illustrated herein has discrete components and features which may be readily separated from or combined with the features of any of the other several cases without departing from the scope or spirit of the present invention. Any recited method can be carried out in the order of events recited or in any other order which is logically possible.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

The term "polynucleic acid" and its grammatical equivalents as used herein can refer to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The nucleotides can be naturally occurring, artificial and/or modified nucleotides. The term "nucleoside" refers to a compound (as guanosine or adenosine) that consists of a purine or pyrimidine base combined with deoxyribose or ribose and is found especially in polynucleic acids. The term "nucleotide analog" or "nucleoside analog" refers, respectively, to a nucleotide or nucleoside in which one or more individual atoms have been replaced with a different atom or with a different functional group. The term "polynucleic acid," as used herein, includes nucleic acids of any length, including DNA, RNA, open reading frames, analogs and fragments thereof.

Examples of polynucleic acids include oligonucleotides that typically range in length from 2 nucleotides to about 100 nucleotides, and polynucleotides, which typically have a length greater than about 100 nucleotides. It is understood that the polynucleic acids described herein include polynucleotides such as "genes," "promoters," "operons," and/or "vectors." As used herein, the term "gene" and its grammatical equivalents refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "promoter" and its grammatical equivalents as used herein can refer to a nucleic acid sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" and its grammatical equivalents as used herein can refer to the association of nucleic acid sequences on a single polynucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "codon optimized" and its grammatical equivalents as used herein insofar as it refers to genes or coding regions of nucleic acid molecules (or open reading frames) for transformation of various hosts, can refer to the alteration of codons in the gene or coding regions of the nucleic acid molecules to reflect the typical codon usage of the host organism without altering the polypeptide encoded by the DNA.

The term "open reading frame" ("ORF") and its grammatical equivalents as used herein can refer to a polynucleic acid or nucleic acid sequence (whether naturally occurring, non-naturally occurring, or synthetic) comprising an uninterrupted reading frame consisting of (i) an initiation codon, (ii) a series of two (2) of more codons representing amino acids, and (iii) a termination codon, the ORF being read (or translated) in the 5' to 3' direction.

The term "operon" and its grammatical equivalents as used herein can refer to two or more genes which are transcribed as a single transcriptional unit from a common promoter. In certain cases, the genes, polynucleotides or ORFs comprising the operon are contiguous. It is understood that transcription of an entire operon can be modified (i.e., increased, decreased, or eliminated) by modifying the common promoter. Alternatively, any gene, polynucleotide or ORF, or any combination thereof in an operon can be modified to alter the function or activity of the encoded polypeptide. The modification can result in an increase or a decrease in the activity or function of the encoded polypeptide. Further, the modification can impart new activities on the encoded polypeptide.

The term "vector" and its grammatical equivalents as used herein can refer to any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes", that is, that replicate autonomously or can integrate into a chromosome of a host microorganism. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

The term "polypeptide" and its grammatical equivalents as used herein can refer to any organic polymer comprising two or more amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein," "polypeptide," and "peptide" are used interchangeably herein when referring to a gene product. Unless otherwise indicated, a particular polypeptide also implicitly encompasses conservatively-substituted variants thereof.

The term "enzyme" and its grammatical equivalents as used herein can refer to any of numerous proteins that act as a biological catalyst. Similar to traditional chemical catalysts, enzymes speed the rate of biological reactions by producing a transition state with a lower energy of activation than the uncatalyzed reaction. In other words, enzymes are proteins specialized for the reactions they catalyze. Examples of enzymes described herein include acetolactate synthase (encoded by the AlsS gene), alpha-acetolactate decarboxylase (encoded by the gene BudA), and acetoin reductase (encoded by the gene ButA).

The phrases "recombinant host cell," "genetically engineered host cell," "engineered host cell," "genetically modified host cell," and their grammatical equivalents as used herein may be used interchangeably and can refer to host cells that have been genetically modified to: (a) express one or more exogenous polynucleic acids; (b) over-express one or more endogenous and/or one or more exogenous polynucleic acids, such as those included in a vector, or which have an alteration in expression of an endogenous gene; or (c) knock-out or down-regulate an endogenous gene. In addition, certain genes may be physically removed from the genome (e.g., knock-outs) or they may be engineered to have reduced, altered or enhanced activity. The phrases "recombinant host cell," "genetically engineered host cell," "engineered host cell," and "genetically modified host cell" refer not only to the particular subject host cell, but to the progeny or potential progeny of such a cell. Because certain modifications may occur in succeeding generations due to either mutation or environmental influences, such progeny may not, in fact, be identical to the parent cell, but are still included within the scope of the term(s) as used herein.

The term "in vitro" and its grammatical equivalents as used herein can refer to outside of a living cell, regardless of the location of the cell. The term "in vivo" and its grammatical equivalents as used herein can refer to inside a living cell, regardless of the location of the cell.

The terms "engineer," "genetically engineer," "modify," "genetically modify," and their grammatical equivalents as used herein can refer to any manipulation of a microorganism that results in a detectable change in the microorganism, where the manipulation includes, but is not limited to, introducing non-native metabolic functionality via heterologous (exogenous) polynucleic acids or removing native-functionality via polynucleic acid deletions, mutations or knock-outs. The term "metabolically engineered" generally involves rational pathway design and assembly of biosynthetic genes (or open reading frames), genes associated with operons, and control elements of such polynucleic acids, for the production of a desired metabolite. "Metabolically engineered" may further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

The term "switch" and its grammatical equivalents as used herein can mean a regulatory unit of a gene or genes that is capable of responding to a particular stimulus to either induce or repress expression. For example, switches can include regulatory units that respond to sugar (e.g., arabinose) or rare earth metals (e.g., lanthanum).

As used herein, the terms "genetic modification," "genetically modified" and their grammatical equivalents can refer to any modification of a polynucleic acid and/or polypeptide that results in an altered nucleic acid or polypeptide (i.e., relative to the wild-type nucleic acid or polypeptide sequence). Genetic modification includes, for example, point mutations, substitutions, deletions, or insertions of single or multiple residues in a polynucleic acid (or the encoded polypeptide), which includes alterations arising within a protein-encoding region of a gene as well as alterations in regions outside of a protein-encoding sequence, such as, but not limited to, regulatory or promoter sequences. A genetic modification may be an alteration of any type. For instance, the modification may be a deletion, insertion, mutation, rearrangement, or any combination thereof. In certain cases, a portion of a genetically modified microorganism's genome may be replaced with one or more heterologous (exogenous) polynucleic acids. In some cases, the modification is naturally-occurring. In other cases, the modification is the results of artificial selection pressure. In still other cases, the modification is the result of genetic engineering. One form of genetic modification is disruption, such as by knockout. As used herein, the term "introducing," and its grammatical equivalents as used in phrases such as "introducing into the host cell" at least one polynucleic acid includes methods known in the art for introducing polynucleic acids into a cell, including, but not limited to transformation (e.g., calcium chloride, electroporation), transduction, transfection, conjugation and the like.

As used herein, the terms "expression" or "expressed," and their grammatical equivalents with respect to a gene sequence, ORF sequence, or polynucleic acid sequence, can refer to transcription of the gene, open reading frame or polynucleic acid and, as appropriate, translation of the resulting mRNA transcript to a protein. Thus, as will be clear from the context, expression of a protein results from transcription and translation of the open reading frame sequence. The level of expression of a desired end product in a host cell may be determined on the basis of either the amount of corresponding mRNA that is present in the host cell, or the amount of the desired end product encoded by the selected sequence. For example, mRNA transcribed from a selected sequence can be quantitated by PCR or by northern hybridization (see, e.g., Sambrook et al., *Molecular Cloning: A Laboratory Manual*, Cold Spring Harbor Laboratory Press, 1989). Protein encoded by a selected sequence can be quantitated by various methods (e.g., by ELISA, by assaying for the biological activity of the protein, or by employing assays that are independent of such activity, such as western blotting or radioimmunoassay, using antibodies that are recognize and bind reacting the protein).

As used herein, the term "endogenous," and its grammatical equivalents when used in reference to polynucleic acids (and the polypeptides encoded therein), an refer to polynucleic acids and polypeptides that are expressed in the organism in which they originated (i.e., they are innate to the organism). In contrast, the terms "heterologous" and "exogenous" are used interchangeably, and as defined herein with reference to polynucleic acids (and the polypeptides encoded therein), indicates polynucleic acids and polypeptides that are expressed in an organism other than the organism from which they (i.e., the polynucleic acid or polypeptide sequences) originated or where derived. In some cases, the term "heterologous" and its grammatical equivalents can mean derived from a different species. For example, a "heterologous gene" can mean a gene that is from a species different than the reference species. For example, a methanotroph comprising a "heterologous gene" comprises a gene that is not from the same methanotroph. The gene can be from a different microorganism such as yeast or from a different species such as a different methanotroph species.

As used herein, the term "substrate" and its grammatical equivalents can refer to any substance or compound that is converted, or meant to be converted, into another compound by the action of an enzyme. The term includes not only a single compound, but also combinations of compounds, such as solutions, mixtures and other materials which contain at least one substrate, or derivatives thereof.

As used herein, the terms "C1 carbon," "C1-carbon substrates" and their grammatical equivalents can refer to any organic compound that contains a single carbon atom. Examples include, but are not limited to, carbon monoxide (CO), methane ($CH_4$), and carbon dioxide ($CO_2$).

As used herein, the term "fermentation" or "fermentation process," and its grammatical equivalents, can be a process in which a host cell is cultivated in a culture medium containing raw materials, such as feedstock and nutrients, where the cell converts raw materials, such as a feedstock, into desirable end products.

As used herein, the term "homolog" and its grammatical equivalents, as used with respect to an original protein, polypeptide, gene, or polynucleic acid (or ORF encoding the same) of a first family or species, can refer to distinct proteins, genes, or polynucleic acids of a second family or species that correspond (structurally, functionally, and/or genomically) to the original protein, gene, or polynucleic acid of the first family or species. Most often, "homologs" will have functional, structural or genomic similarities. Techniques are known by which homologs of an protein, gene or polynucleic acid can readily be cloned using genetic probes and PCR. Identity of cloned sequences as "homologs" can be confirmed using functional assays and/or by genomic mapping of the genes.

A polypeptide (or protein or enzyme) has "homology" or is "homologous" to a second polypeptide if the nucleic acid sequence that encodes the polypeptide has a similar sequence to the nucleic acid sequence that encodes the second polypeptide. Alternatively, a polypeptide has homology to a second polypeptide if the two proteins have "similar" amino acid sequences. Thus, the terms "homologous proteins" or "homologous polypeptides" and their grammatical equivalents can refer to two polypeptides have similar amino acid sequences. In certain cases of the invention, polynucleotides and polypeptides homologous to one or more polynucleotides and/or polypeptides set forth in Table 1 may be readily identified using methods known in the art for sequence analysis and comparison.

A homologous polynucleotide or polypeptide sequence of the invention may also be determined or identified by BLAST analysis (Basic Local Alignment Search Tool) or similar bioinformatic tools, which compare a query nucleotide or polypeptide sequence to a database of known sequences. For example, a search analysis may be done using BLAST to determine sequence identity or similarity to previously published sequences, and if the sequence has not yet been published, can give relevant insight into the function of the DNA or protein sequence.

As used herein, the term "substantially pure" and its grammatical equivalents can refer to a particular substance that does not contain a majority of another substance. For example, "substantially pure 2,3-BDO" can mean at least 90% 2,3-BDO. In some instances, "substantially pure 2,3-BDO" can mean at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, or 99.9999% 2,3-BDO. For example, substantially pure 2,3-BDO can mean at least 70% 2,3-BDO. In some cases, substantially pure 2,3-BDO can mean at least 75% 2,3-BDO. In some cases, substantially pure 2,3-BDO can mean at least 80% 2,3-BDO. In some cases, substantially pure 2,3-BDO can mean at least 85% 2,3-BDO. In some cases, substantially pure 2,3-BDO can mean at least 90% 2,3-BDO. In some cases, substantially pure 2,3-BDO can mean at least 91% 2,3-BDO. In some cases, substantially pure 2,3-BDO can mean at least 92% 2,3-BDO. In some cases, substantially pure 2,3-BDO can mean at least 93% 2,3-BDO. In some cases, substantially pure 2,3-BDO can mean at least 94% 2,3-BDO. In some cases, substantially pure 2,3-BDO can mean at least 95% 2,3-BDO. In some cases, substantially pure 2,3-BDO can mean at least 96% 2,3-BDO. In some cases, substantially pure 2,3-BDO can mean at least 97% 2,3-BDO. In some cases, substantially pure 2,3-BDO can mean at least 98% 2,3-BDO. In some cases, substantially pure 2,3-BDO can mean at least 99% 2,3-BDO.

As used herein, the term "substantially similar" and its grammatical equivalents, when used in reference to the similarity between a sequence and a reference sequence, means that the sequences are at least 50% (but not 100%) identical. In some cases, the sequences are 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical. In some cases, the term substantially similar refers to a sequence that is at least 50% identical. In some instances, the term substantially similar refers to a sequence that is 55% identical. In some instances, the term substantially similar refers to a sequence that is 60% identical. In some instances, the term substantially similar refers to a sequence that is 65% identical. In some instances, the term substantially similar refers to a sequence that is 70% identical. In some instances, the term substantially similar refers to a sequence that is 75% identical. In some instances, the term substantially similar refers to a sequence that is 80% identical. In other instances, the term substantially similar refers to a sequence that is 81% identical. In other instances, the term substantially similar refers to a sequence that is 82% identical. In other instances, the term substantially similar refers to a sequence that is 83% identical. In other instances, the term substantially similar refers to a sequence that is 84% identical. In other instances, the term substantially similar refers to a sequence that is 85% identical. In other instances, the term substantially similar refers to a sequence that is 86% identical. In other instances, the term substantially similar refers to a sequence that is 87% identical. In other instances, the term substantially similar refers to a sequence that is 88% identical. In other instances, the term substantially similar refers to a sequence that is 89% identical. In some instances, the term substantially similar refers to a sequence that is 90% identical. In some instances, the term substantially similar refers to a sequence that is 91% identical. In some instances, the term substantially similar refers to a sequence that is 92% identical. In some instances, the term substantially similar refers to a sequence that is 93% identical. In some instances, the term substantially similar refers to a sequence that is 94% identical. In some instances, the term substantially similar refers to a sequence that is 95% identical. In some instances, the term substantially similar refers to a sequence that is 96% identical. In some instances, the term substantially similar refers to a sequence that is 97% identical. In some instances, the term substantially similar refers to a sequence that is 98% identical. In some instances, the term substantially similar refers to a sequence that is 99% identical. In some instances, the term substantially similar refers to a sequence that is 100% identical. To determine the percentage of identity between two sequences, the two sequences are aligned, using, for example, the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919) using a gap opening penalty of 10 and a gap extension penalty of 0.1, so that the highest order match obtained between two sequences where at least 50% of the total length of one of the two sequences is involved in the alignment.

II. Genetically Modified Microorganisms and Methods of Making the Same

The present disclosure is directed, in part, to genetically modified microorganisms that have dramatically improved 2,3-BDO biosynthesis rates as compared to those seen in wild-type microorganisms. In some cases, the biosynthesis rates are orders of magnitude higher than what could be normally produced. In some instances, the microorganisms that do not naturally produce 2,3-BDO have been genetically modified to synthesize 2,3-BDO, including at significantly high levels.

Microorganisms

In some cases, the microorganisms can use C1 carbon substrates, such as, CO, $CO_2$, and $CH_4$, to synthesize a desired end product. This, however, does not mean that these microorganisms use solely C1 carbons. Some of the microorganisms can be made to utilize additional carbon substrates, including carbon substrates that the microorganism naturally uses. For example, if the microorganism naturally uses sugar for carbon substrates, this microorganism can be made to utilize a different carbon source such as a C1 carbon.

The microorganisms can be a prokaryote or a eukaryote. In some cases, for example, the microorganisms can be bacteria, yeast, or algae.

Microorganisms that can convert C1 carbon substrates into desired products include those capable of using natural gas as a carbon substrate. For example, the microorganism can use methane contained within the natural gas a as a carbon source to make such desired products. Such microorganisms can include methanotrophs. Methanotrophs that can be particularly useful include those from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloacidophilum*, or any combinations thereof. In some cases, the methanotroph is from the genus *Methylococcus*. In one instance, the methanotroph can be a methanotroph from the species *Methylococcus capsulatus.*

Some microorganisms are capable of using $CO_2$ as a substrate. Such microorganisms include methanogens.

Microorganisms that are capable of using $CO_2$ as a substrate can contain chlorophyll. Examples thereof include algae and cyanobacteria.

Some microorganisms are capable of using CO as a substrate. Examples include anaerobic microorganisms such as *Clostridium*. These microorganism can be genetically modified so as to make substantial amounts of 2,3-BDO.

In some cases, the genetically modified microorganisms described throughout can produce a desired product at higher titers when fermented at a higher temperature. For example, the genetically modified microorganisms can be made to produce higher titers of products, such as 2,3-BDO, butadiene, and/or MEK, when incubated at a temperature of greater than 37° C. (but no greater than a temperature of 100° C.). In some cases, the genetically modified microorganisms can be made to produce higher product titers when incubated at 42° C. compared to at 37° C. In some cases, the genetically modified microorganisms can be made to produce higher product titers when incubated at 41° C. compared to at 37° C. In some cases, the genetically modified microorganism can be made to produce higher product titers when incubated at 42° C. compared to at 45° C. In some cases, the genetically modified microorganism can be made to produce higher product titers when incubated at 41° C. compared to at 45° C. In some cases, the genetically modified microorganisms can be made to produce higher product titers when incubated at 37° C. compared to at 45° C. In some cases, the genetic modifications produce the increased tolerance/preference for higher temperatures.

Enzymes

In order to genetically engineer certain microorganisms to produce certain useful products, such as 2,3-BDO, butadiene, and/or MEK, microorganisms can be transformed with one or more genes that encode specific enzymes. These genes can be heterologous to the microorganism.

For example, in order to engineer a microorganism that can produce 2,3-BDO, one or more genes (e.g., heterologous genes) can be transformed or transfected into the microorganism, either transiently or stably. In some cases, one or more of these genes can be episomally expressed. In some cases, one of more of these genes can be integrated into the genome of the microorganism. In some cases, one or more of these genes can be episomally expressed whereas one or more of these genes can also be integrated into the genome of the microorganism. In some cases, the engineered microorganism can utilize one or more of the following enzymes: (i) acetolactate synthase, (ii) alpha-acetolactate decarboxylase, and/or (iii) acetoin reductase. Acetolactate synthase (encoded by the gene AlsS) converts two molecules of pyruvate into 2-acetolactate. Alpha-acetolactate decarboxylase (encoded by the gene BudA) converts 2-acetolactate into acetoin. Acetoin reductase (encoded by the gene ButA) converts acetoin into 2,3-BDO using NADPH or NADH as a reduced cofactor. Acetoin reductases that use NADPH as a cofactor are referred to as "NADPH-dependent acetoin reductase(s)." Acetoin reductases that use NADH as a cofactor are referred to as "NADH-dependent acetoin reductase(s)." In some cases, when using a vector to express or integrate a gene into a microorganism, the gene encoding the acetolactate synthase can be 5' in relation to any other gene on the vector. In some cases, the gene encoding the acetoin reductase can be 3' in relation to any other gene on a vector. In some cases, the gene encoding the alpha-acetolactate decarboxylase can be neither 5' or 3' in relation to any other gene on a vector (e.g., there is at least one gene that is 5' as well as at least one gene that is 3' of the alpha-acetolactate decarboxylase gene). The order of the genes can be present on the vector prior, during, or after contact with the microorganism. For example, a gene can be 5' in relation to any other gene on the vector prior to contact with the microorganism. After contact with the microorganism, the gene can be inserted into a genomic position of the microorganism where the gene is then 3' in relation to any other gene on a vector or neither 3' or 5' in relation to any other gene on a vector. In some cases, the gene can remain 5' in relation to any other gene. For instance, the vectors can be modified within a microorganism in such a way that the order of the genes can be altered. In some cases, after contact with the microorganism, the gene can be inserted into the vector where the gene is then 3' in relation to any other gene on the vector or neither 3' or 5' in relation to any other gene on the vector. In some cases, the specific order of the genes can be achieved after one or more heterologous gene(s) have been inserted into the genome of the microorganism. For example, different integration vectors can be used in order to achieve a specific gene order within the genome of the microorganism. In some cases, the order of the genes is determined after the heterologous gene has been inserted in the genome of the microorganism.

Described herein are microorganisms used to make 2,3-BDO from a C1 carbon (e.g., methane). In some cases, the microorganism herein can be transformed with a gene encoding one or more of the following enzymes: (i) acetoin reductase (NADPH-dependent and/or NADH-dependent); (ii) alpha-acetolactate decarboxylase; and/or (iii) acetolactate synthase (AlsS). For example, the microorganism can be transformed with a gene encoding a NADPH- or NADH-dependent acetoin reductase. As another example, the microorganism can be transformed with a gene encoding an alpha-acetolactate decarboxylase. As yet another example, the microorganism can be transformed with a gene encoding an acetolactate synthase. These genes can be heterologous to the microorganism. In some cases, these genes can be episomally expressed, integrated into the genome of the microorganism (e.g., through the use of an integration vector), or any combination of thereof. In some cases, the gene encoding the heterologous acetolactate synthase is 5' in relation to any other heterologous gene. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene.

In some cases, the microorganism can be transformed with two or more genes such as those encoding NADPH- and/or NADH-dependent acetoin reductase and alpha-acetolactate decarboxylase. As another example, the microorganism can also be transformed with genes encoding NADPH- or NADH-dependent acetoin reductase and acetolactate synthase. As yet another example, the microorganism can be transformed with genes encoding an alpha-acetolactate decarboxylase and acetolactate synthase. One or more of the genes can be heterologous to the microorganism. In some cases, these genes can be episomally expressed, integrated into the genome of the microorganism, or any combination of thereof.

In some cases, the microorganism can be transformed with at least three or more genes such as those encoding NADPH- and/or NADH-dependent acetoin reductase, alpha-acetolactate decarboxylase, and acetolactate synthase. One or more of the genes can be heterologous to the microorganism. In some cases, these genes can be episomally expressed, integrated into the genome of the microorganism, or any combination of thereof.

The gene encoding the NADPH-dependent acetoin reductase can be from a bacteria (e.g., a gram positive or gram negative bacterium). The bacterium can, for example, be from the genus *Clostridium*, for example, *Clostridium autoethanogenum.*

The NADPH-dependent acetoin reductase can comprise an amino acid sequence that is substantially similar to SEQ ID NO: 9. For example, the NADPH-dependent acetoin reductase can comprise an amino acid sequence that is at least 65%, 70%, 75%, 80%, 85%, 90%, 91%, 92%, 93%, 94%, 95%, 96%, 97%, 98%, or 99% identical to SEQ ID NO: 9. In some cases, the NADPH-dependent acetoin reductase can comprise an amino acid sequence that is at least 60% identical to SEQ ID NO: 9. In some cases, the NADPH-dependent acetoin reductase can comprise an amino acid sequence that is at least 65% identical to SEQ ID NO: 9. In some cases, the NADPH-dependent acetoin reductase can comprise an amino acid sequence that is at least 70% identical to SEQ ID NO: 9. In some cases, the NADPH-dependent acetoin reductase can comprise an amino acid sequence that is at least 75% identical to SEQ ID NO: 9. In some cases, the NADPH-dependent acetoin reductase can comprise an amino acid sequence that is at least 80% identical to SEQ ID NO: 9. In some cases, the NADPH-dependent acetoin reductase can comprise an amino acid sequence that is at least 85% identical to SEQ ID NO: 9. In some cases, the NADPH-dependent acetoin reductase can comprise an amino acid sequence that is at least 90% identical to SEQ ID NO: 9. In some cases, the NADPH-dependent acetoin reductase can comprise an amino acid sequence that is at least 91% identical to SEQ ID NO: 9. In some cases, the NADPH-dependent acetoin reductase can comprise an amino acid sequence that is at least 92% identical to SEQ ID NO: 9. In some cases, the NADPH-dependent acetoin reductase can comprise an amino acid sequence that is at least 93% identical to SEQ ID NO: 9. In some cases, the NADPH-dependent acetoin reductase can comprise an amino acid sequence that is at least 94% identical to SEQ ID NO: 9. In some cases, the NADPH-dependent acetoin reductase can comprise an amino acid sequence that is at least 95% identical to SEQ ID NO: 9. In some cases, the NADPH-dependent acetoin reductase can comprise an amino acid sequence that is at least 96% identical to SEQ ID NO: 9. In some cases, the NADPH-dependent acetoin reductase can comprise an amino acid sequence that is at least 97% identical to SEQ ID NO: 9. In some cases, the NADPH-dependent acetoin reductase can comprise an amino acid sequence that is at least 98% identical to SEQ ID NO: 9. In some cases, the NADPH-dependent acetoin reductase can comprise an amino acid sequence that is at least 99% identical to SEQ ID NO: 9. In some cases, the NADPH-dependent acetoin reductase can comprise an amino acid sequence that is SEQ ID NO: 9. In some cases, the NADPH-dependent acetoin reductase comprise the amino acid sequence SEQ ID NO: 9.

The gene encoding the NADH-dependent acetoin reductase can be from a bacteria (e.g., a gram positive or gram negative bacteria). Examples include those from the genus *Bacillus*, for example *Bacillus subtilis*. The bacteria can be from the genus *Paenibacillus*, for example *Paenibacillus polymyxa.*

In some cases, the NADH-dependent acetoin reductase can comprise an amino acid sequence that is substantially similar to SEQ ID NOs: 11 or 13. For example, the NADH-dependent acetoin reductase can comprises an amino acid sequence that is at least 60%, 65%, 70%, 75%, 80%, 85%, 90%, 91%, 92%, 93%, 94%, 95%, 96%, 97%, 98%, or 99% identical to SEQ ID NOs: 11 or 13. In some cases, the NADH-dependent acetoin reductase can comprise an amino acid sequence that is at least 60% identical to SEQ ID NOs: 11 or 13. In some cases, the NADH-dependent acetoin reductase can comprise an amino acid sequence that is at least 65% identical to SEQ ID NOs: 11 or 13. In some cases, the NADH-dependent acetoin reductase can comprise an amino acid sequence that is at least 70% identical to SEQ ID NOs: 11 or 13. In some cases, the NADH-dependent acetoin reductase can comprise an amino acid sequence that is at least 75% identical to SEQ ID NOs: 11 or 13. In some cases, the NADH-dependent acetoin reductase can comprise an amino acid sequence that is at least 80% identical to SEQ ID NOs: 11 or 13. In some cases, the NADH-dependent acetoin reductase can comprise an amino acid sequence that is at least 85% identical to SEQ ID NOs: 11 or 13. In some cases, the NADH-dependent acetoin reductase can comprise an amino acid sequence that is at least 90% identical to SEQ ID NOs: 11 or 13. In some cases, the NADH-dependent acetoin reductase can comprise an amino acid sequence that is at least 91% identical to SEQ ID NOs: 11 or 13. In some cases, the NADH-dependent acetoin reductase can comprise an amino acid sequence that is at least 92% identical to SEQ ID NOs: 11 or 13. In some cases, the NADH-dependent acetoin reductase can comprise an amino acid sequence that is at least 93% identical to SEQ ID NOs: 11 or 13. In some cases, the NADH-dependent acetoin reductase can comprise an amino acid sequence that is at least 94% identical to SEQ ID NOs: 11 or 13. In some cases, the NADH-dependent acetoin reductase can comprise an amino acid sequence that is at least 95% identical to SEQ ID NOs: 11 or 13. In some cases, the NADH-dependent acetoin reductase can comprise an amino acid sequence that is at least 96% identical to SEQ ID NOs: 11 or 13. In some cases, the NADH-dependent acetoin reductase can comprise an amino acid sequence that is at least 97% identical to SEQ ID NOs: 11 or 13. In some cases, the NADH-dependent acetoin reductase can comprise an amino acid sequence that is at least 98% identical to SEQ ID NOs: 11 or 13. In some cases, the NADH-dependent acetoin reductase can comprise an amino acid sequence that is at least 99% identical to SEQ ID NOs: 11 or 13. In some cases, the NADH-dependent acetoin reductase comprises the amino acid sequence SEQ ID NOs: 11 or 13.

The gene encoding the alpha-acetolactate decarboxylase (budA) can be from a bacterium (e.g., a gram positive bacteria or gram negative bacterium). Examples include those from the genus *Clostridium*, for example *Clostridium autoethanogenum*. Other examples include those from the genus *Klebsiella*, for example *Klebsiella pneumoniae.*

In some cases, the alpha-acetolactate decarboxylase can comprise an amino acid sequence that is substantially similar to SEQ ID NOs: 5 or 7. For example, the alpha-acetolactate decarboxylase can comprise an amino acid sequence that is at least 60% 65%, 70%, 75%, 80%, 85%, 90%, 91%, 92%, 93%, 94%, 95%, 96%, 97%, 98%, or 99% identical to SEQ ID NOs: 5 or 7. In some cases, the alpha-acetolactate decarboxylase can comprise an amino acid sequence that is at least 60% identical to SEQ ID NOs: 5 or 7. For example, the alpha-acetolactate decarboxylase can comprise an amino acid sequence that is at least 65% identical to SEQ ID NOs: 5 or 7. In some cases, the alpha-acetolactate decarboxylase can comprise an amino acid sequence that is at least 70% identical to SEQ ID NOs: 5 or 7. For example, the alpha-acetolactate decarboxylase can comprise an amino acid sequence that is at least 75% identical to SEQ ID NOs: 5 or 7. In some cases, the alpha-acetolactate decarboxylase can comprise an amino acid sequence that is at least 80% identical to SEQ ID NOs: 5 or 7. For example, the alpha-acetolactate decarboxylase can comprise an amino acid sequence that is at least 85% identical to SEQ ID NOs: 5 or 7. In some cases, the alpha-acetolactate decarboxylase can comprise an amino acid sequence that is at least 90% identical to SEQ ID NOs: 5 or 7. In some cases, the alpha-acetolactate decarboxylase can comprise an amino acid sequence that is at least 91% identical to SEQ ID NOs: 5 or 7. In some cases, the alpha-acetolactate decarboxylase can comprise an amino acid sequence that is at least 92% identical to SEQ ID NOs: 5 or 7. In some cases, the alpha-acetolactate decarboxylase can comprise an amino acid sequence that is at least 93% identical to SEQ ID NOs: 5 or 7. In some cases, the alpha-acetolactate decarboxylase can comprise an amino acid sequence that is at least 94% identical to SEQ ID NOs: 5 or 7. In some cases, the alpha-acetolactate decarboxylase can comprise an amino acid sequence that is at least 95% identical to SEQ ID NOs: 5 or 7. In some cases, the alpha-acetolactate decarboxylase can comprise an amino acid sequence that is at least 96% identical to SEQ ID NOs: 5 or 7. In some cases, the alpha-acetolactate decarboxylase can comprise an amino acid sequence that is at least 97% identical to SEQ ID NOs: 5 or 7. In some cases, the alpha-acetolactate decarboxylase can comprise an amino acid sequence that is at least 98% identical to SEQ ID NOs: 5 or 7. In some cases, the alpha-acetolactate decarboxylase can comprise an amino acid sequence that is at least 99% identical to SEQ ID NOs: 5 or 7. In some cases, the alpha-acetolactate decarboxylase can comprise an amino acid sequence that is identical to SEQ ID NOs: 5 or 7. In some cases, the alpha-acetolactate decarboxylase comprises the amino acid sequence SEQ ID NOs: 5 or 7.

The gene encoding the acetolactate synthase (AlsS) can be from a bacterium (e.g., a gram positive bacterium). Examples include those from the genus *Clostridium*, for example *Clostridium autoethanogenum*. Other examples include those from the genus *Bacillus*, for example *Bacillus subtilis*. Additional species examples include *Bacillus licheniformis*.

In some cases, the acetolactate synthase can comprise an amino acid sequence that is substantially similar to anyone of SEQ ID NOs: 1, 3, or 19. In some cases, the acetolactate synthase can comprise an amino acid sequence that is at least 60% 65%, 70%, 75%, 80%, 85%, 90%, 91%, 92%, 93%, 94%, 95%, 96%, 97%, 98%, or 99% identical to anyone of SEQ ID NOs: 1, 3, or 19. In some cases, the acetolactate synthase can comprise an amino acid sequence that is at least 60% identical to anyone of SEQ ID NOs: 1, 3, or 19. In some cases, the acetolactate synthase can comprise an amino acid sequence that is at least 65% identical to anyone of SEQ ID NOs: 1, 3, or 19. In some cases, the acetolactate synthase can comprise an amino acid sequence that is at least 70% identical to anyone of SEQ ID NOs: 1, 3, or 19. In some cases, the acetolactate synthase can comprise an amino acid sequence that is at least 75% identical to anyone of SEQ ID NOs: 1, 3, or 19. In some cases, the acetolactate synthase can comprise an amino acid sequence that is at least 80% identical to anyone of SEQ ID NOs: 1, 3, or 19. In some cases, the acetolactate synthase can comprise an amino acid sequence that is at least 85% identical to anyone of SEQ ID NOs: 1, 3, or 19. In some cases, the acetolactate synthase can comprise an amino acid sequence that is at least 90% identical to anyone of SEQ ID NOs: 1, 3, or 19. In some cases, the acetolactate synthase can comprise an amino acid sequence that is at least 91% identical to anyone of SEQ ID NOs: 1, 3, or 19. In some cases, the acetolactate synthase can comprise an amino acid sequence that is at least 92% identical to anyone of SEQ ID NOs: 1, 3, or 19. In some cases, the acetolactate synthase can comprise an amino acid sequence that is at least 93% identical to anyone of SEQ ID NOs: 1, 3, or 19. In some cases, the acetolactate synthase can comprise an amino acid sequence that is at least 94% identical to anyone of SEQ ID NOs: 1, 3, or 19. In some cases, the acetolactate synthase can comprise an amino acid sequence that is at least 95% identical to anyone of SEQ ID NOs: 1, 3, or 19. In some cases, the acetolactate synthase can comprise an amino acid sequence that is at least 96% identical to anyone of SEQ ID NOs: 1, 3, or 19. In some cases, the acetolactate synthase can comprise an amino acid sequence that is at least 97% identical to anyone of SEQ ID NOs: 1, 3, or 19. In some cases, the acetolactate synthase can comprise an amino acid sequence that is at least 98% identical to anyone of SEQ ID NOs: 1, 3, or 19. In some cases, the acetolactate synthase can comprise an amino acid sequence that is at least 99% identical to anyone of SEQ ID NOs: 1, 3, or 19. In some cases, the acetolactate synthase can comprise an amino acid sequence that is identical to anyone of SEQ ID NOs: 1, 3, or 19.

In some cases, additional enzymes can be provided to the microorganism to yield other desired end products by fermentation.

In some cases, the amino acid sequence can be optimized based on the microorganism in which the genes will be provided or the enzymes will be expressed. In such cases, conservative amino acids substitutions can be made based on whether the microorganism typically uses a specific amino acid or how much of that particular amino acid is available for use within the microorganism.

Vectors

Polynucleotide constructs prepared for introduction into a prokaryotic or eukaryotic host may typically, but not always, comprise a replication system (i.e. vector) recognized by the host. The vector includes the intended polynucleotide fragment encoding the desired polypeptide and, optionally, transcription and translational initiation regulatory sequences operably linked to the polypeptide-encoding segment. Expression systems (such as expression vectors) can include, for example, an origin of replication or autonomously replicating sequence (ARS), expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides can also be included where appropriate, preferably from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995).

Manipulation of polynucleotides that encode the enzymes disclosed herein is typically carried out in recombinant vectors. Vectors which may be employed include bacterial plasmids, bacteriophage, artificial chromosomes, episomal vectors and gene expression vectors. Vectors may be selected to accommodate a polynucleotide encoding a protein of a desired size. Following production of a selected vector, a suitable host cell (e.g., the microorganisms described herein) is transfected or transformed with the vector. Each vector contains various functional components, which generally include a cloning site, an origin of replication and at least one selectable marker gene. A vector may additionally possess one or more of the following elements: an enhancer, promoter, a transcription termination sequence and/or other signal sequences. Such sequence elements may be optimized for the selected host species. Such sequence elements may be positioned in the vicinity of the cloning site, such that they are operatively linked to the gene encoding a preselected enzyme.

Vectors, including cloning and expression vectors, can contain nucleic acid sequences that enable the vector to replicate in one or more selected microorganisms. For example, the sequence can be one that enables the vector to replicate independently of the host chromosomal DNA and can include origins of replication or autonomously replicating sequences. Such sequences are well known for a variety of bacteria, yeast and viruses. For example, the origin of replication from the plasmid pBR322 is suitable for most gram-negative bacteria, the origin of replication for 2 micron plasmid is suitable for yeast, and various viral origins of replication (e.g. SV40, adenovirus) are useful for cloning vectors.

A cloning or expression vector may contain a selection gene, also referred to as a selectable marker. This gene encodes a protein necessary for the survival or growth of transformed microorganisms in a selective culture medium. Microorganisms not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in *E. coli*. An example of a *E. coli*-selectable marker is the β-lactamase gene, which confers resistance to the antibiotic ampicillin. These selectable markers can be obtained from *E. coli* plasmids, such as pBR322 or a pUC plasmid such as pUC18 or pUC19, or pUC119.

The vectors of the present invention can comprise one or more switches, such as an inducible or repressible switch, e.g., an arabinose or lanthanum sensitive switch. The vectors can also comprise one or more different/same promoters.

Promoters

Vectors can contain a promoter that is recognized by the host microorganism. The promoter can be operably linked to a coding sequence of interest. Such a promoter can be inducible or constitutive. Polynucleotides are operably linked when the polynucleotides are in a relationship permitting them to function in their intended manner.

Different promoters can be used to drive the expression of the genes. For example, if temporary gene expression (i.e., non-constitutively expressed) is desired, expression can be driven by inducible promoters.

In some cases, the AlsS gene is expressed temporarily. In other words, the AlsS gene is not constitutively expressed. The expression of the AlsS gene can be driven by inducible or repressible promoters. Examples of inducible or repressible promoters include, but are not limited to, those promoters inducible or repressible by: (a) sugars such as arabinose and lactose (or non metabolizable analogs, e.g., isopropyl β-D-1-thiogalactopyranoside (IPTG)); (b) metals such as lanthanum, copper, calcium; (c) temperature; (d) Nitrogen-source; (e) oxygen; (f) cell state (growth or stationary); (g) metabolites such as phosphate; (h) CRISPRi; (i) jun; (j) fos, (k) metallothionein and/or (l) heat shock. These promoters can be used in a methanotroph system. An example of an inducible promoter that can be used within methanotrophs is a pBAD promoter or a pMxaF promoter.

Inducible or repressible promoters that can be particularly useful are sugar and rare earth metal switches. For example, promoters that are sensitive to the sugar arabinose can be used as an inducible switch. In some cases, arabinose switches can be used to drive expression of one or more genes. For example, in the presence arabinose, the 2,3-BDO producing machinery can be "turned-on." The arabinose switch can turn on the expression of an acetoin reductase. The arabinose switch can also turn on the expression of an alpha-acetolactate decarboxylase (budA). The arabinose switch can also turn on the expression of acetolactate synthase (AlsS).

Other particularly useful switches can be rare earth metal switches, such as lanthanum switches (or cerium, praseodymium, or neodymium switches). In some cases, the rare earth metal (e.g., lanthanum, cerium, praseodymium, or neodymium) switch can be a repressible switch that can be used to repress expression of one or more genes, until the repressor is removed, after which the genes are "turned-on". For example, in the presence the metal lanthanum, the 2,3-BDO producing machinery can be "turned-off." The lanthanum switch can turned off (and expression of the genes induced) by either removing the lanthanum from the media or diluting the lanthanum in the media to levels where its repressible effects are reduced, minimized, or eliminated. In some cases, the rare earth metal (e.g., lanthanum, cerium, praseodymium, or neodymium) switch can control the expression of an NADPH-dependent acetoin reductase. The rare earth metal (e.g., lanthanum, cerium, praseodymium, or neodymium) switch can be used to control the expression of an alpha-acetolactate decarboxylase (budA). Further, the rare earth metal (e.g., lanthanum, cerium, praseodymium, or neodymium) switch can be used to control the expression of an acetolactate synthase (AlsS).

Constitutively expressed promoters can also be used in the vector systems herein. For example, the expression of NADPH- or NADH-dependent acetoin reductase and/or alpha-acetolactate decarboxylase can be controlled by constitutively active promoters. Examples of such promoters include but are not limited to pMxaF and p.Bba.J23111.

Promoters suitable for use with prokaryotic hosts can include, for example, the a-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Promoters for use in bacterial systems will also generally contain a Shine-Dalgarno sequence operably linked to the coding sequence.

Generally, a strong promoter may be employed to provide for high level transcription and expression of the desired product.

One or more promoters of a transcription unit can be an inducible promoter. For example, a GFP can be expressed from a constitutive promoter while an inducible promoter is used to drive transcription of a gene coding for one or more enzymes as disclosed herein and/or the amplifiable selectable marker.

Some vectors may contain prokaryotic sequences that facilitate the propagation of the vector in bacteria. Thus, the vectors may have other components such as an origin of replication (e.g., a nucleic acid sequence that enables the vector to replicate in one or more selected microorganisms), antibiotic resistance genes for selection in bacteria, and/or an amber stop codon which can permit translation to read through the codon. Additional selectable gene(s) may also be incorporated. Generally, in cloning vectors, the origin of replication is one that enables the vector to replicate independently of the host chromosomal DNA, and includes origins of replication or autonomously replicating sequences. Such sequences can include the ColE1 origin of replication in bacteria or other known sequences.

Genes

The vectors described throughout can comprise a nucleic acid sequence of one or more genes encoding: i) acetoin reductase (NADPH-dependent and/or NADH-dependent); ii) alpha-acetolactate decarboxylase; and/or iii) acetolactate synthase (AlsS). For example, the vector can comprise an NADPH- or NADH-dependent acetoin reductase gene. The vector can comprise an alpha-acetolactate decarboxylase gene. The vector can comprise an acetolactate synthase gene. These vectors can also contain one or more regulatory elements (inducible and/or repressible promoters) that control the expression of the genes within the vectors. In some cases, the switches that can be used include, but are not limited to, inducible or repressible switches, e.g., an arabinose or lanthanum switches. These genes can be heterologous to the microorganism in which the vector is contacted with (and eventually transformed with). In some cases, these genes can be in an episomally vector. In some cases, the vector can be one that can be used to integrate one or more into the genome of the microorganism. In some cases, both an episomal vector and an integration vector can be used. In some cases, the gene encoding the heterologous acetolactate synthase is 5' in relation to any other heterologous gene. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene. The order of the genes can be present on the vector prior, during, or after contact with the microorganism. For example, a gene can be 5' in relation to any other gene on the vector prior to contact with the microorganism. After contact with the microorganism, the gene can be inserted into a genomic position of the microorganism where the gene is then 3' in relation to any other gene on a vector or is neither 3' or 5' in relation to any other gene on a vector. In some cases, the gene can remain 5' in relation to any other gene on the vector. For instance, the vectors can be modified within a microorganism in such a way that the order of the genes can be altered. In some cases, after contact with the microorganism, the gene can be inserted into the vector where the gene is then positioned 3' in relation to any other gene on the vector or is positioned as neither 3' or 5' in relation to any other gene on the vector. In some cases, the specific order of the genes can be achieved after one or more heterologous gene(s) have been inserted into the genome of the microorganism. For example, different integration vectors can be used in order to achieve a specific gene order within the genome of the microorganism. In some cases, the order of the genes can be determined after the heterologous gene has been inserted in the genome of the microorganism.

In some cases, the vector can comprise two or more genes encoding: i) acetoin reductase (NADPH-dependent and/or NADH-dependent); ii) alpha-acetolactate decarboxylase; and/or iii) acetolactate synthase (AlsS). For example, the vector can include an NADPH- or NADH-dependent acetoin reductase. In this case, one or more of the genes can be heterologous to the microorganism in which the vector is contacted with (and eventually transformed with). In some cases, these genes can be in an episomally vector. In some cases, the vector can be one that can be used to integrate one or more into the genome of the microorganism. In some cases, these genes can be in an episomally vector as well as in an integration vector. In some cases, the gene encoding the heterologous acetolactate synthase is 5' in relation to any other heterologous gene. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene.

In one case, the vector can comprise at least three or more genes encoding NADPH- and/or NADH-dependent acetoin reductase, alpha-acetolactate decarboxylase, and acetolactate synthase. One or more of the genes can be heterologous to the microorganism in which the vector is contacted with (and eventually transformed with). In some cases, these genes can be in an episomally vector. In some cases, the vector can be one that can be used to integrate one or more into the genome of the microorganism. In some cases, these genes can be in an episomally vector as well as in an integration vector.

In one instance, the acetoin reductase gene is from a bacteria (e.g., a gram positive bacterium). The bacterium can be from the genus *Clostridium*, for example the species *Clostridium autoethanogenum.*

The NADPH-dependent acetoin reductase gene can comprise a nucleotide sequence that is substantially similar to SEQ ID NO: 10. For example, the NADPH-dependent acetoin reductase gene can comprise a nucleotide sequence that is at least 60%, 65%, 70%, 75%, 80%, 85%, 90%, 91%, 92%, 93%, 94%, 95%, 96%, 97%, 98%, or 99% identical to SEQ ID NO: 10. For example, the NADPH-dependent acetoin reductase gene can comprise a nucleotide sequence that is at least 60% identical to SEQ ID NO: 10. In some cases, the NADPH-dependent acetoin reductase gene can comprise a nucleotide sequence that is at least 65% identical to SEQ ID NO: 10. In some cases, the NADPH-dependent acetoin reductase gene can comprise a nucleotide sequence that is at least 70% identical to SEQ ID NO: 10. In some cases, the NADPH-dependent acetoin reductase gene can comprise a nucleotide sequence that is at least 75% identical to SEQ ID NO: 10. In some cases, the NADPH-dependent acetoin reductase gene can comprise a nucleotide sequence that is at least 80% identical to SEQ ID NO: 10. In some cases, the NADPH-dependent acetoin reductase gene can comprise a nucleotide sequence that is at least 85% identical to SEQ ID NO: 10. In some cases, the NADPH-dependent acetoin reductase gene can comprise a nucleotide sequence that is at least 90% identical to SEQ ID NO: 10. In some cases, the NADPH-dependent acetoin reductase gene can comprise a nucleotide sequence that is at least 91% identical to SEQ ID NO: 10. In some cases, the NADPH-dependent acetoin reductase gene can comprise a nucleotide sequence that is at least 92% identical to SEQ ID NO: 10. In some cases, the NADPH-dependent acetoin reductase gene can comprise a nucleotide sequence that is at least 93% identical to SEQ ID NO: 10. In some cases, the NADPH-dependent acetoin reductase gene can comprise a nucleotide sequence that is at least 94% identical to SEQ ID NO: 10. In some cases, the NADPH-dependent acetoin reductase gene can comprise a nucleotide sequence that is at least 95% identical to SEQ ID NO: 10. In some cases, the NADPH-dependent acetoin reductase gene can comprise a nucleotide sequence that is at least 96% identical to SEQ ID NO: 10. In some cases, the NADPH-dependent acetoin reductase gene can comprise a nucleotide sequence that is at least 97% identical to SEQ ID NO: 10. In some cases, the NADPH-dependent acetoin reductase gene can comprise a nucleotide sequence that is at least 98% identical to SEQ ID NO: 10. In some cases, the NADPH-dependent acetoin reductase gene can comprise a nucleotide sequence that is at least 99% identical to SEQ ID NO: 10. In some cases, the NADPH-dependent acetoin reductase gene can comprise a nucleotide sequence that is SEQ ID NO: 10.

When a NADH-dependent acetoin reductase is desired, the NADH-dependent acetoin reductase gene can be from a bacteria (e.g., a gram positive bacterium). Examples of such bacteria include those from the genus *Bacillus*, for example the species *Bacillus subtilis*, and the genus *Paenibacillus*, for example the species *Paenibacillus polymyxa*.

The NADH-dependent acetoin reductase gene can comprise a nucleotide sequence that is substantially similar to SEQ ID NOs: 12 or 14. For example NADH-dependent acetoin reductase gene can comprise a nucleotide sequence that is at least 60%, 65%, 70%, 75%, 80%, 85%, 90%, 91%, 92%, 93%, 94%, 95%, 96%, 97%, 98%, or 99% identical to SEQ ID NOs: 12 or 14. In some cases, the NADH-dependent acetoin reductase gene can comprise a nucleotide sequence that is at least 65% identical to SEQ ID NOs: 12 or 14. In some cases, the NADH-dependent acetoin reductase gene can comprise a nucleotide sequence that is at least 70% identical to SEQ ID NOs: 12 or 14. In some cases, the NADH-dependent acetoin reductase gene can comprise a nucleotide sequence that is at least 75% identical to SEQ ID NOs: 12 or 14. In some cases, the NADH-dependent acetoin reductase gene can comprise a nucleotide sequence that is at least 80% identical to SEQ ID NOs: 12 or 14. In some cases, the NADH-dependent acetoin reductase gene can comprise a nucleotide sequence that is at least 85% identical to SEQ ID NOs: 12 or 14. In some cases, the NADH-dependent acetoin reductase gene can comprise a nucleotide sequence that is at least 90% identical to SEQ ID NOs: 12 or 14. In some cases, the NADH-dependent acetoin reductase gene can comprise a nucleotide sequence that is at least 91% identical to SEQ ID NOs: 12 or 14. In some cases, the NADH-dependent acetoin reductase gene can comprise a nucleotide sequence that is at least 92% identical to SEQ ID NOs: 12 or 14. In some cases, the NADH-dependent acetoin reductase gene can comprise a nucleotide sequence that is at least 93% identical to SEQ ID NOs: 12 or 14. In some cases, the NADH-dependent acetoin reductase gene can comprise a nucleotide sequence that is at least 94% identical to SEQ ID NOs: 12 or 14. In some cases, the NADH-dependent acetoin reductase gene can comprise a nucleotide sequence that is at least 95% identical to SEQ ID NOs: 12 or 14. In some cases, the NADH-dependent acetoin reductase gene can comprise a nucleotide sequence that is at least 96% identical to SEQ ID NOs: 12 or 14. In some cases, the NADH-dependent acetoin reductase gene can comprise a nucleotide sequence that is at least 97% identical to SEQ ID NOs: 12 or 14. In some cases, the NADH-dependent acetoin reductase gene can comprise a nucleotide sequence that is at least 98% identical to SEQ ID NOs: 12 or 14. In some cases, the NADH-dependent acetoin reductase gene can comprise a nucleotide sequence that is at least 99% identical to SEQ ID NOs: 12 or 14. In some cases, the NADH-dependent acetoin reductase gene can comprise a nucleotide sequence that is identical to SEQ ID NOs: 12 or 14.

When an alpha-acetolactate decarboxylase (budA) is desired, the alpha-acetolactate decarboxylase gene can be from a bacterium. Examples of such bacterium include those from the genus *Clostridium*, for example the species *Clostridium autoethanogenum*, and those from the genus *Klebsiella*, for example the species *Klebsiella pneumoniae*. The alpha-acetolactate decarboxylase gene can be from a gram positive or gram negative bacterium.

The alpha-acetolactate decarboxylase gene can comprise a nucleotide sequence that is substantially similar to SEQ ID NOs: 6 or 8. For example, the alpha-acetolactate decarboxylase gene can comprise a nucleotide sequence that is at least 60%, 65%, 70%, 75%, 80%, 85%, 90%, 91%, 92%, 93%, 94%, 95%, 96%, 97%, 98%, or 99% identical to SEQ ID NOs: 6 or 8. In some cases, the alpha-acetolactate decarboxylase gene can comprise a nucleotide sequence that is at least 60% identical to SEQ ID NOs: 6 or 8. In some cases, the alpha-acetolactate decarboxylase gene can comprise a nucleotide sequence that is at least 65% identical to SEQ ID NOs: 6 or 8. In some cases, the alpha-acetolactate decarboxylase gene can comprise a nucleotide sequence that is at least 70% identical to SEQ ID NOs: 6 or 8. In some cases, the alpha-acetolactate decarboxylase gene can comprise a nucleotide sequence that is at least 75% identical to SEQ ID NOs: 6 or 8. In some cases, the alpha-acetolactate decarboxylase gene can comprise a nucleotide sequence that is at least 80% identical to SEQ ID NOs: 6 or 8. In some cases, the alpha-acetolactate decarboxylase gene can comprise a nucleotide sequence that is at least 85% identical to SEQ ID NOs: 6 or 8. In some cases, the alpha-acetolactate decarboxylase gene can comprise a nucleotide sequence that is at least 90% identical to SEQ ID NOs: 6 or 8. In some cases, the alpha-acetolactate decarboxylase gene can comprise a nucleotide sequence that is at least 91% identical to SEQ ID NOs: 6 or 8. In some cases, the alpha-acetolactate decarboxylase gene can comprise a nucleotide sequence that is at least 92% identical to SEQ ID NOs: 6 or 8. In some cases, the alpha-acetolactate decarboxylase gene can comprise a nucleotide sequence that is at least 93% identical to SEQ ID NOs: 6 or 8. In some cases, the alpha-acetolactate decarboxylase gene can comprise a nucleotide sequence that is at least 94% identical to SEQ ID NOs: 6 or 8. In some cases, the alpha-acetolactate decarboxylase gene can comprise a nucleotide sequence that is at least 95% identical to SEQ ID NOs: 6 or 8. In some cases, the alpha-acetolactate decarboxylase gene can comprise a nucleotide sequence that is at least 96% identical to SEQ ID NOs: 6 or 8. In some cases, the alpha-acetolactate decarboxylase gene can comprise a nucleotide sequence that is at least 97% identical to SEQ ID NOs: 6 or 8. In some cases, the alpha-acetolactate decarboxylase gene can comprise a nucleotide sequence that is at least 98% identical to SEQ ID NOs: 6 or 8. In some cases, the alpha-acetolactate decarboxylase gene can comprise a nucleotide sequence that is at least 99% identical to SEQ ID NOs: 6 or 8. In some cases, the alpha-acetolactate decarboxylase gene can comprise a nucleotide sequence that is identical to SEQ ID NOs: 6 or 8.

When an acetolactate synthase (AlsS) is desired, the acetolactate synthase can be from a bacterium (e.g., a gram positive bacterium). Examples of such bacterium include those from the genus *Clostridium*, for example the species *Clostridium autoethanogenum*, and those from the genus *Bacillus*, for example the species *Bacillus subtilis*. Additional species examples include *Bacillus licheniformis*.

The acetolactate synthase gene can comprise a nucleotide sequence that is substantially similar to any one of SEQ ID NOs: 2, 4, or 20. For example, the acetolactate synthase gene can comprise a nucleotide sequence that is at least 60%, 65%, 70%, 75%, 80%, 85%, 90%, 91%, 92%, 93%, 94%, 95%, 96%, 97%, 98%, or 99% identical to any one of SEQ ID NOs: 2, 4, or 20. The acetolactate synthase gene can comprise a nucleotide sequence that is substantially similar to any one of SEQ ID NOs: 2, 4, or 20. For example, the acetolactate synthase gene can comprise a nucleotide sequence that is at least 60% identical to any one of SEQ ID NOs: 2, 4, or 20. In some cases, the acetolactate synthase gene can comprise a nucleotide sequence that is at least 65% identical to any one of SEQ ID NOs: 2, 4, or 20. In some cases, the acetolactate synthase gene can comprise a nucleotide sequence that is at least 70% identical to any one of SEQ ID NOs: 2, 4, or 20. In some cases, the acetolactate synthase gene can comprise a nucleotide sequence that is at least 75% identical to any one of SEQ ID NOs: 2, 4, or 20. In some cases, the acetolactate synthase gene can comprise a nucleotide sequence that is at least 80% identical to any one of SEQ ID NOs: 2, 4, or 20. In some cases, the acetolactate synthase gene can comprise a nucleotide sequence that is at least 85% identical to any one of SEQ ID NOs: 2, 4, or 20. In some cases, the acetolactate synthase gene can comprise a nucleotide sequence that is at least 90% identical to any one of SEQ ID NOs: 2, 4, or 20. In some cases, the acetolactate synthase gene can comprise a nucleotide sequence that is at least 91% identical to any one of SEQ ID NOs: 2, 4, or 20. In some cases, the acetolactate synthase gene can comprise a nucleotide sequence that is at least 92% identical to any one of SEQ ID NOs: 2, 4, or 20. In some cases, the acetolactate synthase gene can comprise a nucleotide sequence that is at least 93% identical to any one of SEQ ID NOs: 2, 4, or 20. In some cases, the acetolactate synthase gene can comprise a nucleotide sequence that is at least 94% identical to any one of SEQ ID NOs: 2, 4, or 20. In some cases, the acetolactate synthase gene can comprise a nucleotide sequence that is at least 95% identical to any one of SEQ ID NOs: 2, 4, or 20. In some cases, the acetolactate synthase gene can comprise a nucleotide sequence that is at least 96% identical to any one of SEQ ID NOs: 2, 4, or 20. In some cases, the acetolactate synthase gene can comprise a nucleotide sequence that is at least 97% identical to any one of SEQ ID NOs: 2, 4, or 20. In some cases, the acetolactate synthase gene can comprise a nucleotide sequence that is at least 98% identical to any one of SEQ ID NOs: 2, 4, or 20. In some cases, the acetolactate synthase gene can comprise a nucleotide sequence that is at least 99% identical to any one of SEQ ID NOs: 2, 4, or 20. In some cases, the acetolactate synthase gene can comprise a nucleotide sequence that is identical to any one of SEQ ID NOs: 2, 4, or 20.

Additional genes can be placed inside the microorganism in order to make other desired end products by fermentation.

The nucleotide sequence (or more specifically the codons that are encoded by the nucleotide sequences) can be optimized based on the microorganism in which the nucleotide sequences will be expressed. The nucleotide sequences can be codon optimized based on the amount of tRNA available within each individual microorganism. In other words, conservative codon substitutions can be made based on whether the respective microorganism typically uses a specific codon or how much of a particular tRNA is available within the microorganism.

Gene Copy Number

Any of the genes disclosed throughout can have one or more copies of the genes (whether integrated, episomally expressed, or both). For example, each of the acetoin reductase (NADPH-dependent and/or NADH-dependent); ii) alpha-acetolactate decarboxylase; and/or iii) acetolactate synthase (AlsS) can have 1, 2, 3, 4, 5, 6, 7, 8, 9, 10, 11, 12, 13, 14, 15, 16, 17, 18, 19, 20, 21, 22, 23, 24, 25, or more copies of the genes. In some cases, the gene copy number is 1. In some cases, the gene copy number is 2. In some cases, the gene copy number is 3. In some cases, the gene copy number is 4. In some cases, the gene copy number is 5. In some cases, the gene copy number is 6. In some cases, the gene copy number is 7. In some cases, the gene copy number is 8. In some cases, the gene copy number is 9. In some cases, the gene copy number is 10. In some cases, the gene copy number is 11. In some cases, the gene copy number is 12. In some cases, the gene copy number is 13. In some cases, the gene copy number is 14. In some cases, the gene copy number is 15. In some cases, the gene copy number is 16. In some cases, the gene copy number is 17. In some cases, the gene copy number is 18. In some cases, the gene copy number is 19. In some cases, the gene copy number is 20. In some cases, the gene copy number is 21. In some cases, the gene copy number is 22. In some cases, the gene copy number is 23. In some cases, the gene copy number is 24. In some cases, the gene copy number is 25. Typically, the gene copy number is under 25 copies, however, in some cases, it can be more. Therefore, in some cases, the gene copy number is more than 25.

Further, any of genes described throughout (e.g., acetoin reductase; alpha-acetolactate decarboxylase; and/or acetolactate synthase) can have the same number of copies of genes. For example, the gene encoding acetolactate synthase can have 1 to 25 copies, the gene encoding alpha-acetolactate decarboxylase can have 1 to 25 copies, and the gene encoding acetoin reductase can have 1 to 25 copies, where all the genes are present in the same number. In some cases, any of the genes described throughout can have different number of copies of genes. For example, the gene encoding acetolactate synthase can have 1 to 25 copies, the gene encoding alpha-acetolactate decarboxylase can have 1 to 25 copies, and the gene encoding acetoin reductase can have 1 to 25 copies, where all the genes are present in different numbers. In one particular example, the gene encoding an acetolactate synthase can have 5 to 10 copies, while the gene encoding acetoin reductase can have 1 to 6 copies, while the gene encoding an alpha-acetolactate decarboxylase can have 3 to 8 copies. Again, typically the gene copy number is under 25 copies of any given gene. However, in some cases it can be more.

Any number of the genes can be expressed in an integration vector, episomal vector, or both. In regards to the example above, the gene encoding an acetolactate synthase can have 5 to 10 copies, where 2 to 5 can be integrated and 3 to 5 copies can be expressed in the episomal vector. In regards to the example above, the gene encoding an acetoin reductase decarboxylase can have 1 to 6 copies, where 1 to 4 copies can be integrated and 0 to 1 copies can be expressed in the episomal vector. In regards to the example above, the gene encoding an alpha-acetolactate decarboxylase can have 3 to 8 copies, where 2 to 6 copies can be integrated and 1 to 2 copies can be expressed in the episomal vector.

In some cases, a gene copy can include a partial sequence of the full gene. In some cases, the partial sequence of the full gene can include the active site of the enzyme encoded by the gene. Any combination of the full gene and partial sequence of the gene is contemplated. For example, there can be 4 copies of the full gene and 2 copies of the partial sequence of the gene. This can be considered 6 copies of the gene.

Isolated Nucleic Acids

The genes described herein can be in the form of an isolated polynucleic acid. In other words, the genes can be in forms that do not exist in nature, isolated from a chromosome. The isolated polynucleic acids can comprise a nucleic acid sequence of one or more genes encoding: i) acetoin reductase (NADPH-dependent and/or NADH-dependent); ii) alpha-acetolactate decarboxylase; and/or iii)

acetolactate synthase (AlsS). For example, the isolated polynucleic acid can comprise an NADPH-dependent and/or NADH-dependent acetoin reductase gene. The isolated polynucleic acid can comprise an alpha-acetolactate decarboxylase gene. The isolated polynucleic acid can comprise an acetolactate synthase gene.

In some cases, the isolated polynucleic acid can comprise a nucleotide sequence that can encode a NADPH-dependent acetoin reductase gene. For example, the isolated polynucleic acid can comprise a nucleotide sequence that is substantially similar to SEQ ID NO: 10. In some cases, the isolated polynucleic acid can comprises a nucleotide sequence that is at least 60%, 65%, 70%, 75%, 80%, 85%, 90%, 91%, 92%, 93%, 94%, 95%, 96%, 97%, 98%, or 99% identical to SEQ ID NO: 10. In some cases, the isolated polynucleic acid can comprise a nucleotide sequence that is at least 60% identical to SEQ ID NO: 10. In some cases, the isolated polynucleic acid can comprise a nucleotide sequence that is at least 65% identical to SEQ ID NO: 10. In some cases, the isolated polynucleic acid can comprise a nucleotide sequence that is at least 70% identical to SEQ ID NO: 10. In some cases, the isolated polynucleic acid can comprise a nucleotide sequence that is at least 75% identical to SEQ ID NO: 10. In some cases, the isolated polynucleic acid can comprise a nucleotide sequence that is at least 80% identical to SEQ ID NO: 10. In some cases, the isolated polynucleic acid can comprise a nucleotide sequence that is at least 81% identical to SEQ ID NO: 10. In some cases, the isolated polynucleic acid can comprise a nucleotide sequence that is at least 82% identical to SEQ ID NO: 10. In some cases, the isolated polynucleic acid can comprise a nucleotide sequence that is at least 83% identical to SEQ ID NO: 10. In some cases, the isolated polynucleic acid can comprise a nucleotide sequence that is at least 84% identical to SEQ ID NO: 10. In some cases, the isolated polynucleic acid can comprise a nucleotide sequence that is at least 85% identical to SEQ ID NO: 10. In some cases, the isolated polynucleic acid can comprise a nucleotide sequence that is at least 86% identical to SEQ ID NO: 10. In some cases, the isolated polynucleic acid can comprise a nucleotide sequence that is at least 87% identical to SEQ ID NO: 10. In some cases, the isolated polynucleic acid can comprise a nucleotide sequence that is at least 88% identical to SEQ ID NO: 10. In some cases, the isolated polynucleic acid can comprise a nucleotide sequence that is at least 89% identical to SEQ ID NO: 10. In some cases, the isolated polynucleic acid can comprise a nucleotide sequence that is at least 90% identical to SEQ ID NO: 10. In some cases, the isolated polynucleic acid can comprise a nucleotide sequence that is at least 91% identical to SEQ ID NO: 10. In some cases, the isolated polynucleic acid can comprise a nucleotide sequence that is at least 92% identical to SEQ ID NO: 10. In some cases, the isolated polynucleic acid can comprise a nucleotide sequence that is at least 93% identical to SEQ ID NO: 10. In some cases, the isolated polynucleic acid can comprise a nucleotide sequence that is at least 94% identical to SEQ ID NO: 10. In some cases, the isolated polynucleic acid can comprise a nucleotide sequence that is at least 95% identical to SEQ ID NO: 10. In some cases, the isolated polynucleic acid can comprise a nucleotide sequence that is at least 96% identical to SEQ ID NO: 10. In some cases, the isolated polynucleic acid can comprise a nucleotide sequence that is at least 97% identical to SEQ ID NO: 10. In some cases, the isolated polynucleic acid can comprise a nucleotide sequence that is at least 98% identical to SEQ ID NO: 10. In some cases, the isolated polynucleic acid can comprise a nucleotide sequence that is at least 99% identical to SEQ ID NO: 10. In some cases, the isolated polynucleic acid can comprise a nucleotide sequence that is SEQ ID NO: 10.

In some cases, the isolated polynucleic acid can comprise a nucleotide sequence that can encode a NADH-dependent acetoin reductase. For example, the isolated polynucleic acid can comprise a nucleotide sequence that is substantially similar to SEQ ID NOs: 12 or 14. In some cases, the isolated polynucleic acid can comprise a nucleotide sequence that is at least 60%, 65%, 70%, 75%, 80%, 85%, 90%, 91%, 92%, 93%, 94%, 95%, 96%, 97%, 98%, or 99% identical to SEQ ID NOs: 12 or 14. In some cases, the isolated polynucleic acid can encode for an NADH-dependent acetoin reductase. For example, the isolated polynucleic acid can comprise a nucleotide sequence that is substantially similar to SEQ ID NOs: 12 or 14. In some cases, the isolated polynucleic acid can comprise a nucleotide sequence that is at least 60% identical to SEQ ID NOs: 12 or 14. In some cases, the isolated polynucleic acid can comprise a nucleotide sequence that is at least 65% identical to SEQ ID NOs: 12 or 14. In some cases, the isolated polynucleic acid can comprise a nucleotide sequence that is at least 70% identical to SEQ ID NOs: 12 or 14. In some cases, the isolated polynucleic acid can comprise a nucleotide sequence that is at least 75% identical to SEQ ID NOs: 12 or 14. In some cases, the isolated polynucleic acid can comprise a nucleotide sequence that is at least 80% identical to SEQ ID NOs: 12 or 14. In some cases, the isolated polynucleic acid can comprise a nucleotide sequence that is at least 81% identical to SEQ ID NOs: 12 or 14. In some cases, the isolated polynucleic acid can comprise a nucleotide sequence that is at least 82% identical to SEQ ID NOs: 12 or 14. In some cases, the isolated polynucleic acid can comprise a nucleotide sequence that is at least 83% identical to SEQ ID NOs: 12 or 14. In some cases, the isolated polynucleic acid can comprise a nucleotide sequence that is at least 84% identical to SEQ ID NOs: 12 or 14. In some cases, the isolated polynucleic acid can comprise a nucleotide sequence that is at least 85% identical to SEQ ID NOs: 12 or 14. In some cases, the isolated polynucleic acid can comprise a nucleotide sequence that is at least 86% identical to SEQ ID NOs: 12 or 14. In some cases, the isolated polynucleic acid can comprise a nucleotide sequence that is at least 87% identical to SEQ ID NOs: 12 or 14. In some cases, the isolated polynucleic acid can comprise a nucleotide sequence that is at least 88% identical to SEQ ID NOs: 12 or 14. In some cases, the isolated polynucleic acid can comprise a nucleotide sequence that is at least 89% identical to SEQ ID NOs: 12 or 14. In some cases, the isolated polynucleic acid can comprise a nucleotide sequence that is at least 90% identical to SEQ ID NOs: 12 or 14. In some cases, the isolated polynucleic acid can comprise a nucleotide sequence that is at least 91% identical to SEQ ID NOs: 12 or 14. In some cases, the isolated polynucleic acid can comprise a nucleotide sequence that is at least 92% identical to SEQ ID NOs: 12 or 14. In some cases, the isolated polynucleic acid can comprise a nucleotide sequence that is at least 93% identical to SEQ ID NOs: 12 or 14. In some cases, the isolated polynucleic acid can comprise a nucleotide sequence that is at least 94% identical to SEQ ID NOs: 12 or 14. In some cases, the isolated polynucleic acid can comprise a nucleotide sequence that is at least 95% identical to SEQ ID NOs: 12 or 14. In some cases, the isolated polynucleic acid can comprise a nucleotide sequence that is at least 96% identical to SEQ ID NOs: 12 or 14. In some cases, the isolated polynucleic acid can comprise a nucleotide sequence that is at least 97% identical to SEQ ID NOs: 12 or 14. In some cases, the isolated polynucleic acid can comprise a nucleotide sequence that is at least 98% identical to SEQ ID NOs: 12 or 14. In some cases, the isolated polynucleic acid can comprise a nucleotide sequence that is at least 99% identical to SEQ ID NOs: 12 or 14. In some cases, the isolated polynucleic acid can comprise a nucleotide sequence that is identical to SEQ ID NOs: 12 or 14

In some cases, the isolated polynucleic acid can comprise a nucleotide sequence that encodes for an alpha-acetolactate decarboxylase. In some cases, the isolated polynucleic acid can comprise a nucleotide sequence that is substantially similar to SEQ ID NOs: 6 or 8. For example, the isolated polynucleic acid can comprise a nucleotide sequence that is at least 60%, 65%, 70%, 75%, 80%, 85%, 90%, 91%, 92%, 93%, 94%, 95%, 96%, 97%, 98%, or 99% identical to SEQ ID NOs: 6 or 8. For example, the isolated polynucleic acid can comprise a nucleotide sequence that is at least 60% identical to SEQ ID NOs: 6 or 8. In some cases, the isolated polynucleic acid can comprise a nucleotide sequence that is at least 65% identical to SEQ ID NOs: 6 or 8. In some cases, the isolated polynucleic acid can comprise a nucleotide sequence that is at least 70% identical to SEQ ID NOs: 6 or 8. In some cases, the isolated polynucleic acid can comprise a nucleotide sequence that is at least 75% identical to SEQ ID NOs: 6 or 8. In some cases, the isolated polynucleic acid can comprise a nucleotide sequence that is at least 80% identical to SEQ ID NOs: 6 or 8. In some cases, the isolated polynucleic acid can comprise a nucleotide sequence that is at least 81% identical to SEQ ID NOs: 6 or 8. In some cases, the isolated polynucleic acid can comprise a nucleotide sequence that is at least 82% identical to SEQ ID NOs: 6 or 8. In some cases, the isolated polynucleic acid can comprise a nucleotide sequence that is at least 83% identical to SEQ ID NOs: 6 or 8. In some cases, the isolated polynucleic acid can comprise a nucleotide sequence that is at least 84% identical to SEQ ID NOs: 6 or 8. In some cases, the isolated polynucleic acid can comprise a nucleotide sequence that is at least 85% identical to SEQ ID NOs: 6 or 8. In some cases, the isolated polynucleic acid can comprise a nucleotide sequence that is at least 86% identical to SEQ ID NOs: 6 or 8. In some cases, the isolated polynucleic acid can comprise a nucleotide sequence that is at least 87% identical to SEQ ID NOs: 6 or 8. In some cases, the isolated polynucleic acid can comprise a nucleotide sequence that is at least 88% identical to SEQ ID NOs: 6 or 8. In some cases, the isolated polynucleic acid can comprise a nucleotide sequence that is at least 89% identical to SEQ ID NOs: 6 or 8. In some cases, the isolated polynucleic acid can comprise a nucleotide sequence that is at least 90% identical to SEQ ID NOs: 6 or 8. In some cases, the isolated polynucleic acid can comprise a nucleotide sequence that is at least 91% identical to SEQ ID NOs: 6 or 8. In some cases, the isolated polynucleic acid can comprise a nucleotide sequence that is at least 92% identical to SEQ ID NOs: 6 or 8. In some cases, the isolated polynucleic acid can comprise a nucleotide sequence that is at least 93% identical to SEQ ID NOs: 6 or 8. In some cases, the isolated polynucleic acid can comprise a nucleotide sequence that is at least 94% identical to SEQ ID NOs: 6 or 8. In some cases, the isolated polynucleic acid can comprise a nucleotide sequence that is at least 95% identical to SEQ ID NOs: 6 or 8. In some cases, the isolated polynucleic acid can comprise a nucleotide sequence that is at least 96% identical to SEQ ID NOs: 6 or 8. In some cases, the isolated polynucleic acid can comprise a nucleotide sequence that is at least 97% identical to SEQ ID NOs: 6 or 8. In some cases, the isolated polynucleic acid can comprise a nucleotide sequence that is at least 98% identical to SEQ ID NOs: 6 or 8. In some cases, the isolated polynucleic acid can comprise a nucleotide sequence that is at least 99% identical to SEQ ID NOs: 6 or 8. In some cases, the isolated polynucleic acid can comprise a nucleotide sequence that is identical to SEQ ID NOs: 6 or 8

In some cases, the isolated polynucleic acid can comprise a nucleotide sequence that encodes an acetolactate synthase. In some cases, the isolated polynucleic acid can comprise a nucleotide sequence that is substantially similar to any one of SEQ ID NOs: 2, 4, or 20. For example, the isolated polynucleic acid can comprise a nucleotide sequence that is at least 60%, 65%, 70%, 75%, 80%, 85%, 90%, 91%, 92%, 93%, 94%, 95%, 96%, 97%, 98%, or 99% identical to any one of SEQ ID NOs: 2, 4, or 20. The isolated polynucleic acid can comprise a nucleotide sequence that is at least 60% identical to any one of SEQ ID NOs: 2, 4, or 20. In some cases, the isolated polynucleic acid can comprise a nucleotide sequence that is at least 65% identical to any one of SEQ ID NOs: 2, 4, or 20. In some cases, the isolated polynucleic acid can comprise a nucleotide sequence that is at least 70% identical to any one of SEQ ID NOs: 2, 4, or 20. In some cases, the isolated polynucleic acid can comprise a nucleotide sequence that is at least 75% identical to any one of SEQ ID NOs: 2, 4, or 20. In some cases, the isolated polynucleic acid can comprise a nucleotide sequence that is at least 80% identical to any one of SEQ ID NOs: 2, 4, or 20. In some cases, the isolated polynucleic acid can comprise a nucleotide sequence that is at least 81% identical to any one of SEQ ID NOs: 2, 4, or 20. In some cases, the isolated polynucleic acid can comprise a nucleotide sequence that is at least 82% identical to any one of SEQ ID NOs: 2, 4, or 20. In some cases, the isolated polynucleic acid can comprise a nucleotide sequence that is at least 83% identical to any one of SEQ ID NOs: 2, 4, or 20. In some cases, the isolated polynucleic acid can comprise a nucleotide sequence that is at least 84% identical to any one of SEQ ID NOs: 2, 4, or 20. In some cases, the isolated polynucleic acid can comprise a nucleotide sequence that is at least 85% identical to any one of SEQ ID NOs: 2, 4, or 20. In some cases, the isolated polynucleic acid can comprise a nucleotide sequence that is at least 86% identical to any one of SEQ ID NOs: 2, 4, or 20. In some cases, the isolated polynucleic acid can comprise a nucleotide sequence that is at least 87% identical to any one of SEQ ID NOs: 2, 4, or 20. In some cases, the isolated polynucleic acid can comprise a nucleotide sequence that is at least 88% identical to any one of SEQ ID NOs: 2, 4, or 20. In some cases, the isolated polynucleic acid can comprise a nucleotide sequence that is at least 89% identical to any one of SEQ ID NOs: 2, 4, or 20. In some cases, the isolated polynucleic acid can comprise a nucleotide sequence that is at least 90% identical to any one of SEQ ID NOs: 2, 4, or 20. In some cases, the isolated polynucleic acid can comprise a nucleotide sequence that is at least 91% identical to any one of SEQ ID NOs: 2, 4, or 20. In some cases, the isolated polynucleic acid can comprise a nucleotide sequence that is at least 92% identical to any one of SEQ ID NOs: 2, 4, or 20. In some cases, the isolated polynucleic acid can comprise a nucleotide sequence that is at least 93% identical to any one of SEQ ID NOs: 2, 4, or 20. In some cases, the isolated polynucleic acid can comprise a nucleotide sequence that is at least 94% identical to any one of SEQ ID NOs: 2, 4, or 20. In some cases, the isolated polynucleic acid can comprise a nucleotide sequence that is at least 95% identical to any one of SEQ ID NOs: 2, 4, or 20. In some cases, the isolated polynucleic acid can comprise a nucleotide sequence that is at least 96% identical to any one of SEQ ID NOs: 2, 4, or 20. In some cases, the isolated polynucleic acid can comprise a nucleotide sequence that is at least 97% identical to any one of SEQ ID NOs: 2, 4, or 20. In some cases, the isolated polynucleic acid can comprise a nucleotide sequence that is at least 98% identical to any one of SEQ ID NOs: 2, 4, or 20. In some cases, the isolated polynucleic acid can comprise a nucleotide sequence that is at least 99% identical to any one of SEQ ID NOs: 2, 4, or 20. In some cases, the isolated polynucleic acid can comprise a nucleotide sequence that is identical to any one of SEQ ID NOs: 2, 4, or 20.

Exemplary Vector Sequences

Disclosed herein are also vectors. These vectors can be integrated into various microorganisms, such as methanotrophs are disclosed herein (e.g., any one of SEQ ID NOs: 15 to 18). In some cases, these vectors can be episomally expressed. In some cases, these vectors can be both integrated and episomally expressed. In some cases, minor changes can be made to the vectors without significant changes in the effectiveness of the vectors or the amount of enzymes the vectors are able to produce. Thus, the vectors can be substantially similar to any one of SEQ ID NOs: 15 to 18.

In some cases, the expression cassette of SEQ ID NO: 15 or a sequence that is substantially similar thereto, can be contacted with (and inserted into) a microorganism. This expression cassette comprises a pBAD promoter; a g.Bsu AlsS gene (which includes an initiator ATG and a terminator TAA); a ribosomal binding site rbsGTW001; a g.Kpn BudA gene (which includes an initiator ATG and a terminator TGA); a terminator rrnB; a pmxaF promoter; g.Cau ButA gene (which includes an initiator ATG and a terminator TGA) and a terminator lambda TO. Once a microorganism (such as a methanotroph) is transformed with this expression cassette, the microorganism is referred to as strain XZ58. In some cases, the g.Bsu AlsS gene can be substituted for g.Blic_AlsS gene (e.g., SEQ ID NO: 20).

In some cases, the expression cassette of SEQ ID NO: 16 or a sequence that is substantially similar, can be contacted with (and inserted into) a microorganism. This expression cassette comprises a pBAD promoter; a g.Bsu AlsS gene (which includes an initiator ATG and a terminator TAA); a ribosomal binding site rbsGTW001; a g.Kpn BudA gene (which includes an initiator ATG and a terminator TGA); a terminator rrnB; a pmxaF promoter; g.Bsu ButA gene (which includes an initiator ATG and a terminator TGA) and a terminator lambda TO. Once a microorganism (such as a methanotroph) is transformed with this expression cassette, the microorganism is referred to as strain XZ59. In some cases, the g.Bsu AlsS gene can be substituted for g.Blic_AlsS gene (e.g., SEQ ID NO: 20).

In some cases, the expression cassette of SEQ ID NO: 17 or a sequence that is substantially similar, can be contacted with (and inserted into) a microorganism. This expression cassette comprises a pBAD promoter; a g.Bsu AlsS gene (which includes an initiator ATG and a terminator TAA); a ribosomal binding site rbsGTW001; a g.Kpn BudA gene (which includes an initiator ATG and a terminator TGA); an additional ribosomal binding site rbsGTW001; a terminator rrnB; a pmxaF promoter; g.Cau ButA gene (which includes an initiator ATG and a terminator TGA) and a terminator rrnB. Once a microorganism (such as a methanotroph) is transformed with this expression cassette, the microorganism is referred to as strain XZ06. In some cases, the g.Bsu AlsS gene can be substituted for g.Blic_AlsS gene (e.g., SEQ ID NO: 20).

In some cases, the expression cassette of SEQ ID NO: 18 or a sequence that is substantially similar, can be contacted with (and inserted into) a microorganism. This expression cassette comprises a pBAD promoter; a g.Bsu AlsS gene (which includes an initiator ATG and a terminator TAA); a ribosomal binding site rbsGTW001; a g.Kpn BudA gene (which includes an initiator ATG and a terminator TGA); an additional ribosomal binding site rbsGTW001; a terminator rrnB; a pmxaF promoter; g.Bsu ButA gene (which includes an initiator ATG and a terminator TGA) and a terminator rrnB. Once a microorganism (such as a methanotroph) is transformed with this expression cassette, the microorganism is referred to as strain XZ08. In some cases, the g.Bsu AlsS gene can be substituted for g.Blic_AlsS gene (e.g., SEQ ID NO: 20).

III. Method of Making Genetically Modified Microorganisms

The genetically modified microorganisms disclosed throughout can be made by a variety of ways. A microorganism may be modified (e.g., genetically engineered) by any method to comprise and/or express one or more polynucleotides encoding for enzymes in a pathway that catalyze a conversion of a fermentable carbon source (e.g., a C1 carbon) to one or more intermediates in a pathway for the production of 2,3-BDO, MEK, and/or butadiene. Such enzymes may include acetolactate synthase, alpha-acetolactate decarboxylase, and acetoin reductase. For example, one or more of any of the genes above can be inserted into a microorganism. The genes can be inserted by an expression vector. The genes can also be under the control of one or more different/same promoters or the one or more genes can be under the control of a switch, such as an inducible or repressible promoter, e.g., an arabinose or lanthanum sensitive switch. The genes can also be stably integrated into the genome of the microorganism. In some cases, the genes can be expressed in an episomally vector. In some cases, the genes can be integrated into the genome of the microorganism. In some cases, these genes can be expressed in an episomally vector as well as integrated into the genome of the microorganism. In some cases, the gene encoding the acetolactate synthase is 5' in relation to any other gene on the vector. In some cases, the gene encoding the acetoin reductase is 3' in relation to any other gene on the vector. In some cases, the gene encoding the alpha-acetolactate decarboxylase is neither 5' or 3' in relation to any other gene on the vector. The order of the genes can be present on the vector prior, during, or after contact with the microorganism. For example, a gene can be 5' in relation to any other gene on the vector prior to contact with the microorganism. However, after contact with the microorganism, the gene can be inserted into a position or another gene can be inserted into the vector where the gene is then neither 5' or 3' in relation to any other gene on the vector. For instance, the vectors can be modified within a microorganism in such a way that the order of the genes can be altered. In some cases, the specific order of the genes can be achieved after one or more heterologous gene(s) have been inserted into the genome of the microorganism. For example, different integration vectors can be used in order to achieve a specific gene order within the genome of the microorganism. In some cases, the order of the genes can be determined after the gene has been inserted in the genome of the microorganism.

The microorganism used in this method can be any described above, including but not limited to a prokaryote. Other microorganisms such as bacteria, yeast, or algae can be used. Microorganisms of particular interest include methanotrophs, such as those from the genera *Methylo-*

*bacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, or *Methyloacidophilum*. One desired species can include a *Methylococcus capsulatus*.

An exemplary method of making a genetically modified microorganism disclosed herein is contacting (or transforming) a microorganism with a nucleic acid that expresses at least one heterologous gene encoding i) an acetoin reductase (e.g., NADPH- or NADH-dependent); ii) an alpha-acetolactate decarboxylase (budA); iii) a acetolactate synthase, or iv) any combination thereof. The microorganism can be any microorganism that is capable of converting a C1 carbon to a product. In some cases, the product is 2,3-BDO.

The NADPH- or NADH-dependent acetoin reductase, alpha-acetolactate decarboxylase (budA); and/or acetolactate synthase can be any of the variations described above. For example, the acetoin reductase can be from a gram positive bacterium, such as from the genus *Clostridium*, like the species *Clostridium autoethanogenum*.

The genes that are inserted into a microorganism can be heterologous to the microorganism itself. For example, if the microorganism is a methanotroph, the inserted genes can, for example, be from yeast, a bacterium, or a different species of methanotroph. Further, the genes can be endogenously part of the genome of the microorganism.

The genes can be inserted into a microorganism through the use of vectors. In some cases, the genes can be inserted into the genome of the microorganism. In some cases, both techniques can be used when two or more genes are inserted into a microorganism. For example, a gene can be inserted into the genome of a microorganism by, for example, use of an integration vector. Subsequently, an additional gene can be transformed into the microorganism through an episomal vector. In some cases, the vector can present a specific order of genes. For example, in some cases the vector can comprise a gene encoding for an acetolactate synthase, where the gene is 5' in relation to any other gene on the vector. In some cases, the vector can comprise a gene encoding for an acetoin reductase, where the gene is 3' in relation to any other gene on the vector. In some cases, the vector can comprise a gene encoding for an alpha-acetolactate decarboxylase, which is neither 5' or 3' in relation to any other gene on the vector.

In some cases, the genetically modified microorganisms made by the methods described throughout, can produce a desired product at higher titers when fermented at a higher temperature. For example, the genetically modified microorganisms can be made to produce higher titers of products, such as 2,3-BDO, butadiene, and/or MEK, when incubated at a temperature of greater than 37° C. (but no greater than a temperature of 100° C.). In some cases, the genetically modified microorganisms can be made to produce higher product titers when incubated at 42° C. compared to at 37° C. In some cases, the genetically modified microorganisms can be made to produce higher product titers when incubated at 41° C. compared to at 37° C. In some cases, the genetically modified microorganism can be made to produce higher product titers when incubated at 42° C. compared to at 45° C. In some cases, the genetically modified microorganism can be made to produce higher product titers when incubated at 41° C. compared to at 45° C. In some cases, the genetically modified microorganisms can be made to produce higher product titers when incubated at 37° C. compared to at 45° C. In some cases, the genetic modifications produce the increased tolerance/preference for higher temperatures.

Techniques for Genetic Modification

The microorganisms disclosed herein may be genetically engineered by using classic microbiological techniques. Some of such techniques are generally disclosed, for example, in Sambrook et al., 1989, Molecular Cloning: A Laboratory Manual, Cold Spring Harbor Labs Press.

The genetically modified microorganisms disclosed herein may include a polynucleotide that has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, overexpression, activation, enhancement, addition, or up-regulation of a gene. Addition of a gene to increase gene expression can include maintaining the gene(s) on replicating plasmids or integrating the cloned gene(s) into the genome of the production microorganism. Furthermore, increasing the expression of desired genes can include operatively linking the cloned gene(s) to native or heterologous transcriptional control elements.

Where desired, the expression of one or more of the enzymes provided herein is under the control of a regulatory sequence that controls directly or indirectly the enzyme expression in a time-dependent fashion during the fermentation. In some cases, inducible promoters can be used to achieve this.

In some cases, a microorganism is transformed or transfected with a genetic vehicle, such as an expression vector comprising a heterologous polynucleotide sequence coding for the enzymes are provided herein. In some cases, the vector(s) can be an episomal vector, the gene sequence can be integrated into the genome of the microorganism, or any combination thereof. In some cases, the vectors comprising the heterologous polynucleotide sequence encoding for the enzymes provided herein are integrated into the genome of the microorganism.

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

Transfection

Standard transfection techniques can be used to insert genes into a microorganism. As used herein, the term "transfection" or "transformation" and their grammatical equivalents can refer to the insertion of an exogenous nucleic acid or polynucleotide into a host cell. The exogenous nucleic acid or polynucleotide may be maintained as a non-integrated vector, for example, a plasmid or episomal vector, or alternatively, can be integrated into the host cell genome. The term transfecting or transfection is intended to encompass all conventional techniques for introducing nucleic acid or polynucleotide into microorganisms. Examples of transfection techniques include, but are not limited to, calcium phosphate precipitation, DEAE-dextran-mediated transfection, lipofection, electroporation, microinjection, rubidium chloride or polycation mediated transfection, protoplast fusion, and sonication. The transfection method that provides optimal transfection frequency and expression of the construct in the particular host cell line and type is favored. For stable transfectants, the constructs are integrated so as to be stably maintained within the host chromosome. In some cases, the preferred transfection is a stable transfection. In some cases, the integration of the gene occurs at a specific locus within the genome of the microorganism.

Transformation

Expression vectors or other nucleic acids may be introduced to selected microorganisms by any of a number of suitable methods. For example, vector constructs may be introduced to appropriate cells by any of a number of transformation methods for plasmid vectors. Standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods can be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to certain types of cells, the method used may depend on the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. Many companies offer kits and ways for this type of transfection.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation.

Microorganisms can be transformed or transfected with the above-described expression vectors or polynucleotides coding for one or more enzymes as disclosed herein and cultured in nutrient media modified as appropriate for the specific microorganism, inducing promoters, selecting transformants, or amplifying the genes encoding the desired sequences. In some cases, electroporation methods can be used to deliver an expression vector.

Expression of a vector (and the gene contained in the vector) can be verified by an expression assay, for example, qPCR or by measuring levels of RNA. Expression level can be indicative also of copy number. For example, if expression levels are extremely high, this can indicate that more than one copy of a gene was integrated in a genome. Alternatively, high expression can indicate that a gene was integrated in a highly transcribed area, for example, near a highly expressed promoter. Expression can also be verified by measuring protein levels, such as through Western blotting.

CRISPR/Cas System

The methods disclosed throughout can involve pinpoint insertion of genes or the deletion of genes (or parts of genes). Methods described herein can use a CRISPR/cas system. For example, double-strand breaks (DSBs) can be generated using a CRISPR/cas system, e.g., a type II CRISPR/cas system. A Cas enzyme used in the methods disclosed herein can be Cas9, which catalyzes DNA cleavage. Enzymatic action by Cas9 from *Streptococcus pyogenes* or any closely related Cas9 can generate double stranded breaks at target site sequences which hybridize to 20 nucleotides of a guide sequence and have a protospacer-adjacent motif (PAM) following the 20 nucleotides of the target sequence.

A vector can be operably linked to an enzyme-coding sequence encoding a CRISPR enzyme, such as a Cas protein. Cas proteins that can be used include class 1 and class 2. Non-limiting examples of Cas proteins include Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within 1, 2, 3, 4, 5, 6, 7, 8, 9, 10, 15, 20, 25, 30, 35, 40, 45, 50, 60, 70, 80, 90, 100, 125, 150, 175, 200, 300, 400, 500, or more base pairs from the first or last nucleotide of a target sequence. A vector that encodes a CRISPR enzyme that is mutated to with respect, to a corresponding wild-type enzyme such that the mutated CRISPR enzyme lacks the ability to cleave one or both strands of a target polynucleotide containing a target sequence can be used.

A vector that encodes a CRISPR enzyme comprising one or more nuclear localization sequences (NLSs) can be used. For example, there can be 1, 2, 3, 4, 5, 6, 7, 8, 9, 10 NLSs used. A CRISPR enzyme can comprise the NLSs at or near the amino-terminus (e.g., 1, 2, 3, 4, 5, 6, 7, 8, 9, 10 NLSs), or at or near the carboxy-terminus (e.g., 1, 2, 3, 4, 5, 6, 7, 8, 9, 10 NLSs), or any combination of these (e.g., one or more NLS at the amino-terminus and one or more NLS at the carboxy terminus). When more than one NLS is present, each can be selected independently of others, such that a single NLS can be present in more than one copy and/or in combination with one or more other NLSs present in one or more copies.

CRISPR enzymes used in the methods can comprise at most 6 NLSs. An NLS is considered near the N- or C-terminus when the nearest amino acid to the NLS is within 50 amino acids along a polypeptide chain from the N- or C-terminus, e.g., within 1, 2, 3, 4, 5, 10, 15, 20, 25, 30, 40, or 50 amino acids.

Guide RNA

As used herein, the term "guide RNA" and its grammatical equivalents can refer to an RNA which can be specific for a target DNA and can form a complex with Cas protein. An RNA/Cas complex can assist in "guiding" Cas protein to a target DNA.

A method disclosed herein also can comprise introducing into a cell or embryo at least one guide RNA or nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-chain RNA, or single guide RNA (sgRNA) formed by fusion of a portion (e.g., a functional portion) of crRNA and tracrRNA. A guide RNA can also be a dualRNA comprising a crRNA and a tracrRNA. Furthermore, a crRNA can hybridize with a target DNA.

As discussed above, a guide RNA can be an expression product. For example, a DNA that encodes a guide RNA can be a vector comprising a sequence coding for the guide RNA. A guide RNA can be transferred into a cell or microorganism by transfecting the cell or microorganism with an isolated guide RNA or plasmid DNA comprising a sequence coding for the guide RNA and a promoter. A guide RNA can also be transferred into a cell or microorganism in other way, such as using virus-mediated gene delivery.

A guide RNA can be isolated. For example, a guide RNA can be transfected in the form of an isolated RNA into a cell or microorganism. A guide RNA can be prepared by in vitro transcription using any in vitro transcription system. A guide RNA can be transferred to a cell in the form of isolated RNA rather than in the form of plasmid comprising encoding sequence for a guide RNA.

A guide RNA can comprise three regions: a first region at the 5' end that can be complementary to a target site in a chromosomal sequence, a second internal region that can form a stem loop structure, and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA can be complementary to sequence at a target site in a chromosomal sequence such that the first region of the guide RNA can base pair with the target site. In some cases, a first region of a guide RNA can comprise from 10 nucleotides to 25 nucleotides (i.e., from 10 nts to 25 nts; or 10 nts to 25 nts; or from 10 nts to 25 nts; or from 10 nts to 25 nts) or more. For example, a region of base pairing between a first region of a guide RNA and a target site in a chromosomal sequence can be 10, 11, 12, 13, 14, 15, 16, 17, 18, 19, 20, 22, 23, 24, 25, or more nucleotides in length. Sometimes, a first region of a guide RNA can be 19, 20, or 21 nucleotides in length.

A guide RNA can also comprises a second region that forms a secondary structure. For example, a secondary structure formed by a guide RNA can comprise a stem (or hairpin) and a loop. A length of a loop and a stem can vary. For example, a loop can range from 3 to 10 nucleotides in length, and a stem can range from 6 to 20 base pairs in length. A stem can comprise one or more bulges of 1 to 10 nucleotides. The overall length of a second region can range from 16 to 60 nucleotides in length. For example, a loop can be 4 nucleotides in length and a stem can be 12 base pairs.

A guide RNA can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than 4 nucleotides in length. For example, the length of a third region can range from 5 to 60 nucleotides in length.

A guide RNA can be introduced into a cell or embryo as an RNA molecule. For example, a RNA molecule can be transcribed in vitro and/or can be chemically synthesized. An RNA can be transcribed from a synthetic DNA molecule, e.g., a gBlocks® gene fragment. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III). Plasmid vectors that can be used to express guide RNA include, but are not limited to, px330 vectors and px333 vectors. In some cases, a plasmid vector (e.g., px333 vector) can comprise two guide RNA-encoding DNA sequences.

A DNA sequence encoding a guide RNA can also be part of a vector. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A DNA molecule encoding a guide RNA can also be linear. A DNA molecule encoding a guide RNA can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

Site-Specific Insertion

Insertion of the genes can be site-specific. For example, one or more genes can be inserted adjacent to a promoter.

Modification of a targeted locus of a microorganism can be produced by introducing DNA into microorganisms, where the DNA has homology to the target locus. DNA can include a marker gene, allowing for selection of cells comprising the integrated construct. Homologous DNA in a target vector can recombine with DNA at a target locus. A marker gene can be flanked on both sides by homologous DNA sequences, a 3' recombination arm, and a 5' recombination arm.

A variety of enzymes can catalyze insertion of foreign DNA into a microorganism genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, Φ31 integrase (a serine recombinase derived from *Streptomyces* phage Φ31), or bacteriophage derived site-specific recombinases (including Flp, lambda integrase, bacteriophage HK022 recombinase, bacteriophage R4 integrase and phage TP901-1 integrase).

The CRISPR/Cas system can be used to perform site specific insertion. For example, a nick on an insertion site in the genome can be made by CRISPR/cas to facilitate the insertion of a transgene at the insertion site.

The methods described herein, can utilize techniques which can be used to allow a DNA or RNA construct entry into a host cell include, but are not limited to, calcium phosphate/DNA coprecipitation, microinjection of DNA into a nucleus, electroporation, bacterial protoplast fusion with intact cells, transfection, lipofection, infection, particle bombardment, sperm mediated gene transfer, or any other technique.

Certain aspects disclosed herein can utilize vectors (including the ones described above). Any plasmids and vectors can be used as long as they are replicable and viable in a selected host microorganism. Vectors known in the art and those commercially available (and variants or derivatives thereof) can be engineered to include one or more recombination sites for use in the methods. Vectors that can be used include, but not limited to eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), pXT1, pSG5, pPbac, pMbac, pMClneo, and pOG44 (Stratagene, Inc.), and pYES2, pAC360, pBlueBa-cHis A, B, and C, pVL1392, pBlueBac111, pCDM8, pcDNA1, pZeoSV, pcDNA3, pREP4, pCEP4, and pEBVHis (Invitrogen, Corp.), and variants or derivatives thereof.

These vectors can be used to express a gene or portion of a gene of interest. A gene of portion or a gene can be inserted by using known methods, such as restriction enzyme-based techniques.

IV. Other Methods

Methods of Making Useful Chemicals

The genetically modified microorganisms described herein can be used to make useful chemicals, including but not limited to acetoin, 2,3-BDO, MEK, butadiene, and/or butene.

The microorganism can be any of the microorganisms discussed throughout including but not limited to a prokaryote, such as a methanotroph.

The carbon substrate can be any carbon substrate discussed throughout including but not limited to a C1 carbon substrate, such as methane.

The fermentation conditions used during the making of the useful chemicals can be any condition described throughout, such as temperature. For example, temperature of fermentation can be performed at between 37° C. to 45° C. In some cases, the temperature fermentation can be performed at 42° C. In some cases, the temperature fermentation can be performed at 41° C.

2-Acetolactate

Disclosed herein is a method of making 2-acetolactate comprising contacting a genetically modified microorganism with a carbon substrate, where the microorganism comprises a heterologous gene encoding acetolactate synthase (AlsS). In some cases, the heterologous gene is integrated into the genome of the microorganism. In some cases, the heterologous gene is episomally expressed. In some cases, the heterologous gene is both episomally expressed and integrated into the genome of the microorganism. In some cases, the heterologous acetolactate synthase gene is 5' in relation to any other heterologous gene (whether expressed on an episomal vector or integrated into the genome of the microorganism). In some cases, where the microorganism used has more than one chromosome, the terms 5' or 3' can be in reference to the genes contained on a single chromosome. The method can further include growing the microorganism to produce 2-acetolactate. The AlsS can be substantially similar to any one of SEQ ID NO: 1, 3, or 19. In some cases, the AlsS can be encoded by a nucleic acid that is substantially similar to any one of SEQ ID NO: 2, 4, or 20. The AlsS gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains lanthanum (e.g., at least 1 μM lanthanum) and then subsequently the lanthanum can be diluted. This can occur before growing the microorganism to produce 2-acetolactate. The 2-acetolactate produced can be substantially pure. The 2-acetolactate that is produced can be recovered. Additionally, 2-acetolactate products (i.e., by-products) can also be recovered. For example, diacetyl can be recovered as a by-product.

The 2-acetolactate can be further processed by the same microorganism, a different microorganism, or outside the microorganism (i.e., in vitro). Various enzymatic reactions or even spontaneous reactions can occur. For example, 2-acetolactate can be spontaneously converted into diacetyl. 2-acetolactate can also be converted to acetoin through the use of an alpha-acetolactate decarboxylase. Further 2-acetolactate can also be converted to 2,3-dihydroxy-2-methylbutanoic acid through a reduction reaction by 3-ketoacid reductase.

Therefore, the same microorganism can comprise an alpha-acetolactate decarboxylase and/or a 3-ketoacid reductase. In other instances, a different microorganism can comprise an alpha-acetolactate decarboxylase and/or a 3-ketoacid reductase or the alpha-acetolactate decarboxylase and/or a 3-ketoacid reductase is isolated from a cell. If the alpha-acetolactate decarboxylase and/or a 3-ketoacid reductase is in a different microorganism or is isolated from a cell, the microorganism/isolated enzyme can convert 2-acetolactate that is in the culture media (either by supplemental addition or by secretion by an acetoin producing microorganism). The conversion of 2-acetolactate by alpha-acetolactate decarboxylase and/or a 3-ketoacid reductase can produce acetoin and/or 2,3-dihydroxy-2-methylbutanoic acid, respectively.

Acetoin

Disclosed herein is a method of making acetoin comprising contacting a genetically modified microorganism with a carbon substrate, where the microorganism comprises a heterologous gene encoding for alpha-acetolactate decarboxylase (budA). In some cases, the heterologous gene is integrated into the genome of the microorganism. In some cases, the heterologous gene is episomally expressed. In some cases, the heterologous gene is both episomally expressed and integrated into the genome of the microorganism. In some cases, the alpha-acetolactate decarboxylase is neither 5' or 3' in relation to any other heterologous gene (whether expressed on an episomal vector or integrated into the genome of the microorganism). For example, with regarding to the acetolactate decarboxylase gene, there is at least one heterologous gene that is upstream (further 5') of the acetolactate decarboxylase gene as well as at least one additional heterologous gene that is downstream (further 3') of the acetolactate decarboxylase gene. In some cases, where the microorganism used has more than one chromosome, the terms 5' or 3' can be in reference to the genes contained on a single chromosome. The method can further comprise growing the microorganism to produce acetoin. The budA gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains lanthanum (e.g., at least 1 μM lanthanum) and then subsequently the lanthanum can be diluted. This can occur before growing the microorganism to produce acetoin. The acetoin produced can be substantially pure. The acetoin that is produced can be recovered. Additionally, non-acetoin products (i.e., by-products) can also be recovered.

The acetoin can be further processed by the same microorganism, a different microorganism, or outside a microorganism (i.e., in vitro) through an acetoin reductase (e.g., an NADH-dependent or NADPH-dependent acetoin reductase). The same microorganism can comprise an acetoin reductase (e.g., an NADH-dependent or NADPH-dependent acetoin reductase). In other instances, a different microorganism can comprise an acetoin reductase or the acetoin reductase is isolated from a cell. If the acetoin reductase is in a different microorganism or is isolated from a cell, the microorganism/isolated enzyme can convert acetoin reductase that is in the culture media (either by supplemental addition or by secretion by an acetoin producing microorganism). The reduction of acetoin by acetoin reductase can produce 2,3-BDO.

Further conversion of 2,3-BDO into various products can occur through different fermentation processes or by different catalytic conversions.

2,3-BDO

Disclosed herein is a method of making 2,3-BDO comprising contacting a genetically modified microorganism with a carbon substrate, where the microorganism comprises at least one heterologous gene encoding: (i) an acetoin reductase; (ii) an alpha-acetolactate decarboxylase (budA); (iii) an AlsS; or (iv) any combination thereof. In some cases, the at least one heterologous gene is integrated into the genome of the microorganism. In some cases, the at least one heterologous gene is episomally expressed. In some cases, the at least one heterologous gene is both episomally expressed and integrated into the genome of the microorganism. In some cases, the heterologous gene encoding the acetolactate synthase is 5' in relation to any other heterologous gene. In some cases, where the microorganism used has more than one chromosome, the terms 5' or 3' can be in reference to the genes contained on a single chromosome. In some cases, the heterologous gene encoding the acetoin reductase is the 3' heterologous gene in relation to any other heterologous gene. In some cases, the heterologous gene encoding the alpha-acetolactate decarboxylase is neither 5' or 3' in relation to any other heterologous gene. The method can further comprise growing the microorganism to produce 2,3-BDO. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains lanthanum (e.g., at least 1 μM lanthanum) and then subsequently the lanthanum can be diluted. This can occur before growing the microorganism to produce 2,3-BDO.

The 2,3-BDO that is produced from these methods can be substantially pure. The 2,3-BDO produced can be recovered. Additionally, non-2,3-BDO products (i.e., by-products) can also be recovered, such as 2-acetolactate and acetoin.

MEK

Disclosed herein is a method for making MEK comprising contacting a genetically modified microorganism with a carbon substrate, where the microorganism comprises at least one heterologous gene encoding: (i) an acetoin reductase; (ii) an alpha-acetolactate decarboxylase (budA); (iii) an AlsS; or (iv) any combination thereof. In some cases, the at least one heterologous gene is integrated into the genome of the microorganism. In some cases, the at least one heterologous gene is episomally expressed. In some cases, the at least one heterologous gene is both episomally expressed and integrated into the genome of the microorganism. In some cases, the heterologous gene encoding the acetolactate synthase is 5' in relation to any other heterologous gene. In some cases, where the microorganism used has more than one chromosome, the terms 5' or 3' can be in reference to the genes contained on a single chromosome. In some cases, the heterologous gene encoding the acetoin reductase is the 3' in relation to any other heterologous gene. In some cases, the heterologous gene encoding the alpha-acetolactate decarboxylase is neither 5' or 3' in relation to any other heterologous gene. The method can further comprise growing the microorganism to produce 2,3-BDO. In addition, the method can also further comprise contacting the 2,3-BDO produced with a catalyst to produce MEK. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains lanthanum (e.g., at least 1 μM lanthanum) and then subsequently the lanthanum can be diluted. This can occur before growing the microorganism to produce 2,3-BDO. In some cases, the 2,3-BDO can be isolated or purified before proceeding to contacting the 2,3-BDO produced with a catalyst to produce MEK.

The catalyst can be an enzymatic catalyst or a non-enzymatic catalyst. The catalyst can include any catalyst that is capable of producing MEK. For example, MEK can be obtained by the direct dehydration of 2,3-BDO over a variety of catalysts such as alumina, direct reaction with sulfuric acid, Cu, A103, and/or zeolite (or other solid acid catalysts) (see e.g., Emerson, R. R., et al., "Kinetics of dehydration of aqueous 2,3-butanediol to methyl ethyl ketone," Ind. Eng. Chem. Prod. Res. Dev., p. 473-477 (1982)). General acid catalysts such as metal oxides and zeolites mainly produce MEK, IBA, butenes, and $C_1$-$C_3$ gaseous compounds. For example, 10% H3PO4/Silica gel 60 produces 43% 1,3-butadiene 43%, 41% MEK and 8% IBA. Use of the zeolite ZSM-5 produces greater than 80% MEK. In some cases ZSM-5 produces over 90% MEK. In some cases, the catalyst and/or the reaction mixture does not contain alkali metals, such as potassium (K), Rubidium (Rb), and/or Cesium (Cs).

The acid-catalyzed dehydration of one water molecule from 2,3-BDO produces a carbocation intermediate. A pinacol rearrangement produces methyl ethyl ketone (MEK) and isobutylaldehyde (IBA).

Additionally, the 2,3-BDO made by the microorganisms and the methods described throughout can be further processed by a diol dehydratase (B12). This enzymatic reaction can produce MEK (also known as butan-2-one). Thus, disclosed is a method of making MEK comprising: (a) contacting a genetically modified microorganism with a carbon substrate, where the microorganism comprises a heterologous gene encoding for diol dehydratase; and (b) growing the microorganism to produce MEK. The microorganism can also comprise an acetolactate synthase (AlsS), alpha-acetolactate (budA), and/or acetoin reductase (butA).

In some cases, the MEK can be further processed by an alcohol dehydrogenase. This enzymatic reaction can produce butan-2-ol (also known as 2-butanol). Thus, disclosed is a method of making butan-2-ol comprising: (a) contacting a genetically modified microorganism with a carbon substrate, where the microorganism comprises a heterologous gene encoding for an alcohol dehydrogenase; and (b) growing the microorganism to produce butan-2-ol. The microorganism can also comprise an acetolactate synthase (AlsS), alpha-acetolactate (budA), acetoin reductase (butA), and/or diol dehydratase (B12).

1,3-Butadiene (Butadiene)

Disclosed herein is a method for making butadiene, where the method comprises contacting a genetically modified microorganism with a carbon substrate, where the microorganism comprises at least one heterologous gene encoding: (i) an acetoin reductase; (ii) an alpha-acetolactate decarboxylase (budA); (iii) an AlsS; or (iv) any combination thereof. In some cases, the at least one heterologous gene is integrated into the genome of the microorganism. In some cases, the at least one heterologous gene is episomally expressed. In some cases, the at least one heterologous gene is both episomally expressed and integrated into the genome of the microorganism. In some cases, the heterologous gene encoding the acetolactate synthase is 5' in relation to any other heterologous gene. In some cases, where the microorganism used has more than one chromosome, the terms 5' or 3' can be in reference to the genes contained on a single chromosome. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene. The method can further comprise growing the microorganism to produce 2,3-BDO. The method can also further comprise contacting the 2,3-BDO produced with a catalyst to produce butadiene. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains lanthanum (e.g., at least 1 μM lanthanum) and then subsequently the lanthanum can be diluted. This can occur before growing the microorganism to produce 2,3-BDO.

The catalyst can be an enzymatic catalyst or a non-enzymatic catalyst. The catalyst can include any catalyst that is capable of dehydrating 2,3-BDO. The catalyst can include any catalyst that is capable of producing a hydride shift. For example, alumina or a direct reaction with sulfuric acid (Emerson, R. R., et al., "Kinetics of dehydration of aqueous 2,3-butanediol to methyl ethyl ketone," *Ind. Eng. Chem. Prod. Res. Dev.,* 21(3), pp. 473-477 (1982)). Additionally, greater than 80% conversion of 2,3-BDO to butadiene can be made by using a $SiO_2$-supported cesium dihydrogen phosphate ($CsH_2PO_4$) catalyst. In generally, 10% of a $CsH_2PO_4$ catalyst can be used. In some cases, the conversion can be greater than 90% conversion. Examples of catalysts that can be used include, but are not limited to 10% CsH2PO4/CARiACT Q6 and/or 10% CsH2PO4/CARiACT Q10. (Further, the use of a use of a catalyst in which the alkali metal, such as, is K, Rb, or Cs, can lead to a higher butadiene production, and less of a MEK production. (See e.g., U.S. Pat. Appl. Pub. No. 2016/0229765). Thus, the method disclosed herein can use additional alkali metals.

By way of further example, butadiene can also be obtained by the direct dehydration of 2,3-BDO over thoria catalyst, although most other dehydration catalysts give methyl ethyl ketone as the main product (Winfield, M. E., "The Catalytic Dehydration of 2,3-Butanediol to Butadiene. II. Adsorption Equilibri," *Australian Journal of Scientific Research, Series A*: Physical Sciences, vol. 3, p. 290-305 (1945)).

2-Butene (Butene)

Disclosed herein is a method for making butene, where the method comprises contacting a genetically modified microorganism with a carbon substrate, where the microorganism comprises at least one heterologous gene encoding for: (i) an acetoin reductase; (ii) an alpha-acetolactate decarboxylase (budA); (iii) an AlsS; or (iv) any combination thereof. In some cases, the at least one heterologous gene is integrated into the genome of the microorganism. In some cases, the at least one heterologous gene is episomally expressed. In some cases, the at least one heterologous gene is both episomally expressed and integrated into the genome of the microorganism. In some cases, the heterologous gene encoding the acetolactate synthase is 5' in relation to any other heterologous gene. In some cases, where the microorganism used has more than one chromosome, the terms 5' or 3' can be in reference to the genes contained on a single chromosome. In some cases, the heterologous gene encoding the acetoin reductase is 3' in relation to any other heterologous gene. In some cases, the heterologous gene encoding the alpha-acetolactate decarboxylase is neither 5' or 3' in relation to any other heterologous gene. The method can further comprise growing the microorganism to produce 2,3-BDO. The method can also further comprise contacting the 2,3-BDO produced with a catalyst to produce butene. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains lanthanum (e.g., at least 1 μM lanthanum) and then subsequently the lanthanum can be diluted. This can occur before growing the microorganism to produce 2,3-BDO.

Butene can be produced from 2,3-BDO. For example, treatment of the dial with HBr, followed by Zn powder can result in butene. The debrominations proceed with a high degree of anti-stereospecificity (House, H. O, and Ro, R, S, "The Stereochemistry of Elimination Reactions Involving Halohydrin Derivatives and Metals," *J. Am. Chem. Soc.* 80(1), p. 182-187(1958); Gordon, M., and Hay, J. V., "Stereochemistry of vapor phase dehalogenation of meso- and DL-2,3-dibromobutane with zinc," *J. Org. Chem.* 33(1), p. 427-427 (1968)), the mesa isomer giving the trans butene, and the (+) isomer the cis butene.

Butene can be converted into butadiene. For example, butenes can be catalytically dehydrogenated to 1,3-butadiene in the presence of superheated steam as a diluent and a heating medium (Voloch, M., et al., "2,3-Butanediol," *Industrial Chemicals, Biochemicals and Fuels*, Chapter 45, p. 933-947 (1985).

Methods of Making Commercially Useful Products

Although 2,3-BDO in itself can be used in some commercial useful aspects, many of the downstream products of 2,3-BDO can be used to produce additional commercially useful products. For example, butadiene, butene, and MEK can subsequently be used in a variety of processes for producing commercially useful products.

For example, butene may be used in the production of gasoline and butadiene. Butene can also be used as a component or precursor in the manufacture of $C_{12}$ paraffins, such as iso paraffins used as aviation fuels (see e.g., U.S. Pat. No. 7,338,541).

MEK can be used to dissolve many substances and may be used, for example, as a solvent in processes involving gums, resins, cellulose acetate, and nitrocellulose coatings and in vinyl films. Therefore, MEK can be useful in the manufacture of plastics, textiles, paraffin wax, and in household products such as lacquer, varnishes and paint remover, glues, and as a cleaning agent. MEK can also be used as a denaturing agent for denatured alcohol. MEK can also be used in dry erase markers as the solvent of the erasable dye. In addition, MEK is the precursor to methyl ethyl ketone peroxide, a catalyst used in some polymerization reactions. Further, MEK can be converted to 2-butanol by contacting the MEK with a catalyst such as ruthenium on carbon. MEK can also be converted to 2-butanol by contact with an alcohol dehydrogenase.

One of the most useful chemicals that can be produced by the processes herein is butadiene. Butadiene may be used to produce a variety of very useful products such as synthetic rubbers and polymer resins. While polybutadiene itself is a very soft, almost liquid material, polymers prepared from mixtures of butadiene with styrene or acrylonitrile, such as ABS, are both tough and elastic. Styrene-butadiene rubber is the material most commonly used for the production of automobile tires. Butadiene may also be used to make nylon via the intermediate adiponitrile, other synthetic rubber materials such as chloroprene, and the solvent sulfolane. In addition, butadiene may be used in the industrial production of 4-vinylcyclohexene via a dimerization reaction and cyclododecatriene via a trimerization reaction. Butadiene is also useful in the synthesis of cycloalkanes and cycloalkenes, as it reacts with double and triple carbon-carbon bonds through the Diels-Alder reaction. By way of further example, butadiene may be used in the manufacture of cycloalkanes, cycloalkenes, dodecandioic acid (DDDA), adiponitrile, caprolactam, styrene, ethylidene norbornene, lauryl lactam and 1,5-cyclooctadiene (COD).

It should be appreciated that the methods of the invention may be integrated or linked with one or more methods for the production of downstream products from butene, butadiene and/or MEK. For example, the methods of the invention may feed butene, butadiene and/or MEK directly or indirectly to chemical processes or reactions sufficient for the conversion or production of other useful chemical products. In some cases, as noted herein before, 2,3-BDO can be converted to one or more chemical products directly via the intermediate compounds butene, butadiene and/or MEK without the need for recovery of butene, butadiene and/or MEK from the method before subsequent use in production of the one or more chemical products.

In particular cases, methane is converted to 2,3-BDO, which is then subsequently converted to butene, butadiene and/or MEK by one or more chemical processes, which in turn is converted to one or more chemical products by one or more chemical processes. In particular cases, the one or more chemical products are produced without recovering the butane, butadiene and/or MEK. In another embodiment, 2,3-BDO is converted to one or more chemical products in a single chemical process via one or more of the butane, butadiene and/or MEK intermediate compounds.

V. Fermentation

In general, the microorganisms disclosed herein should be used in fermentation conditions that are appropriate to convert a C1 carbon (such as methane) to 2,3-BDO (or other desired product). Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The optimum reaction conditions will depend partly on the particular microorganism of used. However, in general, the fermentation can be performed at a pressure higher than ambient pressure. Operating at increased pressures can allow for a significant increase in the rate of C1-carbon transfer from the gas phase to the liquid phase where it can be taken up by the microorganism as a carbon source for the production of 2,3-BDO. This in turn can mean that the retention time (defined as the liquid volume in the bioreactor divided by the input gas flow rate) can be reduced when bioreactors are maintained at elevated pressure rather than atmospheric pressure.

The use of pressurized systems can greatly reduce the volume of the bioreactor required, and consequently the capital cost of the fermentation equipment. In some cases, reactor volume can be reduced in linear proportion to increases in reactor operating pressure, i.e. bioreactors operated at 10 atmospheres of pressure need only be one tenth the volume of those operated at 1 atmosphere of pressure.

It is also desirable that the rate of introduction of the C1-carbon substrate (such as methane) containing gaseous substrate is such as to ensure that the concentration of the C1-carbon substrate (such as methane) in the liquid phase does not become limiting. This is because a consequence of C1-carbon substrate (e.g., methane) limited conditions may be that the 2,3-BDO product (or other desired product) is consumed by the culture.

Preculturing

Preculturing the various strains of genetically microorganisms described throughout can lead to increase titers of the multicarbon products described throughout such as 2,3-BDO, butadiene, and/or MEK.

Preculturing can include adding to the media an antibiotic, such as kanamycin, a carbon source, such as methane or other C1 carbon, and/or substances to activate or repress a molecular switch.

Typically, preculturing can be performed for a time of less than 240 hours, depending on the species of the microorganism used. Preculturing allows for sufficient biomass to be created in order to efficiently increase product titers. In some cases, the preculturing is less than 240 hours. In some cases, the preculturing is less than 220 hours. In some cases, the preculturing is less than 200 hours. In some cases, the preculturing is less than 180 hours. In some cases, the preculturing is less than 160 hours. In some cases, the preculturing is less than 140 hours. In some cases, the preculturing is less than 120 hours. In some cases, the preculturing is less than 100 hours. In some cases, the preculturing is less than 96 hours. In some cases, the preculturing is less than 90 hours. In some cases, the preculturing is less than 84 hours. In some cases, the preculturing is less than 78 hours. In some cases, the preculturing is less than 72 hours. In some cases, the preculturing is less than 68 hours. In some cases, the preculturing is less than 62 hours. In some cases, the preculturing is less than 56 hours. In some cases, the preculturing is less than 50 hours. In some cases, the preculturing is less than 48 hours. In some cases, the preculturing is less than 46 hours. In some cases, the preculturing is less than 44 hours. In some cases, the preculturing is less than 42 hours. In some cases, the preculturing is less than 40 hours. In some cases, the preculturing is less than 38 hours. In some cases, the preculturing is less than 36 hours. In some cases, the preculturing is less than 34 hours. In some cases, the preculturing is less than 32 hours. In some cases, the preculturing is less than 30 hours. In some cases, the preculturing is less than 28 hours. In some cases, the preculturing is less than 26 hours. In some cases, the preculturing is less than 24 hours. In some cases, the preculturing is less than 22 hours. In some cases, the preculturing is less than 20 hours. In some cases, the preculturing is less than 18 hours. In some cases, the preculturing is less than 16 hours. In some cases, the preculturing is less than 14 hours. In some cases, the preculturing is less than 12 hours. In some cases, the preculturing is less than 10 hours. In some cases, the preculturing is less than 8 hours. In some cases, the preculturing is less than 6 hours. In some cases, the preculturing is less than 4 hours. In some cases, the preculturing is less than 2 hours. In some cases, the preculturing is less than 1 hour. In some cases, there is no preculturing.

In some cases, the preculturing is between 240 hours and 1 hour. In some cases, the preculturing is between 220 hours. In some cases, the preculturing is between 200 hours and 2 hours. In some cases, the preculturing is between 180 hours and 4 hours. In some cases, the preculturing is between 160 hours and 6 hours. In some cases, the preculturing is between 140 hours and 8 hours. In some cases, the preculturing is between 120 hours and 10 hours. In some cases, the preculturing is between 100 hours and 12 hours. In some cases, the preculturing is between 96 hours and 18 hours. In some cases, the preculturing is between 90 hours and 24 hours. In some cases, the preculturing is between 84 hours and 36 hours. In some cases, the preculturing is between 78 hours and 40 hours. In some cases, the preculturing is between 72 hours and 42 hours. In some cases, the preculturing is between 56 hours and 44 hours. In some cases, the preculturing is between 50 hours and 46 hours.

When a substance to activate or repress a molecular switch is added to the preculture, the amount can vary. For example, in some cases, if the substance to activate or repress a molecular switch is a rare earth metal (such as lanthanum), the genetically modified microorganism that comprise only integrated genes, do not require any preculture containing the rare earth metal (such as lanthanum). However, in some cases, these integrated strains do require the rare earth metal (such as lanthanum), however, in small amounts. For example, the amount of the rare earth metal (such as lanthanum) required for preculture of the integrated strains can require less than 25 μM of the rare earth metal (such as lanthanum). In some cases, the amount of the rare earth metal (such as lanthanum) required for preculture of the integrated strains can require less than 20 μM. The amount of the rare earth metal (such as lanthanum) required for preculture of the integrated strains can require less than 15 μM. The amount of the rare earth metal (such as lanthanum) required for preculture of the integrated strains can require less than 10 μM. The amount of the rare earth metal (such as lanthanum) required for preculture of the integrated strains can require less than 7.5 μM. The amount of the rare earth metal (such as lanthanum) required for preculture of the integrated strains can require less than 5 μM. The amount of the rare earth metal (such as lanthanum) required for preculture of the integrated strains can require less than 2.5 μM. The amount of the rare earth metal (such as lanthanum) required for preculture of the integrated strains can require less than 1 μM.

However, when the microorganism comprises an episomally expressed genes (whether or not an additional integrated set of genes is already present in the microorganism), more of the rare earth metal (such as lanthanum) is required during preculture to optimize production. In some cases, these episomal strains require in preculture more than 1 μM of the rare earth metal (such as lanthanum). In some cases, these episomal strains require in preculture more than 2.5 μM of the rare earth metal (such as lanthanum). In some cases, these episomal strains require in preculture more than 5.0 μM of the rare earth metal (such as lanthanum). In some cases, these episomal strains require in preculture more than 7.5 μM of the rare earth metal (such as lanthanum). In some cases, these episomal strains require in preculture more than 10 μM of the rare earth metal (such as lanthanum). In some cases, these episomal strains require in preculture more than 12.5 μM of the rare earth metal (such as lanthanum). In some cases, these episomal strains require in preculture more than 15 μM of the rare earth metal (such as lanthanum). In some cases, these episomal strains require in preculture more than 17.5 μM of the rare earth metal (such as lanthanum). In some cases, these episomal strains require in preculture more than 20 μM of the rare earth metal (such as lanthanum). In some cases, these episomal strains require in preculture more than 25 μM of the rare earth metal (such as lanthanum). In some cases, these episomal strains require in preculture more than 30 μM of the rare earth metal (such as lanthanum). In some cases, these episomal strains require in preculture more than 35 μM of the rare earth metal (such as lanthanum). In some cases, these episomal strains require in preculture more than 40 μM of the rare earth metal (such as lanthanum). In some cases, these episomal strains require in preculture more than 45 μM of the rare earth metal (such as lanthanum). In some cases, these episomal strains require in preculture more than 50 μM of the rare earth metal (such as lanthanum). In some cases, these episomal strains require in preculture more than 75 μM of the rare earth metal (such as lanthanum). In some cases, these episomal strains require in preculture more than 100 μM of the rare earth metal (such as lanthanum).

In some cases, the amount of the rare earth metal (such as lanthanum) that is required in preculture to optimize production can be in a range of 0.5 μM to 100 μM of the rare earth metal (such as lanthanum). In some cases, a range of 0.5 μM to 50 μM of the rare earth metal (such as lanthanum) is required in preculture to optimize production. In other cases, a range of 1 μM to 20 μM of the rare earth metal (such as lanthanum) is required in preculture to optimize production. In some cases, a range of 2 μM to 15 μM of the rare earth metal (such as lanthanum) is required in preculture to optimize production. In some cases, a range of 3 μM to 12.5 μM of the rare earth metal (such as lanthanum) is required in preculture to optimize production. In some cases, a range of 4 μM to 12 μM of the rare earth metal (such as lanthanum) is required in preculture to optimize production. In some cases, a range of 5 μM to 11.5 μM of the rare earth metal (such as lanthanum) is required in preculture to optimize production. In some cases, a range of 6 μM to 11 μM of the rare earth metal (such as lanthanum) is required in preculture to optimize production. In some cases, a range of 7 μM to 10.5 μM of the rare earth metal (such as lanthanum) is required in preculture to optimize production. In some cases, a range of 8 μM to 10 μM of the rare earth metal (such as lanthanum) is required in preculture to optimize production.

In some cases, other rare earth metals, such as cerium (Ce), dysprosium (Dy), erbium (Er), europium (Eu), gadolinium (Gd), holmium (Ho), lutetium (Lu), neodymium (Nd), praseodymium (Pr), promethium (Pm), samarium (Sm), scandium (Sc), terbium (Tb), thulium (Tm), ytterbium (Yb), yttrium (Y), or any combination thereof, can be used. In other cases, sugars, such as IPTG and arabinose can be used.

Fermentation Conditions pH can be optimized based on the microorganism used. For example, the pH used during the methanotroph fermentation of methane to a desired product, can be from 4 to 10. In other instances, the pH can be from 5 to 9; 6 to 8; 6.1 to 7.9; 6.2 to 7.8; 6.3 to 7.7; 6.4 to 7.6; or 6.5 to 7.5. For example, the pH can be from 6.6 to 7.4. In some cases, the pH can be from 5 to 9. In some cases, the pH can be from 6 to 8. In some cases, the pH can be from 6.1 to 7.9. In some cases, the pH can be from 6.2 to 7.8. In some cases, the pH can be from 6.3 to 7.7. In some cases, the pH can be from 6.4 to 7.6. In some cases, the pH can be from 6.5 to 7.5. In some cases, the pH used for the fermentation of methanotrophs can be greater than 6.

Temperature can also be adjusted based on the microorganism used. For example, the temperature used during the methanotroph fermentation of methane to a desired product, can be from 30 C.° to 45 C.°. In other instances, the temperature of the fermentation can be from 30 C.° to 45 C.°; 31 C.° to 44 C.°; 32 C.° to 43 C.°; 33 C.° to 42 C.°; 34 C.° to 41 C.°; 35 C.° to 40 C.°. For example, the temperature can be from 36 C.° to 39 C.° (e.g., 36 C.°, 37 C.°, 38 C.°, or 39 C.°). In some cases, the temperature can be from 30 C.° to 45 C.° (e.g., 30 C.°, 31 C.°, 32 C.°, 33 C.°, 34 C.°, 35 C.°, 36 C.°, 37 C.°, 38 C.°, 39 C.°, 40 C.°, 41 C.°, 42 C.°, 43 C.°, 44 C.°, or 45 C.°). In some cases, the temperature can be from 31 C.° to 44 C.° (e.g., 31 C.°, 32 C.°, 33 C.°, 34 C.°, 35 C.°, 36 C.°, 37 C.°, 38 C.°, 39 C.°, 40 C.°, 41 C.°, 42 C.°, 43 C.°, or 44 C.°). In some cases, the temperature can be from 32 C.° to 43 C.°. In some cases, the temperature can be from 33 C.° to 42 C.° (e.g., 33 C.°, 34 C.°, 35 C.°, 36 C.°, 37 C.°, 38 C.°, 39 C.°, 40 C.°, 41 C.°, or 42 C.°). In some cases, the temperature can be from 34 C.° to 41 C.° (e.g., 34 C.°, 35 C.°, 36 C.°, 37 C.°, 38 C.°, 39 C.°, 40 C.°, or 41 C.°). In some cases, the temperature can be from 35 C.° to 40 C.° (e.g., 35 C.°, 36 C.°, 37 C.°, 38 C.°, 39 C.°, or 40 C.°).

In some cases, the temperatures can be within one tenth of a degree. For example, in some cases, the temperature of fermentation can be 37.0 C.°, 37.1 C.°, 37.2 C.°, 37.3 C.°, 37.4 C.°, 37.5 C.°, 37.6 C.°, 37.7 C.°, 37.8 C.°, 37.9 C.°, 38.0 C.°, 38.1 C.°, 38.2 C.°, 38.3 C.°, 38.4 C.°, 38.5 C.°, 38.6 C.°, 38.7 C.°, 38.8 C.°, 38.9 C.°, 39.0 C.°, 39.1 C.°, 39.2 C.°, 39.3 C.°, 39.4 C.°, 39.5 C.°, 39.6 C.°, 39.7 C.°, 39.8 C.°, 39.9 C.°, 40.0 C.°, 40.1 C.°, 40.2 C.°, 40.3 C.°, 40.4 C.°, 40.5 C.°, 40.6 C.°, 40.7 C.°, 40.8 C.°, 40.9 C.°, 41.0 C.°, 41.1 C.°, 41.2 C.°, 41.3 C.°, 41.4 C.°, 41.5 C.°, 41.6 C.°, 41.7 C.°, 41.8 C.°, 41.9 C.°, 42.0 C.°, 42.1 C.°, 42.2 C.°, 42.3 C.°, 42.4 C.°, 42.5 C.°, 42.6 C.°, 42.7 C.°, 42.8 C.°, 42.9 C.°, 43.0 C.°, 43.1 C.°, 43.2 C.°, 43.3 C.°, 43.4 C.°, 43.5 C.°, 43.6 C.°, 43.7 C.°, 43.8 C.°, 43.9 C.°, 44.0 C.°, 44.1 C.°, 44.2 C.°, 44.3 C.°, 44.4 C.°, 44.5 C.°, 44.6 C.°, 44.7 C.°, 44.8 C.°, 44.9 C.°, 45.0 C.°, 45.1 C.°, 45.2 C.°, 45.3 C.°, 45.4 C.°, 45.5 C.°, 45.6 C.°, 45.7 C.°, 45.8 C.°, 45.9 C.°, 46.0 C.°, 46.1 C.°, 46.2 C.°, 46.3 C.°, 46.4 C.°, 46.5 C.°, 46.6 C.°, 46.7 C.°, 46.8 C.°, 46.9 C.°, 47.0 C.°, 47.1 C.°, 47.2 C.°, 47.3 C.°, 47.4 C.°, 47.5 C.°, 47.6 C.°, 47.7 C.°, 47.8 C.°, or 47.9 C.°.

In some cases, the temperature of fermentation can be from 37.0 C.° to 47.9 C.°. In some cases, the temperature of fermentation can be from 37.1 C.° to 47.8 C.°. In some cases, the temperature of fermentation can be from 37.2 C.° to 47.7 C.°. In some cases, the temperature of fermentation can be from 37.3 C.° to 47.6 C.°. In some cases, the temperature of fermentation can be from 37.4 C.° to 47.5 C.°. In some cases, the temperature of fermentation can be from 37.5 C.° to 47.4 C.°. In some cases, the temperature of fermentation can be from 37.6 C.° to 47.3 C.°. In some cases, the temperature of fermentation can be from 37.7 C.° to 47.2 C.°. In some cases, the temperature of fermentation can be from 37.8 C.° to 47.1 C.°. In some cases, the temperature of fermentation can be from 37.9 C.° to 47.0 C.°. In some cases, the temperature of fermentation can be from 38.0 C.° to 46.9 C.°. In some cases, the temperature of fermentation can be from 38.1 C.° to 46.8 C.°. In some cases, the temperature of fermentation can be from 38.2 C.° to 46.7 C.°. In some cases, the temperature of fermentation can be from 38.3 C.° to 46.6 C.°. In some cases, the temperature of fermentation can be from 38.4 C.° to 46.5 C.°. In some cases, the temperature of fermentation can be from 38.5 C.° to 46.4 C.°. In some cases, the temperature of fermentation can be from 38.6 C.° to 46.3 C.°. In some cases, the temperature of fermentation can be from 38.7 C.° to 46.2 C.°. In some cases, the temperature of fermentation can be from 38.8 C.° to 46.1 C.°. In some cases, the temperature of fermentation can be from 38.9 C.° to 46.0 C.°. In some cases, the temperature of fermentation can be from 39.0 C.° to 45.9 C.°. In some cases, the temperature of fermentation can be from 39.1 C.° to 45.8 C.°. In some cases, the temperature of fermentation can be from 39.2 C.° to 45.7 C.°. In some cases, the temperature of fermentation can be from 39.3 C.° to 45.6 C.°. In some cases, the temperature of fermentation can be from 39.4 C.° to 45.5 C.°. In some cases, the temperature of fermentation can be from 39.5 C.° to 45.4 C.°. In some cases, the temperature of fermentation can be from 39.6 C.° to 45.3 C.°. In some cases, the temperature of fermentation can be from 39.7 C.° to 45.2 C.°. In some cases, the temperature of fermentation can be from 39.8 C.° to 45.1 C.°. In some cases, the temperature of fermentation can be from 39.9 C.° to 45.0 C.°. In some cases, the temperature of fermentation can be from 40.0 C.° to 44.9 C.°. In some cases, the temperature of fermentation can be from 40.1 C.° to 44.8 C.°. In some cases, the temperature of fermentation can be from 40.2 C.° to 44.7 C.°. In some cases, the temperature of fermentation can be from 40.3 C.° to 44.6 C.°. In some cases, the temperature of fermentation can be from 40.4 C.° to 44.5 C.°. In some cases, the temperature of fermentation can be from 40.5 C.° to 44.4 C.°. In some cases, the temperature of fermentation can be from 40.6 C.° to 44.3 C.°. In some cases, the temperature of fermentation can be from 40.7 C.° to 44.2 C.°. In some cases, the temperature of fermentation can be from 40.8 C.° to 44.1 C.°. In some cases, the temperature of fermentation can be from 40.9 C.° to 44.0 C.°. In some cases, the temperature of fermentation can be from 41.0 C.° to 43.9 C.°. In some cases, the temperature of fermentation can be from 41.1 C.° to 43.8 C.°. In some cases, the temperature of fermentation can be from 41.2 C.° to 43.7 C.°. In some cases, the temperature of fermentation can be from 41.3 C.° to 43.6 C.°. In some cases, the temperature of fermentation can be from 41.4 C.° to 43.5 C.°. In some cases, the temperature of fermentation can be from 41.5 C.° to 43.4 C.°. In some cases, the temperature of fermentation can be from 41.6 C.° to 43.3 C.°. In some cases, the temperature of fermentation can be from 41.7 C.° to 43.2 C.°. In some cases, the temperature of fermentation can be from 41.8 C.° to 43.1 C.°. In some cases, the temperature of fermentation can be from 41.9 C.° to 43.0 C.°. In some cases, the temperature of fermentation can be from 42.0 C.° to 42.9 C.°. In some cases, the temperature of fermentation can be from 42.1 C.° to 42.8 C.°. In some cases, the temperature of fermentation can be from 42.2 C.° to 42.7 C.°. In some cases, the temperature of fermentation can be from 42.3 C.° to 42.6 C.°. In some cases, the temperature of fermentation can be from 42.4 C.° to 42.5 C.°.

Availability of oxygen and other gases such as gaseous C1-carbon substrates (such as methane) can affect yield and fermentation rate. For example, when considering oxygen availability, the percent of dissolved oxygen (DO) within the fermentation media can be from 1% to 40%. In certain instances, the DO concentration can be from 1.5% to 35%; 2% to 30%; 2.5% to 25%; 3% to 20%; 4% to 19%; 5% to 18%; 6% to 17%; 7% to 16%; 8% to 15%; 9% to 14%; 10% to 13%; or 11% to 12%. For example, in some cases the DO concentration can be from 2% to 30%. In other cases, the DO can be from 3% to 20%. In some cases, the DO can be from 4% to 10%. In some cases, the DO can be from 1.5% to 35%. In some cases, the DO can be from 2.5% to 25%. In some cases, the DO can be from 4% to 19%. In some cases, the DO can be from 5% to 18%. In some cases, the DO can be from 6% to 17%. In some cases, the DO can be from 7% to 16%. In some cases, the DO can be from 8% to 15%. In some cases, the DO can be from 9% to 14%. In some cases, the DO can be from 10% to 13%. In some cases, the DO can be from 11% to 12%.

When using a methanotroph, the type of methane substances can have an effect on yield and fermentation rates. For example, natural gas can be used, which typically has a methane content of above 85% (e.g., above 90%) methane. Other components within natural gas can include but is not limited to ethane, propane, iso-butane, normal-butane, iso-pentane, normal pentane, hexanes plus, nitrogen, carbon dioxide, oxygen, hydrogen, and hydrogen sulfides.

"Pure" methane can be used as well. In these cases, the methane typically comes from a tank. The methane contained within these tanks can range from 90% or greater methane content and the remaining gas are other gases (such as carbon dioxide). For example, gas having a methane content of greater than 90% can be used during the fermentation process. In certain instances, the methane concentration can be greater than 90%; 91%; 92%; 93%; 94%; 95%; 96%; 97%; 98%; 99%; or 99.9%. In some cases, the methane concentration can be 90% methane and 10% are other gases (such as carbon dioxide). In other instances, the methane concentration can be 91% methane and 9% are other gases (such as carbon dioxide). In some cases, the methane concentration can be 92% methane and 8% are other gases (such as carbon dioxide). In some cases, the methane concentration can be 93% methane and 7% are other gases (such as carbon dioxide). In some cases, the methane concentration can be 94% methane and 6% are other gases (such as carbon dioxide). In some cases, the methane concentration can be 95% methane and 5% are other gases (such as carbon dioxide). In other instances, the methane concentration can be 96% methane and 4% are other gases (such as carbon dioxide). In some cases, the methane concentration can be 97% methane and 3% are other gases (such as carbon dioxide). In some cases, the methane concentration can be 98% methane and 2% are other gases (such as carbon dioxide). In some cases, the methane concentration can be 99% methane and 1% are other gases (such as carbon dioxide). In some cases, the methane concentration can be 99.9% methane and 0.1% are other gases (such as carbon dioxide).

In cases where a switch is used, the media can comprise the molecule that induces or represses the switch. For example, when a lanthanum switch is used to repress the expression of one or more of the genes described herein, the media can comprise lanthanum, which will repress expression of the one or more genes under the control of the switch. In the case of lanthanum any one of the following concentrations can effectively repress expression of the one or more genes: 0.1 μM; 0.5 μM; 1 μM; 2 μM; 3 μM; 4 μM; 5 μM; 6 μM; 7 μM; 8 μM; 9 μM; 10 μM; 12.5 μM; 15 μM; 17.5 μM; 20 μM; 25 μM; 50 μM; 100 μM or more. In one case, 0.1 μM lanthanum can be used to repression expression of the one or more genes under the control of a lanthanum switch. In other cases, at least 0.5 μM lanthanum can be used. In other cases, at least 1 μM lanthanum can be used. In other cases, at least 2 μM lanthanum can be used. In other cases, at least 3 μM lanthanum can be used. In other cases, at least 4 μM lanthanum can be used. In other cases, at least 5 μM lanthanum can be used. In other cases, at least 6 μM lanthanum can be used. In other cases, at least 7 μM lanthanum can be used. In other cases, at least 8 μM lanthanum can be used. In other cases, at least 9 μM lanthanum can be used. In other cases, at least 10 μM lanthanum can be used. In other cases, at least 12.5 μM lanthanum can be used. In other cases, at least 15 μM lanthanum can be used. In other cases, at least 17.5 μM lanthanum can be used. In other cases, at least 20 μM lanthanum can be used. In other cases, at least 25 μM lanthanum can be used. In other cases, at least 50 μM lanthanum can be used. In other cases, at least 100 μM lanthanum can be used. In some cases, a range of 0.5 μM lanthanum to 100 μM lanthanum will effectively repress gene expression. In some cases, a range of 0.5 μM lanthanum to 50 μM lanthanum will repress gene expression. In other cases, a range of 1 μM lanthanum to 20 μM lanthanum will repress gene expression. In some cases, a range of 2 μM lanthanum to 15 μM lanthanum will repress gene expression. In some cases, a range of 3 μM lanthanum to 12.5 μM lanthanum will repress gene expression. In some cases, a range of 4 μM lanthanum to 12 μM lanthanum will repress gene expression. In some cases, a range of 5 μM lanthanum to 11.5 μM lanthanum will repress gene expression. In some cases, a range of 6 μM lanthanum to 11 μM lanthanum will repress gene expression. In some cases, a range of 7 μM lanthanum to 10.5 μM lanthanum will repress gene expression. In some cases, a range of 8 μM lanthanum to 10 μM lanthanum will repress gene expression.

In some cases, the lanthanum in the media can be diluted to turn on expression of the one or more lanthanum repressed genes. For example, in some cases, the dilution of lanthanum containing media can be 1:1 (1 part lanthanum containing media to 1 part non-lanthanum containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

In some cases, the microorganism can be grown in media comprising lanthanum. The media can then be diluted to effectively turn on the expression of the lanthanum repressed genes. The microorganism can be then grown in conditions to promote the production of desired products, such as 2,3-BDO and acetoin (or others disclosed throughout).

In some cases, other rare earth metals can be used. For example, other rare earth metals such as cerium (Ce), dysprosium (Dy), erbium (Er), europium (Eu), gadolinium (Gd), holmium (Ho), lutetium (Lu), neodymium (Nd), praseodymium (Pr), promethium (Pm), samarium (Sm), scandium (Sc), terbium (Tb), thulium (Tm), ytterbium (Yb), yttrium (Y), or any combination thereof, can be used to repress or activate a molecular switch.

Bioreactor

Fermentation reactions may be carried out in any suitable bioreactor. In some cases of the invention, the bioreactor can comprise a first, growth reactor in which the micro-organisms are cultured, and a second, fermentation reactor, to which broth from the growth reactor is fed and in which most of the fermentation product (2,3-BDO, for example) is produced.

Product Recovery

The fermentation of the microorganisms disclosed herein can produce a fermentation broth comprising a desired product (e.g., 2,3-BDO, MEK, and/or butadiene) and/or one or more by-products as well as the microorganisms (e.g., a genetically modified methanotroph), in a nutrient medium.

The microorganisms and the methods herein can produce 2,3-BDO at surprisingly high efficiency, more so than other known 2,3-BDO fermentation processes. For example, the microorganisms and the methods disclosed herein can convert a C1-carbon substrate (such as methane) at a rate of greater than 50%. This means that at least 50% of the C1-carbons within the systems are converted into product, such as 2,3-BDO. In some cases, the conversion of a C1-carbon substrate into 2,3-BDO can be at least 60%, 70%, 80%, 81%, 83%, 84%, 85%, 86%, 87%, 88%, 89%, 90%, 91%, 93%, 94%, 95%, 96%, 97%, 98%, or 99%. In some cases, the conversion of a C1-carbon substrate into 2,3-BDO can be at least 60%. In some cases, the conversion of a C1-carbon substrate into 2,3-BDO can be at least 70%. In some cases, the conversion of a C1-carbon substrate into 2,3-BDO can be at least 80%. In some cases, the conversion of a C1-carbon substrate into 2,3-BDO can be at least 81%. In some cases, the conversion of a C1-carbon substrate into 2,3-BDO can be at least 82%. In some cases, the conversion of a C1-carbon substrate into 2,3-BDO can be at least 83%. In some cases, the conversion of a C1-carbon substrate into 2,3-BDO can be at least 84%. In some cases, the conversion of a C1-carbon substrate into 2,3-BDO can be at least 85%. In some cases, the conversion of a C1-carbon substrate into 2,3-BDO can be at least 86%. In some cases, the conversion of a C1-carbon substrate into 2,3-BDO can be at least 87%. In some cases, the conversion of a C1-carbon substrate into 2,3-BDO can be at least 88%. In some cases, the conversion of a C1-carbon substrate into 2,3-BDO can be at least 89%. In some cases, the conversion of a C1-carbon substrate into 2,3-BDO can be at least 90%. In some cases, the conversion of a C1-carbon substrate into 2,3-BDO can be at least 91%. In some cases, the conversion of a C1-carbon substrate into 2,3-BDO can be at least 92%. In some cases, the conversion of a C1-carbon substrate into 2,3-BDO can be at least 93%. In some cases, the conversion of a C1-carbon substrate into 2,3-BDO can be at least 94%. In some cases, the conversion of a C1-carbon substrate into 2,3-BDO can be at least 95%. In some cases, the conversion of a C1-carbon substrate into 2,3-BDO can be at least 96%. In some cases, the conversion of a C1-carbon substrate into 2,3-BDO can be at least 97%. In some cases, the conversion of a C1-carbon substrate into 2,3-BDO can be at least 98%. In some cases, the conversion of a C1-carbon substrate into 2,3-BDO can be at least 99%.

In certain methods when producing 2,3-BDO, the concentration of 2,3-BDO in the fermentation broth is at least 1 g/L. For example, the concentration of 2,3-BDO produced in the fermentation broth can be from 1 g/L to 5 g/L, 2 g/L to 6 g/L, 3 g/L to 7 g/L, 4 g/L to 8 g/L, 5 g/L to 9 g/L, or 6 g/L to 10 g/L. In some cases, the concentration of 2,3-BDO can be at least 9 g/L. In some cases, the concentration of 2,3-BDO can be from 1 g/L to 5 g/L. In some cases, the concentration of 2,3-BDO can be from 2 g/L to 6 g/L. In some cases, the concentration of 2,3-BDO can be from 3 g/L to 7 g/L. In some cases, the concentration of 2,3-BDO can be from 4 g/L to 8 g/L. In some cases, the concentration of 2,3-BDO can be from 5 g/L to 9 g/L. In some cases, the concentration of 2,3-BDO can be from 6 g/L to 10 g/L.

In other cases, when microorganisms are used that normally produce at least some 2,3-BDO, after genetic modification and fermentation, the genetically modified microorganism can produce 2,3-BDO in concentrations that are at least 1.1× the amount that is normally produced. In some cases, the genetically modified microorganism can produce at least 2×, 3×, 4×, 5×, 6×, 7×, 8×, 9×, 10×, 15×, 20×, 25×, 30×, 35×, 40×, 45×, 50×, 60×, 70×, 80×, 90× or 100× the amount that is normally produced (e.g., produced by a microorganism that is unmodified and of the same species as the genetically modified microorganism). In some cases, the genetically modified microorganism can produce at least 2×, 3×, 4×, 5×, 10×, 25×, 50×, and or 100× the amount that is normally produced. In some cases, the genetically modified microorganism can produce at least 2× the amount that is normally produced. In some cases, the genetically modified microorganism can produce at least 3× the amount that is normally produced. In some cases, the genetically modified microorganism can produce at least 4× the amount that is normally produced. In some cases, the genetically modified microorganism can produce at least 5× the amount that is normally produced. In some cases, the genetically modified microorganism can produce at least 10× the amount that is normally produced. In some cases, the genetically modified microorganism can produce at least 25× the amount that is normally produced. In some cases, the genetically modified microorganism can produce at least 50× the amount that is normally produced. In some cases, the genetically modified microorganism can produce at least 100× the amount that is normally produced.

As discussed above, in certain cases the 2,3-BDO produced in the fermentation reaction is converted to MEK, butene, and/or butadiene (or other products) directly from the fermentation broth. In other cases, the 2,3-BDO is first recovered from the fermentation broth before conversion to MEK, butene, and/or butadiene.

In some cases, 2,3-BDO can be continuously removed from a portion of broth and recovered as purified 2,3-BDO.

In particular cases, the recovery of 2,3-BDO includes passing the removed portion of the broth containing 2,3-BDO through a separation unit to separate the microorganisms (e.g., genetically modified methanotroph) from the broth, to produce a cell-free 2,3-BDO containing permeate, and returning the microorganisms to the bioreactor. The cell-free 2,3-BDO-containing permeate may then can be stored or be used for subsequent conversion to butene, MEK and/or butadiene (or other desired product).

The recovering of 2,3-BDO and/or one or more other products or by-products produced in the fermentation reaction can comprise continuously removing a portion of the broth and recovering separately 2,3-BDO and one or more other products from the removed portion of the broth. In some cases the recovery of 2,3-BDO and/or one or more other products includes passing the removed portion of the broth containing 2,3-BDO and/or one or more other products through a separation unit to separate microorganisms from the 2,3-BDO and/or one or more other products, to produce a cell-free 2,3-BDO and one or more other product-containing permeate, and returning the microorganisms to the bioreactor.

In the above cases, the recovery of 2,3-BDO and one or more other products can include first removing 2,3-BDO from the cell-free permeate followed by removing the one or more other products from the cell-free permeate. The cell-free permeate can also then be returned to the bioreactor.

2,3-BDO, or a mixed product stream containing 2,3-BDO, can be recovered from the fermentation broth. For example, methods that can be used can include but are not limited to, fractional distillation or evaporation, pervaporation, and extractive fermentation. Further examples include: recovery using steam from whole fermentation broths; reverse osmosis combined with distillation; Liquid-liquid extraction techniques involving solvent extraction of 2,3-BDO; aqueous two-phase extraction of 2,3-BDO in PEG/dextran system; solvent extraction using alcohols or esters, e.g., ethyl acetate, tributylphosphate, diethyl ether, n-butanol, dodecanol, oleyl alcohol, and an ethanol/phosphate system; aqueous two-phase systems composed of hydrophilic solvents and inorganic salts. See generally, Voloch, M., et al., (1985) and U.S. Pat. Pub. Appl. No. 2012/0045807.

In some cases prior to exposure to solvent, the fermentation broth is dewatered by evaporation or both microfiltration and reverse osmosis because of the low partition coefficient and the low selectivity of 2,3-BDO. Repulsive extraction or salting out using potassium chloride (KCl) or dehydrated $K_2CO_3$ has also been investigated on the recovery of 2,3-BD (Syu 2001) like the salting-out effect of $K_2CO_3$ on extraction of butanol in acetone-O butanol-ethanol fermentation. The removal of water from the fermentation broth was also tested before salting out because the concentration of 2,3-BDO in the broth was too low to be salted out even if at a saturated KCl or $K_2CO_3$ solution. See generally, U.S. Pat. Pub. Appl. No. 2012/0045807.

A yet further example of a method to recover 2,3-BDO is to react it with formaldehyde to form a formal under catalysis of acid. The 2,3-BDO formal is collected in the top oil phase and allowed to react with acid methanol to form 2,3-BDO and methylal. Methylal can be hydrolyzed to methanol and formaldehyde. See generally, U.S. Pat. Pub. Appl. No. 2012/0045807.

A further example, may be the use of ionic liquids to extract the ethanol/2,3-BD from clarified broth. Ionic liquids can be tailored in many ways to change physical properties. An advantage of this approach is that ionic liquids are not volatile. Some are water sensitive but others are not.

Pervaporation or vacuum membrane distillation, used previously in ethanol and butanol fermentations, can be used to concentrate 2,3-BDO in water as an extract from the fermentation broth. A microporous polytetrafluoroethylene (PTFE) membrane is used in the integrated process, while a silicone membrane is usually used in pervaporative ethanol or butanol fermentations. See generally, U.S. Pat. Pub. Appl. No. 2012/0045807.

By-products such as acids including acetate and butyrate may also be recovered from the fermentation broth using methods known in the art. For example, an adsorption system involving an activated charcoal filter or electrodialysis can be used.

In certain cases of the invention, 2,3-BDO and by-products are recovered from the fermentation broth by continuously removing a portion of the broth from the bioreactor, separating microbial cells from the broth (conveniently by filtration, for example), and recovering 2,3-BDO and optionally other alcohols and acids from the broth. Alcohols may conveniently be recovered for example by distillation, and acids may be recovered for example by adsorption on activated charcoal. The separated microbial cells can be returned to the fermentation bioreactor. The cell free permeate remaining after the alcohol(s) and acid(s) have been removed can also be returned to the fermentation bioreactor. Additional nutrients may be added to the cell free permeate to replenish the nutrient medium before it is returned to the bioreactor.

Also, if the pH of the broth was adjusted during recovery of 2,3-BDO and/or by-products, the pH should be re-adjusted to a similar pH to that of the broth in the fermentation bioreactor, before being returned to the bioreactor.

In certain cases, the 2,3-BDO is continuously recovered from the fermentation broth or bioreactor and fed directly for chemical conversion to one or more of butene, butadiene and methyl ethyl ketone. For example, the 2,3-BDO may be fed directly through a conduit to one or more vessel suitable for chemical synthesis of one or more of butene, butadiene and methyl ethyl ketone or other down-stream chemical products.

While some cases have been shown and described herein, such cases are provided by way of example only. Numerous variations, changes, and substitutions will now occur to those skilled in the art without departing from the invention. It should be understood that various alternatives to the cases of the invention described herein will be employed in practicing the invention.

EXAMPLES

Example 1: Genetic Engineering of Methanotrophs

To engineer a methanotroph to produce 2,3-BDO, we started with *M. capsulatus* and tested several 2,3-BDO biosynthetic genes from *Bacillus subtilis, Clostridium autoethanogenum, Klebsiella pneumoniae*, and *Paenibacillus polymyxa*. Table 1 below shows the genes tested and the origin of the genes.

TABLE 1

| Gene category | | Gene name | Microbial species |
|---|---|---|---|
| 2,3-BDO pathyway genes | AlsS | BsuAlsS | *Bacillus subtilis* |
| | | CauAlsS | *Clostridium autoethanogenum* |
| | BudA | CauBudA | *Clostridium autoethanogenum* |
| | | KpnBudA | *Klebsiella pneumoniae* |

TABLE 1-continued

| Gene category | Gene name | Microbial species |
|---|---|---|
| ButA | CauButA | *Clostridium autoethanogenum* |
| | BsuButA | *Bacillus subtilis* |
| | PpoButA | *Paenibacillus polymyxa* |

For the first gene of the pathway, AlsS, which encodes for an enzyme that coverts two molecules of pyruvate into 2-acetolactate, we tested AlsS homologs from *Bacillus subtilis* and *Clostridium autoethanogenum*. For the second gene in the pathway, BudA, which encodes for an enzyme that converts 2-acetolactate into acetoin, we tested BudA homologs from *Clostridium autoethanogenum* and *Klebsiella pneumonia*. For the third gene in the pathway, ButA, which encodes an enzyme that converts acetoin into 2,3-BDO using NAD(P)H as a reduced cofactor, we tested ButA homologs from *Clostridium autoethanogenum* (NADPH-dependent), *Bacillus subtilis* (NADH-dependent), and *Paenibacillus polymyxa* (NADH-dependent).

We generated 48 different broad host plasmids containing variations in the 3-gene 2,3-BDO pathway, as shown in Table 2 (below in Example 2). Table 2 shows the genotypes of the resulting engineered strains.

Example 2: 2,3-BDO Productivity

We transformed the aforementioned plasmids (in Example 1) into a transformation competent methanotroph strain, RL83A, and evaluated 74 resulting strains (including biological replicate strains) for 2,3-BDO production in small scale microtiter plate fermentation using methane as the carbon source.

As shown in Table 2, the constructs that constitutively expressed AlsS genes resulted in either no transformants or no production of 2,3-BDO, indicating that there was a negative impact when AlsS genes were strongly and constitutively expressed. The results showed that the strains that produced the most 2,3-BDO contained the gene combinations BsuAlsA-KpnBudA-CauButA or BsuAlsA-KpnBudA-BsuButA (Table 2).

TABLE 2

| DNA construct | Genotype* | | | | | Resulted *M. capsulatus* Strain ** | | 2,3BDO production in Tier1 assay (mg/L) | |
|---|---|---|---|---|---|---|---|---|---|
| asm178.1 | pBAD | BsuAlsS | CauBudA | CauButA | | XZ01 | NT | 55.4 | / |
| asm178.2 | pBAD | BsuAlsS | CauBudA | BsuButA | | XZ02 | XZ03 | 49.6 | 49.9 |
| asm178.3 | pBAD | BsuAlsS | CauBudA | PpoButA | | XZ04 | XZ05 | 47.2 | 48 |
| asm178.4 | pBAD | BsuAlsS | KpnBudA | CauButA | | XZ06 | XZ07 | 179.6 | 175.6 |
| asm178.5 | pBAD | BsuAlsS | KpnBudA | BsuButA | | XZ08 | XZ09 | 135.9 | 132.4 |
| asm178.6 | pBAD | BsuAlsS | KpnBudA | PpoButA | | XZ10 | XZ11 | 28.3 | 27.5 |
| asm178.7 | pBAD | CauAlsS | CauBudA | CauButA | | XZ12 | XZ13 | 2.1 | 1.8 |
| asm178.8 | pBAD | CauAlsS | CauBudA | BsuButA | | XZ14 | XZ15 | 1.9 | 1.6 |
| asm178.9 | pBAD | CauAlsS | CauBudA | PpoButA | | XZ16 | XZ17 | 0 | 0 |
| asm178.10 | pBAD | CauAlsS | KpnBudA | CauButA | | XZ18 | XZ19 | 79.2 | 75.2 |
| asm178.11 | pBAD | CauAlsS | KpnBudA | BsuButA | | XZ20 | XZ21 | 50.1 | 49.7 |
| asm178.12 | pBAD | CauAlsS | KpnBudA | PpoButA | | XZ22 | XZ23 | 2.4 | 1.8 |
| asm178.13 | pMxaF | BsuAlsS | CauBudA | CauButA | | NT | NT | / | / |
| asm178.14 | pMxaF | BsuAlsS | CauBudA | BsuButA | | NT | NT | / | / |
| asm178.15 | pMxaF | BsuAlsS | CauBudA | PpoButA | | NT | NT | / | / |
| asm178.16 | pMxaF | BsuAlsS | KpnBudA | CauButA | | NT | NT | / | / |
| asm178.17 | pMxaF | BsuAlsS | KpnBudA | BsuButA | | NT | NT | / | / |
| asm178.18 | pMxaF | BsuAlsS | KpnBudA | PpoButA | | NT | NT | / | / |
| asm178.19 | pMxaF | CauAlsS | CauBudA | CauButA | | XZ29 | XZ30 | 0 | 0 |
| asm178.20 | pMxaF | CauAlsS | CauBudA | BsuButA | | XZ31 | XZ32 | 0 | 0 |
| asm178.21 | pMxaF | CauAlsS | CauBudA | PpoButA | | XZ33 | XZ34 | 0 | 0 |
| asm178.22 | pMxaF | CauAlsS | KpnBudA | CauButA | | XZ35 | NT | 0 | / |
| asm178.23 | pMxaF | CauAlsS | KpnBudA | BsuButA | | XZ36 | NT | 0 | / |
| asm178.24 | pMxaF | CauAlsS | KpnBudA | PpoButA | | XZ37 | XZ38 | 0 | 0 |
| asm178.25 | pMxaF | BsuAlsS | CauBudA | p.Bba.123111 | CauButA | XZ39 | XZ40 | 8.4 | 0 |
| asm178.26 | pMxaF | BsuAlsS | CauBudA | p.Bba.123111 | BsuButA | XZ41 | XZ42 | 0 | 0 |
| asm178.27 | pMxaF | BsuAlsS | CauBudA | p.Bba.123111 | PpoButA | XZ43 | XZ44 | 0 | 0 |
| asm178.28 | pMxaF | BsuAlsS | KpnBudA | p.Bba.123111 | CauButA | NT | NT | / | / |
| asm178.29 | pMxaF | BsuAlsS | KpnBudA | p.Bba.123111 | BsuButA | XZ45 | NT | 11.6 | / |
| asm178.30 | pMxaF | BsuAlsS | KpnBudA | p.Bba.123111 | PpoButA | XZ46 | NT | 0 | / |
| asm178.31 | pMxaF | CauAlsS | CauBudA | p.Bba.123111 | CauButA | XZ47 | XZ48 | 0 | 0 |
| asm178.32 | pMxaF | CauAlsS | CauBudA | p.Bba.123111 | BsuButA | XZ49 | XZ50 | 0 | 0 |
| asm178.33 | pMxaF | CauAlsS | CauBudA | p.Bba.123111 | PpoButA | XZ51 | XZ52 | 0 | 0 |
| asm178.34 | pMxaF | CauAlsS | KpnBudA | p.Bba.123111 | CauButA | NT | NT | / | / |
| asm178.35 | pMxaF | CauAlsS | KpnBudA | p.Bba.123111 | BsuButA | NT | NT | / | / |
| asm178.36 | pMxaF | CauAlsS | KpnBudA | p.Bba.123111 | PpoButA | NT | NT | / | / |
| asm178.37 | pBAD | BsuAlsS | CauBudA | pMxaF | CauButA | NT | NT | / | / |
| asm178.38 | pBAD | BsuAlsS | CauBudA | pMxaF | BsuButA | XZ53 | XZ54 | 64.6 | 68.7 |
| asm178.39 | pBAD | BsuAlsS | CauBudA | pMxaF | PpoButA | XZ55 | XZ56 | 47.4 | 32.6 |
| asm178.40 | pBAD | BsuAlsS | KpnBudA | pMxaF | CauButA | XZ57 | XZ58 | 180.8 | 194.3 |
| asm178.41 | pBAD | BsuAlsS | KpnBudA | pMxaF | BsuButA | XZ59 | XZ60 | 144.4 | 125.9 |
| asm178.42 | pBAD | BsuAlsS | KpnBudA | pMxaF | PpoButA | XZ61 | XZ62 | 1.8 | 2.7 |
| asm178.43 | pBAD | CauAlsS | CauBudA | pMxaF | CauButA | XZ63 | XZ64 | 1.8 | 1.7 |
| asm178.44 | pBAD | CauAlsS | CauBudA | pMxaF | BsuButA | XZ65 | XZ66 | 1.5 | 1.8 |
| asm178.45 | pBAD | CauAlsS | CauBudA | pMxaF | PpoButA | XZ67 | XZ68 | 0 | 0 |
| asm178.46 | pBAD | CauAlsS | KpnBudA | pMxaF | CauButA | XZ69 | XZ70 | 83.3 | 78.5 |
| asm178.47 | pBAD | CauAlsS | KpnBudA | pMxaF | BsuButA | XZ71 | XZ72 | 39.2 | 38.3 |
| asm178.48 | pBAD | CauAlsS | KpnBudA | pMxaF | PpoButA | XZ73 | XZ74 | 2 | 1.6 |

Figure 2:
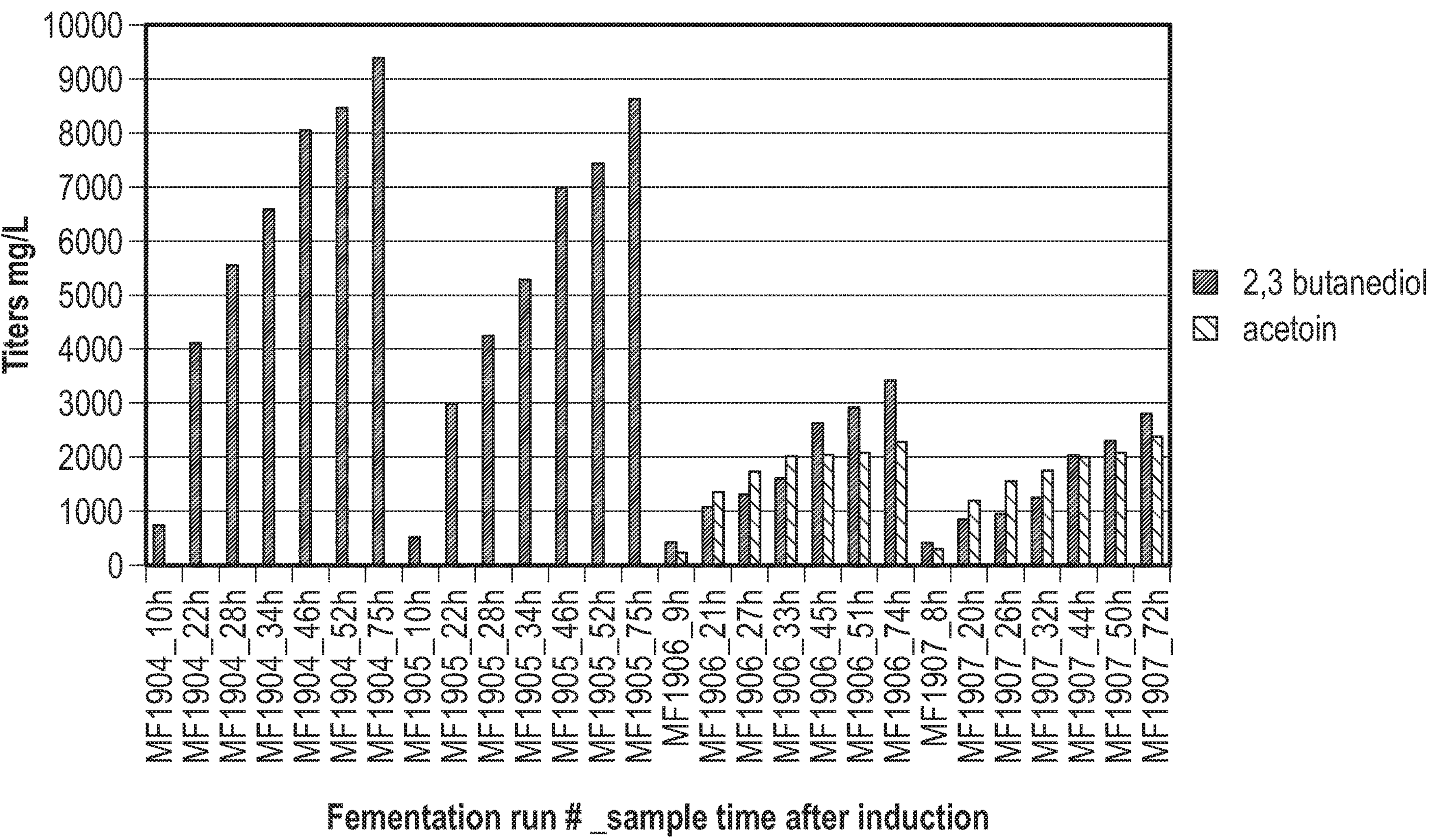
FIG. 2 shows the performance of engineered strains in a high-cell density fermentation experiment over 72 hours. From left to right are the following strains that were tested: XZ58 (MF1904), XZ06 (MF1905), XZ59(MF1906), and XZ08 (MF1907). 2,3-BDO and acetoin production was tested at various time points.

To confirm the results from the primary microplate assay, we evaluated four top strains, XZ58 and XZ06 (BsuAlsA-KpnBudA-CauButA), XZ59 and XZ08 (BsuAlsA-Kpn-BudA-BsuButA), in a high cell-density fermentation experiment in a 1 L bioreactor. As shown in FIG. 2, strains XZ58 and XZ06 produced 9.3 g/L and 8.5 g/L 2,3-BDO, respectively, with no penultimate product, acetoin, produced (FIG. 2, left panel). The data demonstrates that strains expressing NADPH-dependent acetoin reductase (CauButA) produce exclusively 2,3-BDO with no acetoin co-product. In contrast, strains expressing NADH-dependent acetoin reductase produced a significant amount of the 2,3-BDO precursor, acetoin (FIG. 2, right panel). Inefficient conversion of acetoin to 2,3-BDO with NADH-dependent pathways could be due to either poor enzyme expression or low NADH precursor pools in *M. capsulatus*.

Example 3: Genetic Switches Used for 2,3-BDO Production

In order to effectively control 2,3-BDO production at specific times, a genetic switch system was implemented. Methanotrophs were transformed with genes placed under the control of a lanthanum “switch”. Lanthanum switches repress expression of genes in the presence of the metal lanthanum. Upon removal or dilution of lanthanum in the media, the repressed genes are “switched” on.

Different strains of methanotrophs (as shown in Table 3 below shows the strains and genotype of the strains) were pre-culturing in the presence of 10 μM lanthanum.

TABLE 3

| Strain | Genotype |
|---|---|
| XZ685<br>XZ686<br>XZ687 | pmxaF > Bsu.alsA > rbs.GTW0001_Kpn.BudA > rbs.GTW0001_Cau.ButA |
| XZ688<br>XZ689<br>XZ690 | pmxaF > Bsu.alsA > rbs.Mca.mxaF_Kpn.BudA > rbs.Mca.mxaF_Cau.ButA |
| XZ691<br>XZ692<br>XZ693 | pmxaF > Blic.alsA > rbs.GTW0001_Kpn.BudA > rbs.GTW0001_Cau.ButA |
| XZ694<br>XZ695<br>XZ696 | pmxaF > Blic.alsA > rbs.Mca.mxaF_Kpn.BudA > rbs.Mca.mxaF_Cau.ButA |
| XZ697<br>XZ698<br>XZ699 | pmxaF > Bsu.alsA > rbs.GTW0001_Kpn.BudA > rbs.GTW0001_Cau.ButA |
| XZ700<br>XZ701<br>XZ702 | pmxaF > Bsu.alsA > rbs.Mca.mxaF_Kpn.BudA > rbs.Mca.mxaF_Cau.ButA |
| XZ703<br>XZ704<br>XZ705 | pmxaF > Blic.alsA > rbs.Mca.mxaF_Kpn.BudA > rbs.Mca.mxaF_Cau.ButA |

After growing precultures to ~3 OD600, the medium containing lanthanum was diluted at a ratio of 1:10 (lanthanum containing media: non-lanthanum containing media) or 1:50. After 96 or 120 hours, the cultures assessed for production of 2,3-BDO and acetoin (FIG. 7A, 96 hours) or (FIG. 7B, 120 hours). Shown below in Table 4 are strains, dilution levels, acetoin production titers after 96 hours, 2,3-BDO production titers after 96 hours, acetoin production titers after 120 hours, and 2,3-BDO production titers after 120 hours.

TABLE 4

| | Strain | Dilution | Acetoin (mg/L)_ 96h | 2,3BDO (mg/L)_ 96h | Acetoin (mg/L)_ 120h | 2,3BDO (mg/L)_ 120h |
|---|---|---|---|---|---|---|
| 1 | XZ685 | 10X | 5.847 | 71.342 | 8.617 | 150.864 |
| 2 | XZ686 | 10X | 4.86 | 51.439 | 10.539 | 135.871 |
| 3 | XZ687 | 10X | 6.306 | 53.591 | 10.475 | 137.104 |
| 4 | XZ688 | 10X | 5.311 | 73.08 | 8.79 | 158.947 |
| 5 | XZ689 | 10X | 5.282 | 71.059 | 6.944 | 149.219 |
| 6 | XZ690 | 10X | 5.679 | 51.291 | 13.412 | 165.688 |
| 7 | XZ691 | 10X | 4.014 | 0 | 0 | 19.231 |
| 8 | XZ692 | 10X | 3.719 | 4.679 | 7.984 | 23.991 |
| 9 | XZ693 | 10X | 3.778 | 4.082 | 6.2 | 18.78 |
| 10 | XZ694 | 10X | 43.925 | 0 | 54.582 | 4.871 |
| 11 | XZ695 | 10X | 44.734 | 0 | 55.632 | 3.363 |
| 12 | XZ696 | 10X | 46.473 | 0 | 57.444 | 5.39 |
| 13 | XZ697 | 10X | 5.982 | 48.549 | 12.221 | 131.618 |
| 14 | XZ698 | 10X | 3.441 | 52.775 | 12.594 | 137.996 |
| 15 | XZ699 | 10X | 5.747 | 44.14 | 12.937 | 131.699 |
| 16 | XZ700 | 10X | 5.101 | 50.998 | 12.26 | 117.653 |
| 17 | XZ701 | 10X | 4.82 | 52.523 | 12.167 | 120.369 |
| 18 | XZ702 | 10X | 5.802 | 54.763 | 12.119 | 133.294 |
| 19 | XZ703 | 10X | 38.501 | 0 | 51.296 | 6.482 |
| 20 | XZ704 | 10X | 33.64 | 0 | 44.195 | 5.021 |
| 21 | XZ705 | 10X | 40.326 | 0 | 52.443 | 5.978 |
| 22 | XZ685 | 50X | 4.245 | 95.288 | 8.993 | 184.974 |
| 23 | XZ686 | 50X | 3.028 | 87.876 | 0 | 173.315 |
| 24 | XZ687 | 50X | 4.341 | 85.562 | 10.06 | 193.196 |
| 25 | XZ688 | 50X | 4.088 | 73.804 | 8.181 | 156.027 |
| 26 | XZ689 | 50X | 4.273 | 78.782 | 0 | 156.435 |
| 27 | XZ690 | 50X | 4.383 | 79.226 | 7.879 | 155.869 |
| 28 | XZ691 | 50X | 3.178 | 10.35 | 8.197 | 32.164 |
| 29 | XZ692 | 50X | 2.838 | 14.16 | 7.839 | 38.733 |
| 30 | XZ693 | 50X | 2.865 | 12.942 | 9.163 | 41.967 |
| 31 | XZ694 | 50X | 53.138 | 0 | 64.47 | 4.259 |
| 32 | XZ695 | 50X | 66.256 | 0 | 79.665 | 4.736 |
| 33 | XZ696 | 50X | 66.139 | 0 | 78.46 | 4.746 |
| 34 | XZ697 | 50X | 4.664 | 57.939 | 9.411 | 122.655 |
| 35 | XZ698 | 50X | 5.749 | 67.055 | 10.424 | 151.002 |
| 36 | XZ699 | 50X | 4.182 | 63.379 | 10.386 | 137.577 |
| 37 | XZ700 | 50X | 3.558 | 59.187 | 9.519 | 121.163 |
| 38 | XZ701 | 50X | 3.085 | 63.574 | 10.265 | 140.806 |
| 39 | XZ702 | 50X | 5.039 | 66.163 | 11.252 | 131.931 |
| 40 | XZ703 | 50X | 58.687 | 0 | 72.718 | 6.653 |
| 41 | XZ704 | 50X | 55.523 | 0 | 70.855 | 6.577 |
| 42 | XZ705 | 50X | 59.577 | 0 | 76.618 | 4.793 |

Figure 7A:
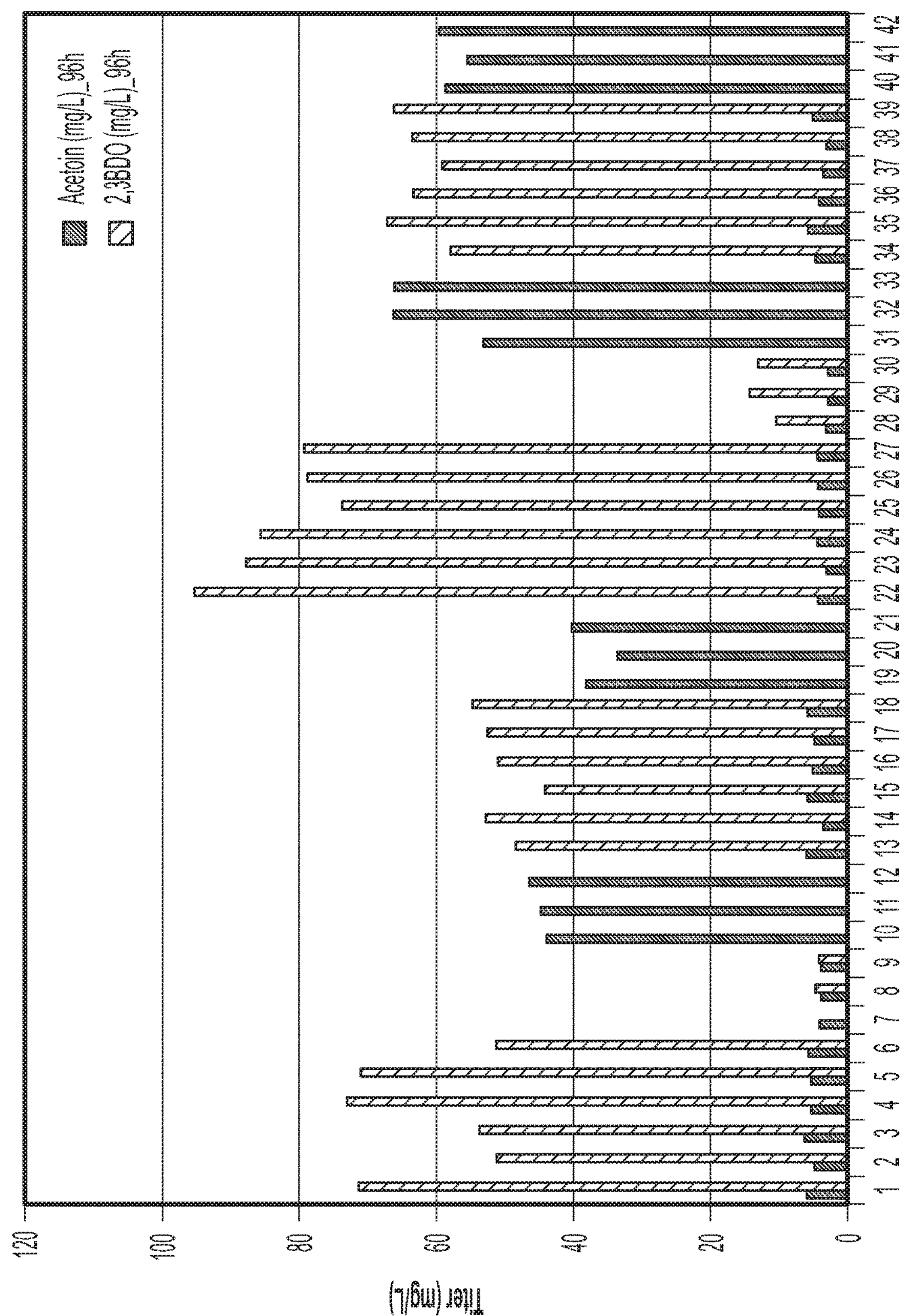
FIGS. 7A and 7B.
Figure 7B:
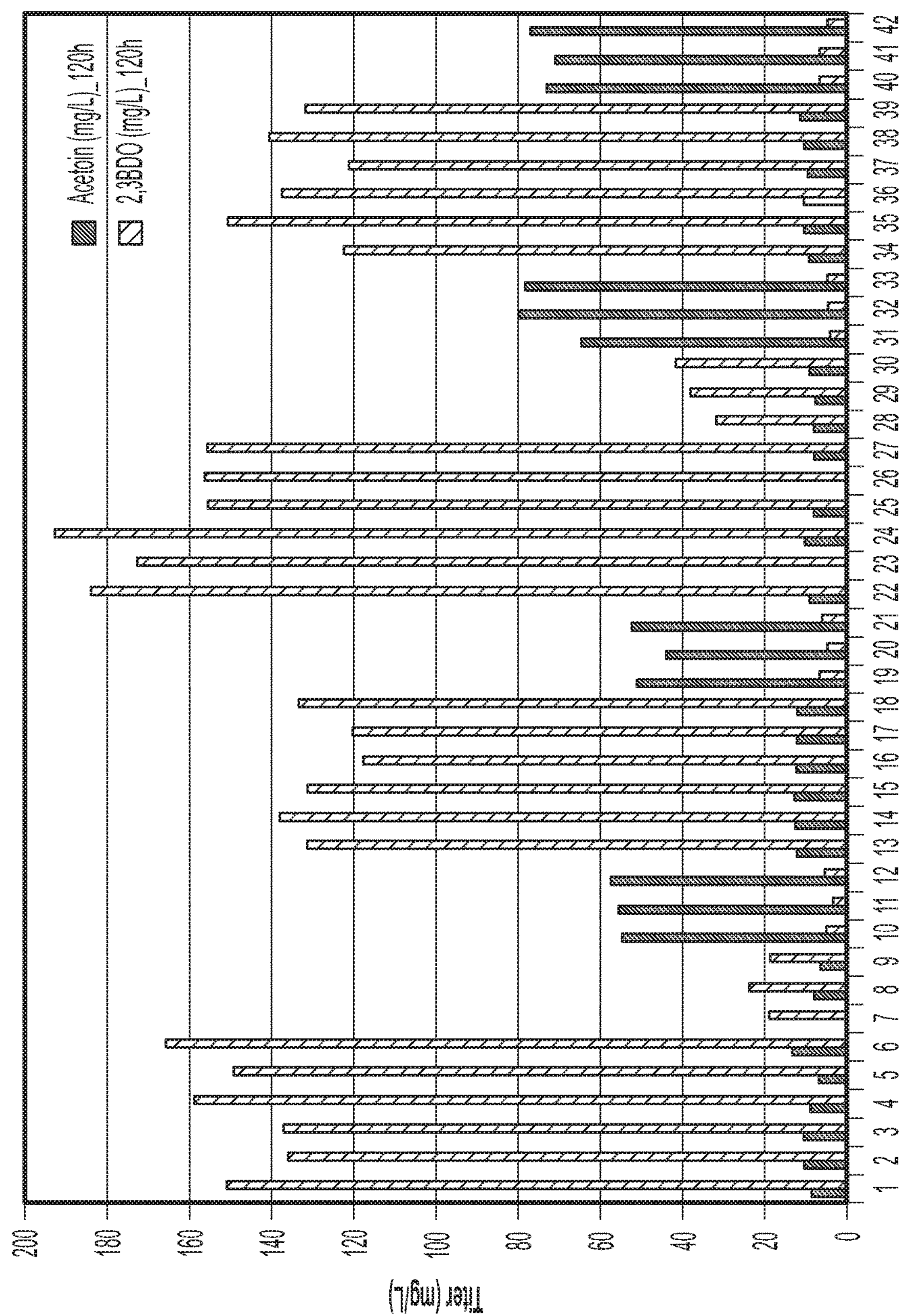

As shown FIGS. 7A, 7B, and Table 4, strains XZ685, XZ686, XZ687, XZ688, XZ689, and XZ690 (referring to 22 to 27, respectively in FIGS. 7A and 7B) produced the highest titers of 2,3-BDO at both 96 and 120 hours when diluting the lanthanum containing medium 1:50 (50×). Using a 1:10 dilution protocol also resulted in significant production of 2,3-BDO but the titers were lower than those using the 1:50 dilution protocol at both 96 and 120 hours. Strains XZ697, XZ698, XZ699, XZ700, XZ701, and XZ702 (referring to 34 to 39, respectively in FIGS. 7A and 7B) produced lower titers at both 1:10 and 1:50 dilutions at both 96 and 120 hours.

Example 4: Acetolactate Synthase

The plasmids described in Table 5 (below), were transformed into a transformation competent methanotroph strain. The resulting strains were tested for 2,3-BDO production titers in small scale microtiter plate fermentation using methane as the carbon source.

TABLE 5

| Strain | Strain Genotype | Average Titer (mg/L) | % diff. vs. XZ58 |
|---|---|---|---|
| XZ58 | p.BAD > g.Bsu.alsS > (rbs.GTW0001)g.Kpn.BudA > p.mxaF > g.Cau.ButA | 372 | 0.0% |
| XZ557 | p.BAD > g.Blic.alsS –> (rbs.GTW0001)g.Kpn.BudA – p.mxaF > g.Cau.ButA | 421 | 16.1% |
| XZ546 | p.BAD > g.Bsu.alsS–(rbs.Mca.MxaF)g.Kpn.BudA – p.mxaF > g.Cau.ButA | 373 | 0.3% |
| XZ562 | p.BAD > g.Blic.alsS–(rbs.Mca.MxaF)g.Kpn.BudA – p.mxaF > g.Cau.ButA | 538 | 44.6% |

Figure 8:
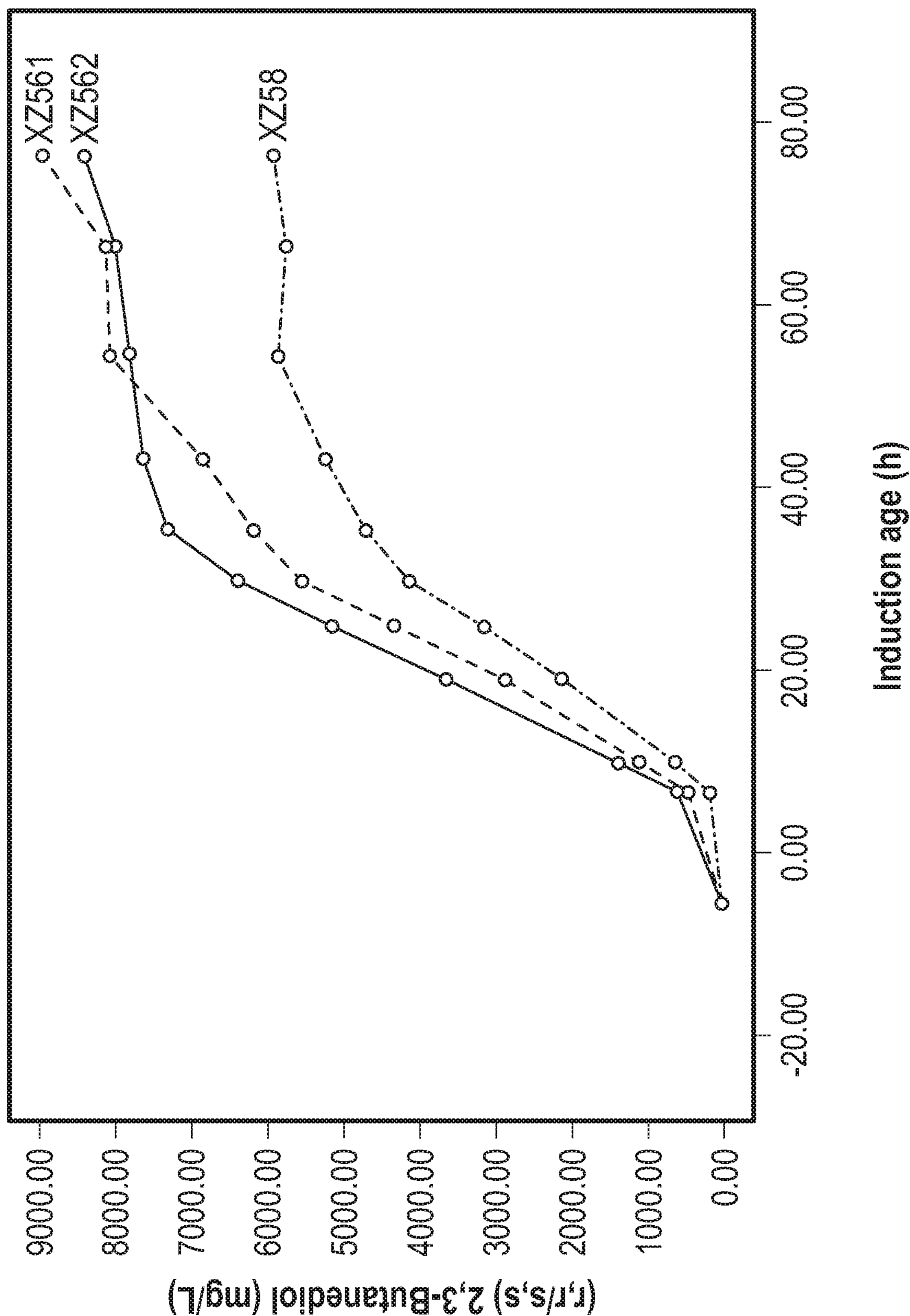
FIG. 8 shows that strains expressing a *Bacillus licheniformis* AlsS exhibited significantly improved 2,3-BDO titers. In one strain expressing *Bacillus licheniformis* AlsS (XZ562) the 2,3-BDO titers increased an average of 44.6% over the XZ58 strain (described in FIG. 3) over the fermentation run. Another biological replicate (XZ561), produced also significantly higher average 2,3-BDO titers compared to the XZ58 strain.

As shown in Table 5 and in FIG. 8, the strains that expressed *Bacillus licheniformis* AlsS gene, showed better 2,3-BDO production titers than the strains that expressed *Bacillus subtilis* AlsS (e.g., the strains described in Example 2). In one example, a strain that has a substitution of only the AlsS gene (e.g., strains XZ557) exhibited an increase of 2,3-BDO production titer of up to 16.1% compared to strain XZ58. In another sample, strain XZ546, a strain having a substitution of only the ribosome binding site for the Kpn-.BudA gene, showed virtually no increase of 2,3-BDO titers compared with strain XZ58. However, remarkably, a strain that contained rbs.Mca.MxaF for the Kpn.BudA, instead of a rbs.GTW0001 and expressed a *Bacillus licheniformis* AlsS gene (e.g., strain XZ562), exhibited a significant increase in 2,3-BDO titers, up to 44.6% compared to strain XZ58.

Example 5: Temperature During Fermentation

In order to prevent instability sometimes present in plasmid expressing strains, we generated strains with 2,3-BDO pathway genes integrated in chromosome at the Glgc locus. A total of 21 strains were generated.

Seven of the strains were tested in shake bottles for their ability to produce 2,3-BDO at 37° C. and at 42° C. Fermentation occurred over a 96 hour period. The genotypes of the strains are presented in TABLE 6 below:

TABLE 6

| | Strain | Background | Genotypes | | | | | |
|---|---|---|---|---|---|---|---|---|
| Integrated | MBC2115 | RL83 | p.Mcap.mxaF | cds.Bsub.AlsS | rbs.synt.GTW0001 | cds.Kpne.BudA | rbs.synt.GTW0001 | cds.Caut.ButA |
| Integrated | MBC2116 | RL83 | p.Mcap.mxaF | cds.Bsub.AlsS | rbs.synt.GTW0001 | cds.Kpne.BudA | rbs.synt.GTW0001 | cds.Caut.ButA |
| Integrated | MBC2117 | RL83 | p.Mcap.mxaF | cds.Bsub.AlsS | rbs.synt.GTW0001 | cds.Kpne.BudA | rbs.synt.GTW0001 | cds.Caut.ButA |
| Integrated | MBC2122 | RL83 | p.Mcap.mxaF | cds.Caut.ButA | rbs.Mcap.MXaF | cds.Kpne.BudA | rbs.Mcap.MxaF | cds.Blic.Als |
| Integrated | MBC2131 | XZ715 | p.Mcap.mxaF | cds.Caut.ButA | rbs.Mcap.MXaF | cds.Kpne.BudA | rbs.Mcap.MxaF | cds.Bsub.AlsS |
| Episomal | XZ685 | RL83 | p.Mcap.mxaF | cds.Bsub.AlsS | rbs.synt.GTW0001 | cds.Kpne.BudA | rbs.synt.GTW0001 | cds.Caut.ButA |
| Episomal | MBC1322 | MH436 | p.Mcap.mxaF | cds.Bsub.AlsS | rbs.synt.GTW0001 | cds.Kpne.BudA | rbs.synt.GTW0001 | cds.Caut.ButA |

Figure 9:
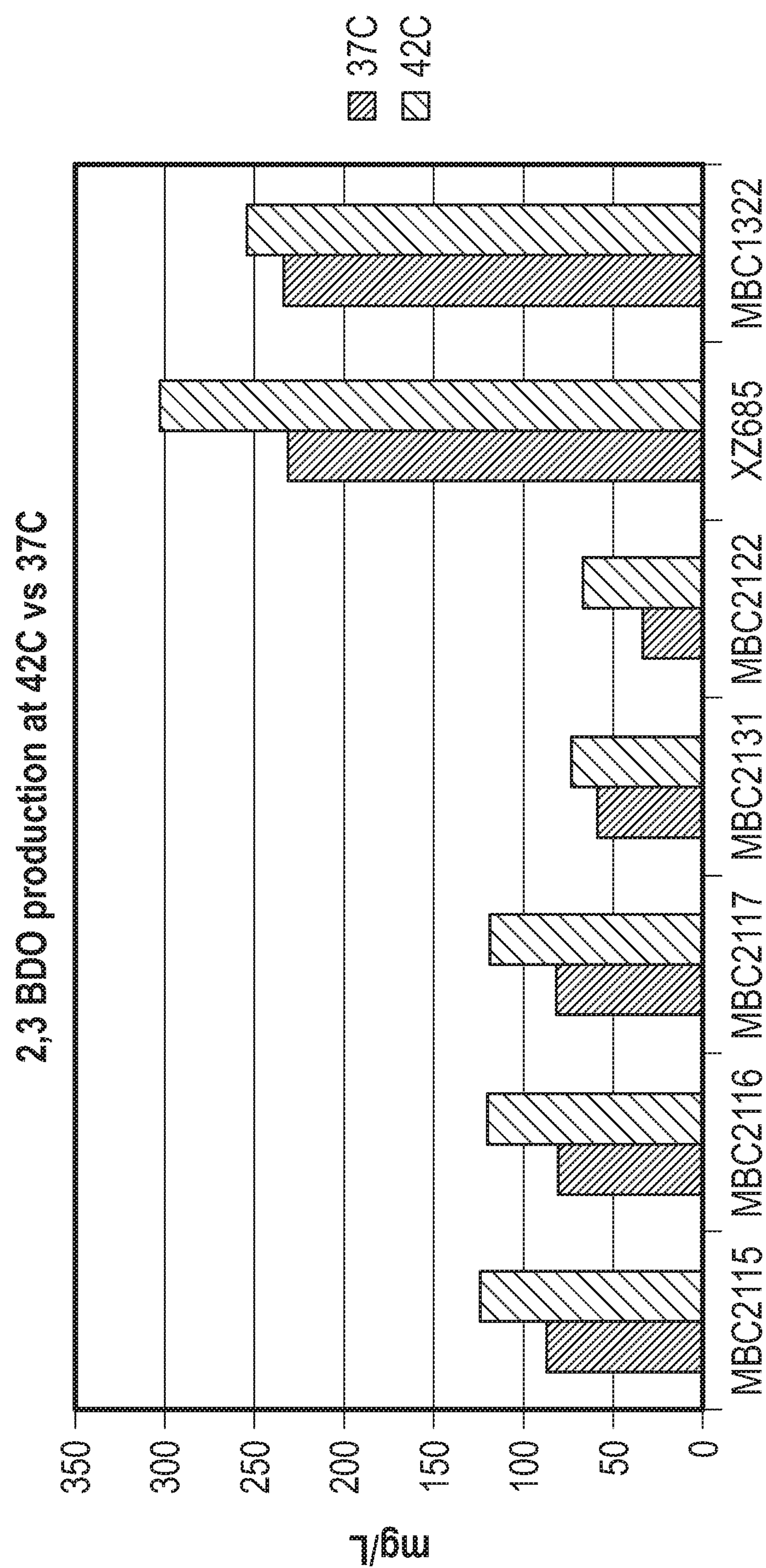
FIG. 9 shows 2,3-BDO titers of 7 strains of methanotrophs genetically engineered to produce 2,3-BDO fermented at either 42° C. or 37° C. As seen, all strains produced higher 2,3-BDO titers when incubated at 42° C. Strain MBC2122 produced approximately 50% more 2,3-BDO at 42° C. compared to at 37° C.

As seen in FIG. 9, all strains tested produced significantly more 2,3-BDO when fermentation occurred at 42° C. Some strains, such as MBC2122, produced approximately double the amount of 2,3-BDO at 42° C. rather than 37° C.

Figure 10:
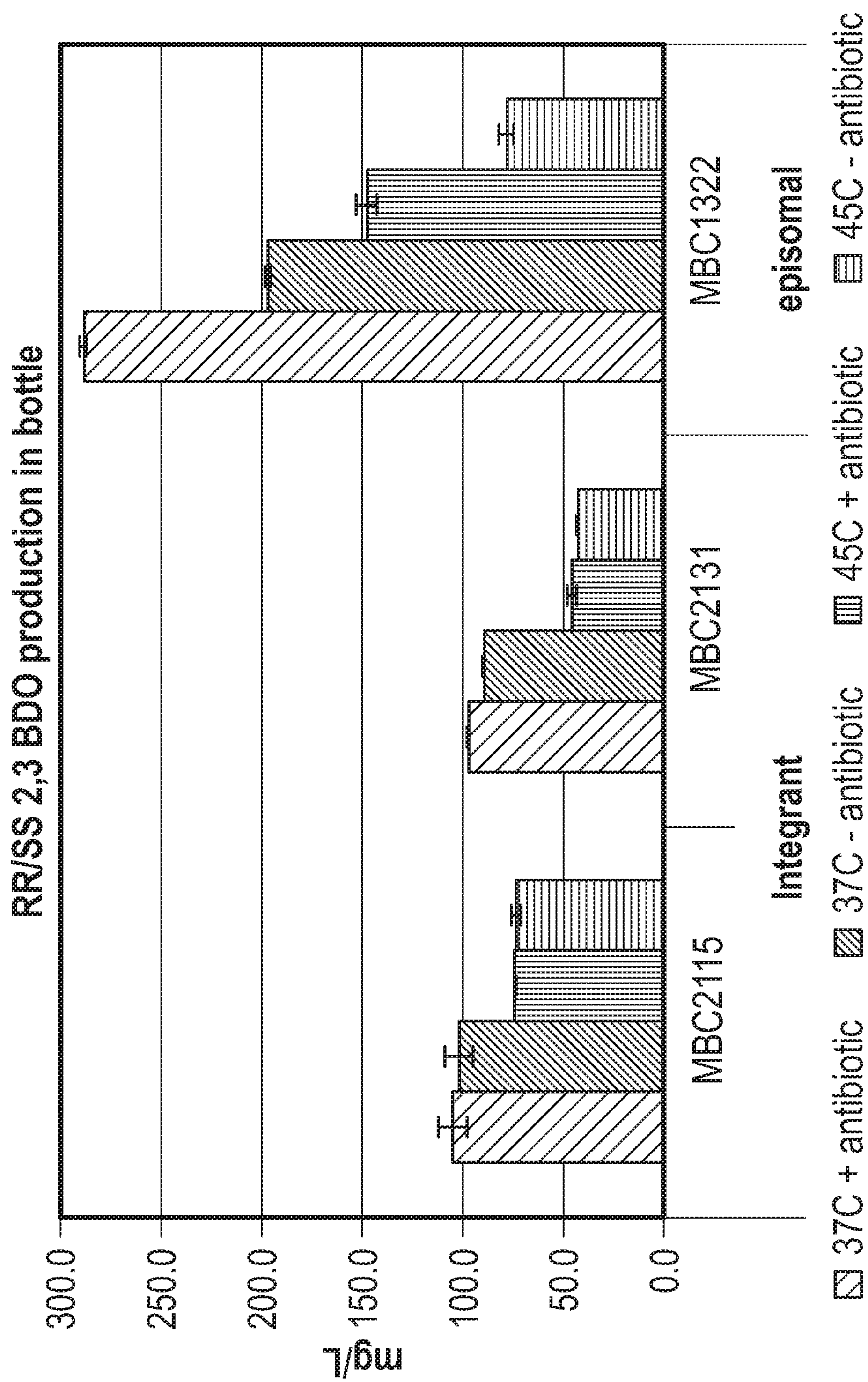
FIG. 10 shows 2,3-BDO titers of 3 strains of methanotrophs genetically engineered to produce 2,3-BDO fermented at either 45° C. or 37° C. As seen, all strains produced lower 2,3-BDO titers when incubated at 45° C. Most of the strains produced approximately 50% less 2,3-BDO at 45° C. compared to at 37° C. The episomal strain MBC1322 performed better with antibiotic selective pressure, at both 37° C. and 45° C., indicating a stability issue. On the contrary, the integrated strains were able to maintain its productivity without selective pressure.

Three of the strains were further tested when fermented at 45° C., with and without antibiotic selective pressure. Compared to the same strain incubated at 37° C., the strains that were fermented at 45° C. produced significantly less 2,3-BDO. See FIG. 10. The episomal strain MBC1322 performed better with antibiotic selective pressure, at both 37° C. and 45° C., indicating a stability issue. On the contrary, the integrated strains were able to maintain its productivity without selective pressure.

Figure 11:
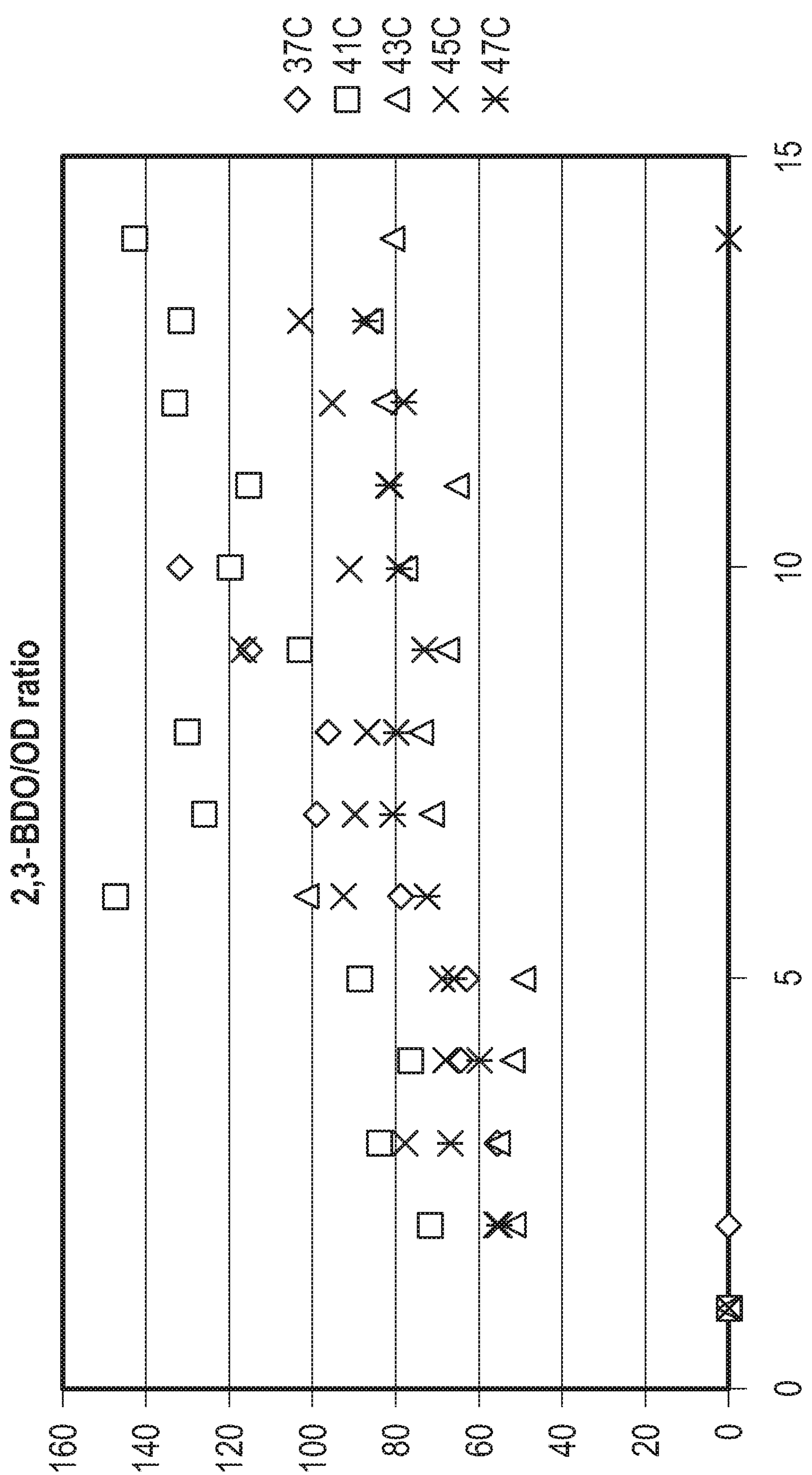
FIG. 11 shows the productivity (2,3-BDO/OD ratio) of a methanotroph strain genetically engineered to produce 2,3-BDO fermented at 37° C., 41° C., 43° C., 45° C., and 47° C. The best productivity was observed at a temperature of 41° C.

Additionally testing was performed at 37° C., 41° C., 43° C., 45° C., and 47° C. 2,3-BDO titers and OD rations were calculated. As seen in FIG. 11 the best productivity was observed at a temperature of 41° C.

Example 6: Additional Gene Copies

Figure 12:
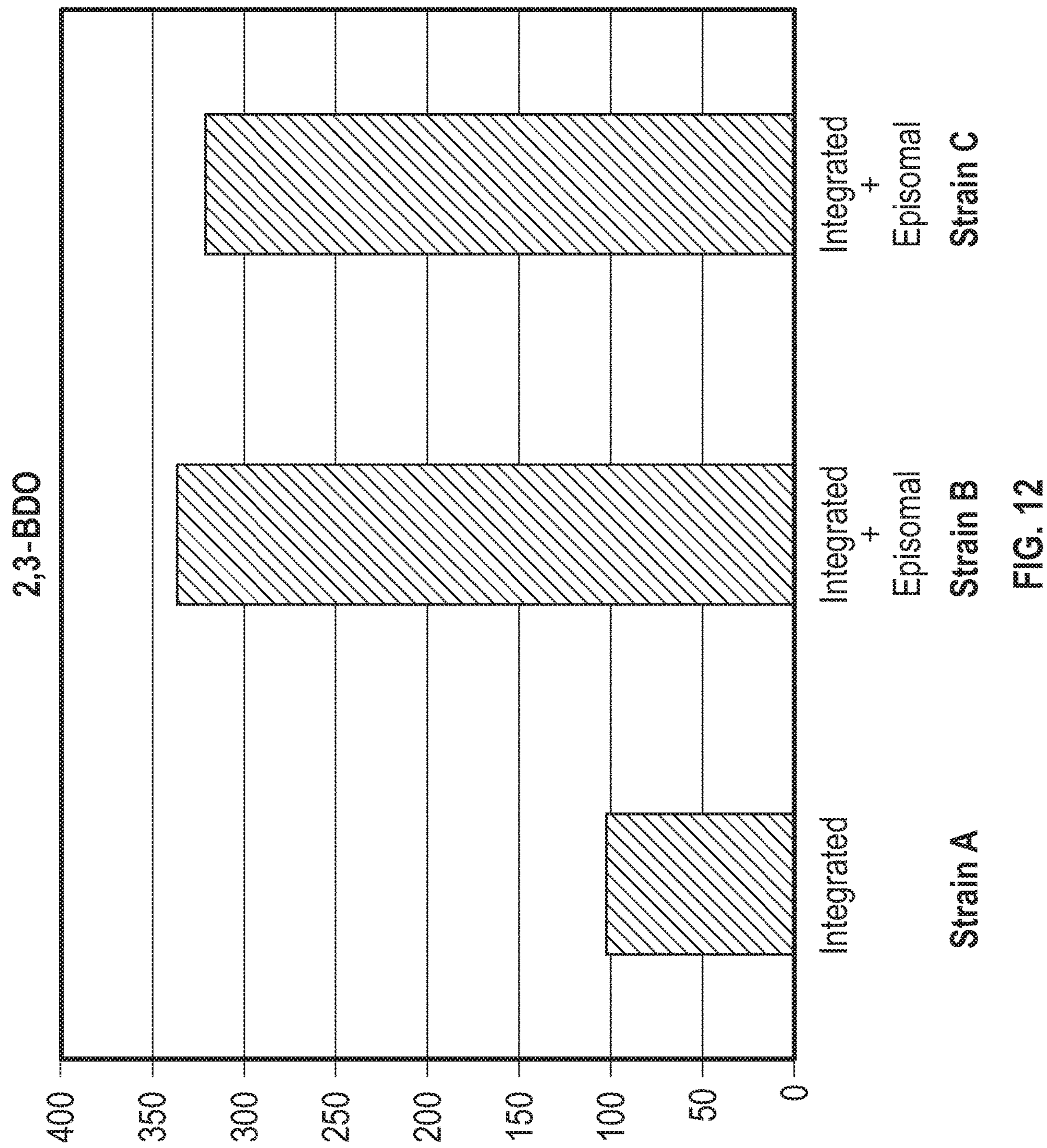
FIG. 12 shows that methanotroph strains that contained additional copies of 2,3-BDO pathway enzymes (Strains B and C) within an episomal vector produced over 3 times as much 2,3-BDO compared to the singly integrated strain (Strain A) in shake bottle experiments. Strain B and Strain C were precultured in 10 μM lanthanum in the presence of Kanamycin at 37° C. for 48 hours. Strain A was precultured in the same conditions except that no Kanamycin was added. After 48 hours, the lanthanum was diluted by 50 fold (50×) and 2,3-BDO titers were measured after 96 hours.

A methanotroph strain that contained additional copies of 2,3-BDO pathway enzymes (Strains B and C) within an episomal vector produced increased 2,3-BDO compared to the singly integrated strain (Strain A) in shake bottle experiments. Strain B and Strain C were precultured in 10 μM lanthanum in the presence of Kanamycin at 37° C. for 48 hours. Strain A was precultured in the same conditions except that no Kanamycin was added. After 48 hours, the lanthanum was diluted by 50 fold (50×) and 2,3-BDO titer were measured after 96 hours. As seen in FIG. 12, the strains that contained additional copies of 2,3-BDO pathway enzymes (Strains B and C) within an episomal vector produced over 3 times as much 2,3-BDO compared to the singly integrated strain (Strain A).

Example 7: Preculturing

The effect of preculturing was tested in both episomal and integration strains as well as strains having both episomally expressed 2,3-BDO pathway genes and integrated copies of the genes.

Figure 13:
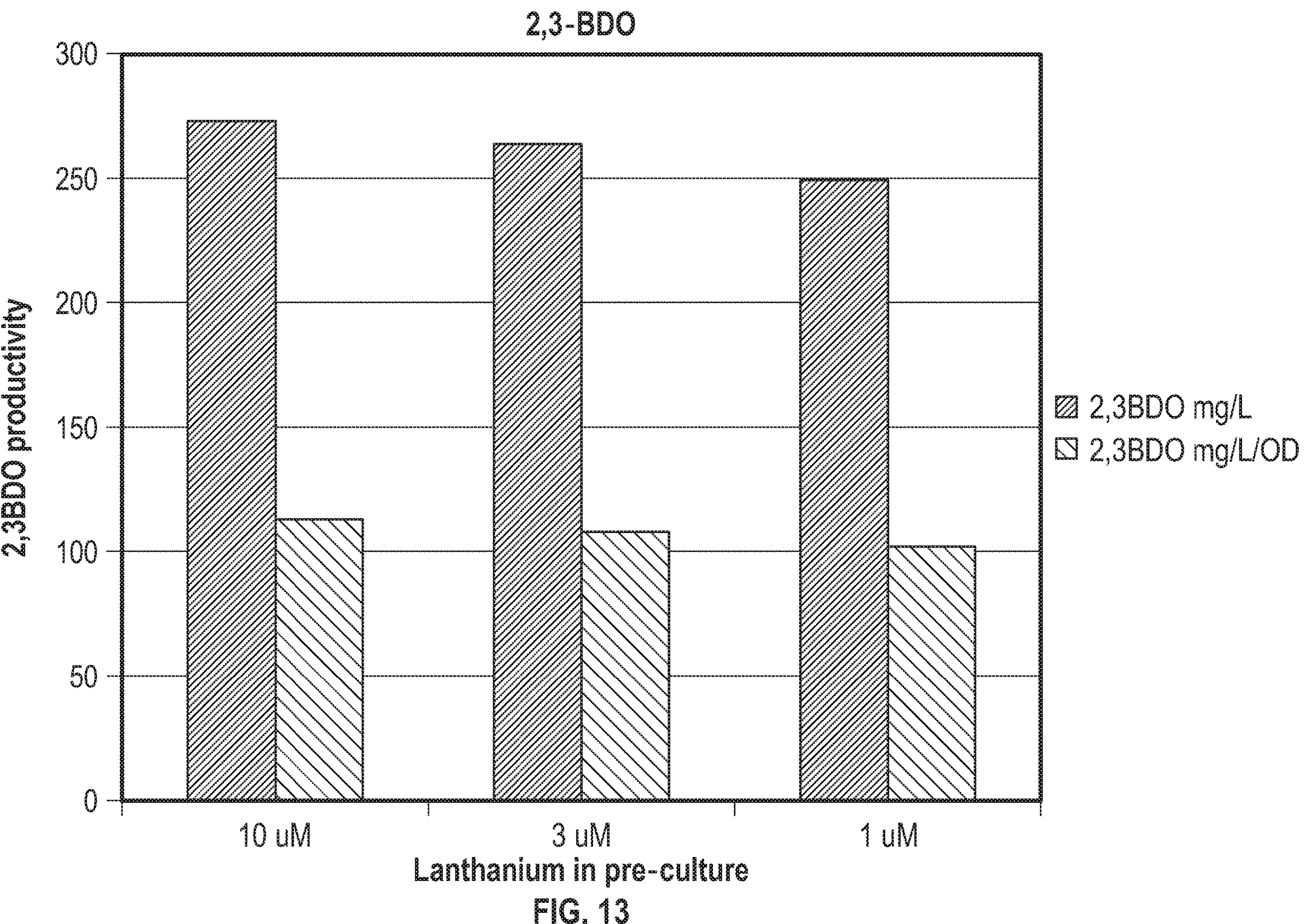
FIG. 13 shows the effect (in a shake bottle experiment) of preculturing a methanotroph strain having genes encoding for 2,3-BDO pathway enzymes when those genes are episomally expressed (Strain D). This methanotroph strain was precultured in 10 uM, 3 uM, and 1 uM lanthanum. The production media was subsequently diluted by 50-fold. Higher lanthanum concentrations resulted in higher 2,3BDO titers for episomally expressed methanotroph strains.

As seen in FIG. 13, the effect of preculturing a methanotroph strain (in a shake bottle) in which the genes encoding for 2,3-BDO pathway enzymes were episomally expressed (Strain D). The methanotroph strain was precultured in 10 uM, 3 uM, and 1 uM lanthanum during pre-culture. The production media was later diluted by 50-fold. Higher lanthanum concentrations resulted in higher 2,3BDO titers for episomally expressed strains.

Figure 14:
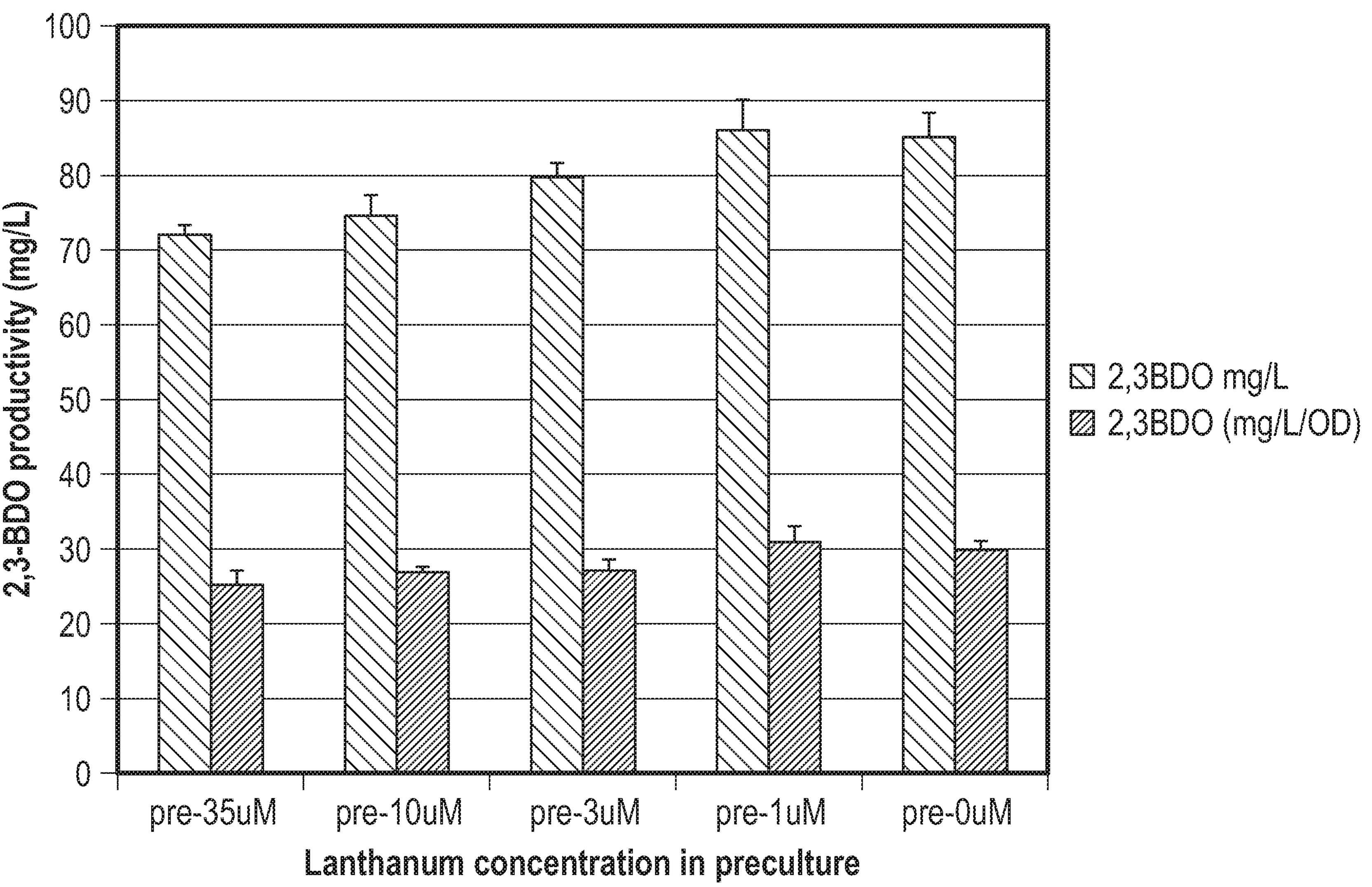
FIG. 14 shows the effect (in a shake bottle experiment) of preculturing a methanotroph strain having genes encoding for 2,3-BDO pathway enzymes when those genes are integrated into the methanotroph's genome (Strain A). This strain was precultured in 35 μM, 10 μM, 3 μM, 1 μM, and 0 μM lanthanum. The production media was subsequently diluted by 50 fold (50×). Levels of 2,3-BDO production increased when the strain was precultured with lower concentration of lanthanum.

As seen in FIG. 14, the effect of preculturing a methanotroph strain (in a shake bottle) in which the genes encoding for 2,3-BDO pathway enzymes are integrated into the methanotroph's genome. The methanotroph strain (Strain A) was precultured in 35 μM, 10 μM, 3 μM, 1 μM, and 0 μM lanthanum. The production media was later diluted by 50 fold (50×). Levels of 2,3-BDO production increased when the strain are precultured with lower concentration of lanthanum.

Figure 15:
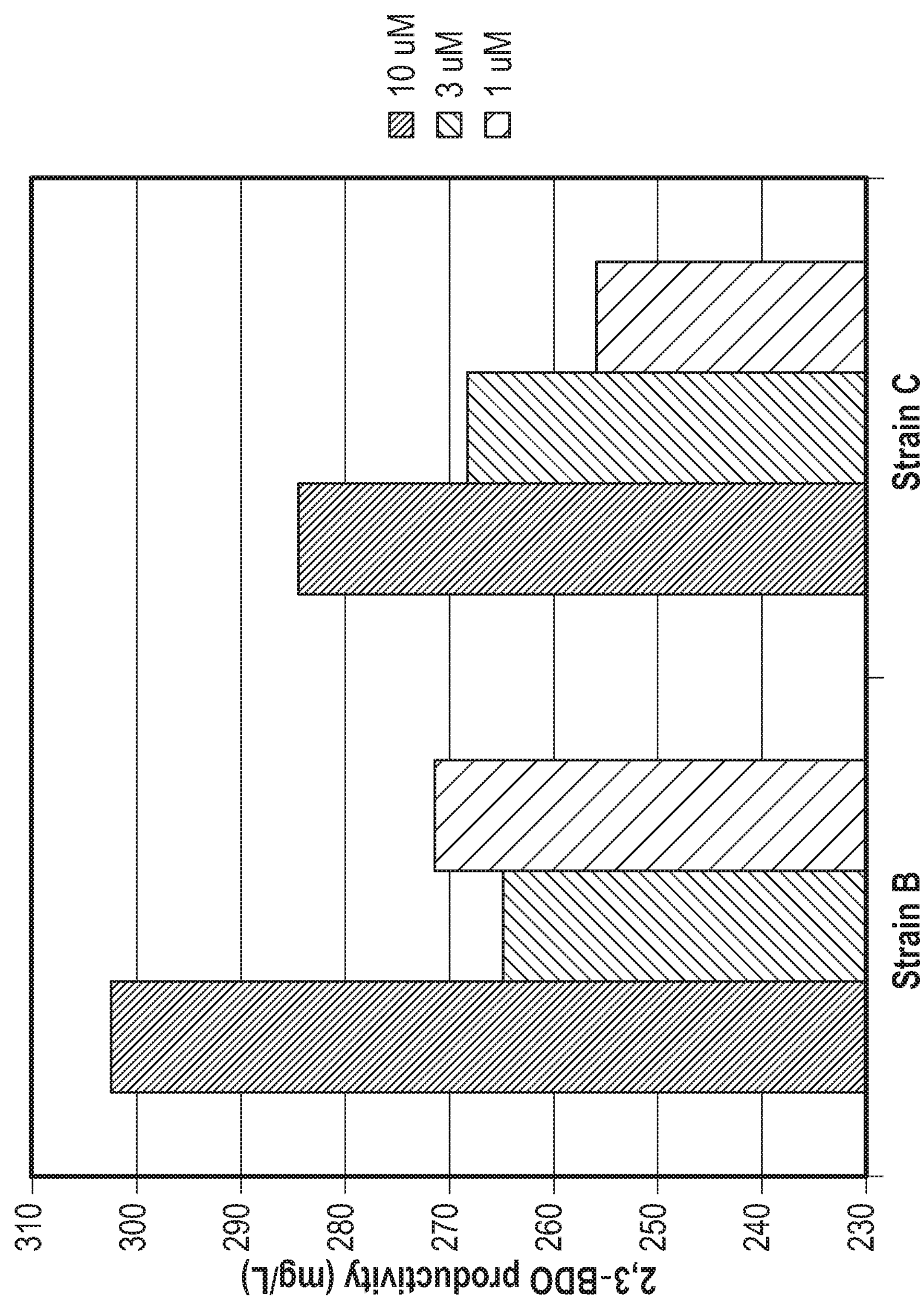
FIG. 15 shows the effect of preculturing at different lanthanum concentrations (10 μM, 3 μM, and 1 μM) of the two strains from FIG. 12 (Strains B and C) in a shake bottle experiment. Both strains contained both an integrated and an episomally expressed copy of the 2,3-BDO pathway enzymes. Generally, the strains having episomally expressed 2,3-BDO pathway enzymes, yield higher 2,3-BDO titers when precultured in 10 μM lanthanum.

As seen in FIG. 15, the shows the effect of preculturing at different lanthanum concentrations (10 μM, 3 μM, and 1 μM) of the two strains from FIG. 12 (Strains B and C) in a shake bottle experiment. Both strains contain one integrated copy and episomally expressed copies of the 2,3-BDO pathway enzymes. Generally, the strains having episomally expressed 2,3-BDO pathway enzymes, yield higher 2,3-BDO titers when precultured in 10 μM lanthanum.

What is claimed is:

1. A vector comprising two or more genes encoding: (a) an acetoin reductase comprising an amino acid sequence that is at least 90% identical to SEQ ID NO: 9; (b) an alpha-acetolactate decarboxylase comprising an amino acid sequence that is at least 90% identical to SEQ ID NO: 7; and/or (c) an acetolactate synthase comprising an amino acid sequence that is at least 90% identical to any one of SEQ ID NO: 1, 3, and 19.

2. The vector of claim 1, wherein:

(a) the acetoin reductase comprises the amino acid sequence of SEQ ID NO: 9 or a conservatively-substituted variant thereof;

(b) the alpha-acetolactate decarboxylase comprises the amino acid sequence of SEQ ID NO: 7 or a conservatively-substituted variant thereof; and/or (c) the acetolactate synthase comprises an amino acid sequence of any one of SEQ ID NOs: 1, 3, and 19 or a conservatively-substituted variant thereof.

3. The vector of claim 1, wherein:

(a) the acetoin reductase comprises the amino acid sequence of SEQ ID NO: 9;

(b) the alpha-acetolactate decarboxylase comprises the amino acid sequence of SEQ ID NO: 7; and/or (c) the acetolactate synthase comprises an amino acid sequence of any one of SEQ ID NOs: 1, 3, and 19.

4. The vector of claim 1, wherein the gene encoding the acetolactate synthase is 5' in relation to any other gene on the vector.

5. The vector of claim 1, wherein the gene encoding the acetoin reductase is 3' in relation to any other gene on the vector.

6. The vector of claim 1, wherein the gene encoding the alpha-acetolactate decarboxylase is neither 5' or 3' in relation to any other gene on the vector.

7. The vector of claim 1, comprising a gene encoding an acetoin reductase.

8. The vector of claim 7, wherein the acetoin reductase comprises an amino acid sequence that is at least 95% identical to SEQ ID NO: 9.

9. The vector of claim 1, comprising a gene encoding an alpha-acetolactate decarboxylase.

10. The vector of claim 9, wherein the alpha-acetolactate decarboxylase comprises an amino acid sequence that is at least 95% identical to SEQ ID NO: 7.

11. The vector of claim 1, comprising a gene encoding an acetolactate synthase.

12. The vector of claim 11, wherein the acetolactate synthase comprises an amino acid sequence that is at least 95% identical to any one of SEQ ID NOs: 1, 3, and 19.

13. The vector of claim 1, further comprising a promoter that is active within a methanotroph.

14. The vector of claim 1, wherein the vector is an integration vector.

15. The vector of claim 1, wherein the vector is an episomal vector.

* * * * *

```
                                SEQUENCE LISTING


<160> NUMBER OF SEQ ID NOS: 20

<210> SEQ ID NO 1
<211> LENGTH: 571
<212> TYPE: PRT
<213> ORGANISM: Bacillus subtilis

<400> SEQUENCE: 1

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
```

```
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570


<210> SEQ ID NO 2
<211> LENGTH: 1713
<212> TYPE: DNA
<213> ORGANISM: Bacillus subtilis

<400> SEQUENCE: 2

atgaccaagg ccaccaagga acagaaaagc ctggtcaaga accgcggtgc tgaactggtt      60

gtggactgcc tcgtggaaca gggcgtgacc catgtcttcg gcatcccggg cgccaagatc     120

gacgccgtct tcgacgccct gcaggataaa ggtccggaaa tcatcgtggc acgccatgag     180

cagaacgcag ccttcatggc ccaggccgtc ggtcggctga cgggtaagcc cggcgtggtg     240

ctggtcacct ccggtccggg agcctcgaac ctggccacgg gactgctcac cgccaacacc     300

gaaggcgacc cggtggtcgc cctggccggt aatgtcatcc gggcggatcg cctgaagcgc     360

acccatcagt ccctggataa cgcggccctg ttccagccaa tcaccaaata tagtgtcgaa     420

gtgcaggatg tgaagaacat cccggaagcc gtcaccaatg cgttccgaat cgcgtccgcc     480

ggccaagcag gggcagcatt cgtgagcttc ccccaggacg tggtcaatga agtgaccaac     540

accaaaaacg tcagagccgt agccgccccg aagctgggcc ctgcagcaga tgacgccatc     600

tccgctgcca tcgcgaagat ccagaccgca aagctgccgg tcgtgctggt cggaatgaag     660

ggcggacgcc cggaggccat caaggccgtg cgtaaactgc tgaagaaggt gcagctaccg     720
```

```
ttcgtggaaa cctaccaggc cgccggcacc ctgagtcggg acttggaaga ccagtatttc    780
ggccgtatcg gcctgttccg caaccagccg ggcgacctgc tcctggaaca agccgatgtg    840
gtgctgacca tcggctacga cccgatcgaa tatgacccga agttctggaa catcaatggc    900
gaccgcacga tcatccatct ggacgaaatc atcgccgaca tcgaccatgc ctatcagccg    960
gacctggaac tgatcggcga catcccgagc accatcaacc acatcgaaca cgatgccgtg   1020
aaggtggaat ttgccgaacg cgaacagaag atcctgtcgg acctgaagca gtatatgcat   1080
gagggcgaac aggtgcctgc cgactggaag tcggacagag cccatccgct ggaaatcgtg   1140
aaggaactgc gtaacgccgt cgacgaccat gtcaccgtca cctgcgatat cggcagccat   1200
gccatttgga tgagccgcta cttccggagc tatgaaccgc tgaccctgat gatctccaac   1260
ggtatgcaga ccctcggcgt cgccctcccg tgggccatcg gcgcaagtct ggtgaagccg   1320
ggcgaaaaag tggtcagcgt gtccggcgac ggcggcttcc tgttctccgc tatggaactg   1380
gaaaccgcgg tccgcctgaa ggccccgatc gtgcatatcg tgtggaacga cagcacctac   1440
gacatggtcg ccttccagca gctgaaaaag tacaaccgca ccagcgccgt ggacttcggc   1500
aatatcgaca tcgtgaagta tgccgaatcc ttcggagcca ccggactgcg cgtggaatcc   1560
ccggaccagc tggcggacgt tctgcgtcag ggcatgaatg ccgaaggtcc cgtgattatc   1620
gatgtgcccg tcgactacag cgacaacatc aacctggcct cggacaaatt gccgaaggag   1680
ttcggcgaac tgatgaaaac aaaagcacta taa                                1713
```

<210> SEQ ID NO 3
<211> LENGTH: 556
<212> TYPE: PRT
<213> ORGANISM: Clostridium sp.

<400> SEQUENCE: 3

```
Met Asn Arg Asp Ile Lys Lys Glu Val Gln Leu Asn Thr Ala Gln Met
1               5                   10                  15

Leu Val Lys Cys Leu Glu Ala Glu Gly Val Lys Tyr Ile Phe Gly Ile
            20                  25                  30

Pro Gly Glu Glu Asn Leu Glu Ile Met Asn Ala Ile Ser Asp Ser Thr
        35                  40                  45

Ile Glu Phe Ile Thr Thr Arg His Glu Gln Gly Ala Ala Phe Met Ala
    50                  55                  60

Asp Val Tyr Gly Arg Leu Thr Gly Lys Ala Gly Val Cys Leu Ser Thr
65                  70                  75                  80

Leu Gly Pro Gly Ala Thr Asn Leu Val Thr Gly Val Ala Asp Ala Asp
                85                  90                  95

Ser Asp Gly Ala Pro Val Val Ala Ile Thr Gly Gln Val Gly Thr Glu
            100                 105                 110

Arg Met His Ile Thr Ser His Gln Phe Leu Asp Leu Cys Lys Met Phe
        115                 120                 125

Glu Pro Ile Thr Lys Arg Ser Lys Gln Ile Val Arg Pro Asp Thr Val
    130                 135                 140

Ser Glu Ile Ile Arg Leu Val Phe Lys Tyr Ala Glu Ser Glu Lys Pro
145                 150                 155                 160

Gly Ala Cys His Ile Asp Leu Pro Val Asn Ile Ala Lys Met Pro Val
                165                 170                 175

Gly Ala Leu Glu Lys Pro Leu Glu Lys Lys Ile Pro Pro Lys Glu His
            180                 185                 190

Ala Asp Leu Ser Thr Ile Glu Glu Ala Ala Ser Glu Ile Phe Lys Ala
```

```
        195                 200                 205

Lys Asn Pro Ile Ile Leu Ala Gly Ser Gly Ala Ile Arg Gly Asn Ser
    210                 215                 220

Ser Lys Ala Val Thr Glu Phe Ala Thr Lys Leu Lys Ile Pro Val Ile
225                 230                 235                 240

Asn Thr Met Met Ala Lys Gly Ile Ile Pro Met Asp Asn Lys Tyr Ser
                245                 250                 255

Met Trp Thr Ile Gly Ile Pro Gln Lys Asp Tyr Val Asn Lys Ile Ile
            260                 265                 270

Glu Glu Ala Asp Leu Val Ile Thr Ile Gly Tyr Asp Ile Val Glu Tyr
        275                 280                 285

Ala Pro Ser Lys Trp Asn Ile Asn Gly Asp Ile Lys Ile Val His Ile
    290                 295                 300

Asp Ala Arg Pro Ser His Ile Asn Lys Leu Tyr Gln Pro Ile Val Glu
305                 310                 315                 320

Val Val Gly Asp Ile Ser Asp Ala Leu Tyr Asn Ile Leu Arg Arg Thr
                325                 330                 335

Ser Ser Lys Asp Glu Pro Val Lys Ala Leu Glu Ile Lys Ser Glu Met
            340                 345                 350

Leu Ala Glu His Glu Ser Tyr Ala Asn Asp Asn Ala Phe Pro Met Lys
        355                 360                 365

Pro Gln Arg Ile Leu Asn Asp Val Arg Lys Val Met Gly Pro His Asp
    370                 375                 380

Ile Val Ile Ser Asp Val Gly Ala His Lys Met Trp Ile Ala Arg His
385                 390                 395                 400

Tyr Asn Cys Tyr Glu Pro Asn Thr Cys Ile Ile Ser Asn Gly Phe Ala
                405                 410                 415

Thr Met Gly Ile Gly Val Pro Gly Ala Ile Ala Ala Lys Leu Ile Asn
            420                 425                 430

Pro Asp Lys Lys Val Leu Ala Ile Val Gly Asp Gly Gly Phe Met Met
        435                 440                 445

Asn Asn Gln Glu Leu Glu Thr Ala Leu Arg Ile Lys Thr Pro Ile Val
    450                 455                 460

Val Leu Ile Phe Asn Asp Ser Asn Tyr Gly Leu Ile Lys Trp Lys Gln
465                 470                 475                 480

Glu Glu His Tyr Gly Lys Ser Cys Tyr Val Asp Phe Thr Asn Pro Asp
                485                 490                 495

Phe Val Lys Leu Ala Glu Ser Met Tyr Ala Lys Gly Tyr Arg Val Glu
            500                 505                 510

Lys Ala Glu Asp Leu Ile Pro Thr Leu Glu Glu Ala Phe Lys Gln Asn
        515                 520                 525

Val Pro Ala Val Ile Asp Cys Gln Val Asp Tyr Gly Glu Asn Ile Lys
    530                 535                 540

Leu Thr Lys His Leu Lys Glu Val Tyr Glu Asn Met
545                 550                 555
```

<210> SEQ ID NO 4
<211> LENGTH: 1671
<212> TYPE: DNA
<213> ORGANISM: Clostridium sp.

<400> SEQUENCE: 4

```
atgaatcggg atatcaagaa agaggtgcag ctcaacacgg cccagatgct ggtcaagtgt      60

ctggaagccg agggcgtcaa gtatatcttc ggcatcccgg gcgaggagaa tctcgaaatc     120
```

```
atgaacgcca tctcggattc cacgatcgag ttcatcacca cccgccatga acagggcgcg    180
gccttcatgg ccgacgtgta cggccggctg accggcaagg cgggcgtgtg tctgagcacc    240
ctcggccccg gcgcgaccaa cctggtcacc ggcgtggccg acgccgactc cgacggcgcc    300
cccgtggtcg cgatcaccgg ccaggtgggc acggagcgga tgcacatcac ctcccatcag    360
ttcctcgacc tctgcaagat gttcgagccg atcaccaagc ggagcaagca gatcgtccgc    420
ccggacacgg tgtcggagat catccgcctg gtgttcaagt acgccgaaag cgaaaagccc    480
ggcgcctgtc atatcgacct gccggtcaac atcgccaaga tgcccgtcgg cgccctggag    540
aagccgctgg agaaaaaaat cccgccgaag gaacacgcgg acctgtccac catcgaggaa    600
gcggcgtccg agatcttcaa ggccaaaaac cccatcatcc tggccggcag cggcgccatc    660
cgcggcaaca gcagcaaggc ggtcaccgag ttcgccacca agctgaagat ccccgtcatc    720
aacacgatga tggccaaggg catcatcccg atggacaaca agtatagcat gtggaccatc    780
ggcatccccc agaaggacta tgtgaacaag atcatcgaag aggccgacct ggtcatcacc    840
atcggctacg acatcgtgga atatgccccg tcgaaatgga acatcaacgg cgacatcaag    900
atcgtccata tcgacgcccg cccctcgcac atcaacaaac tctaccagcc catcgtggag    960
gtggtcggcg acatcagcga cgcgctgtat aacatcctgc gccgcaccag ctcgaaagac   1020
gagccggtca aggcgctgga gatcaagtcg gaaatgctgg cggagcacga gtcctacgcg   1080
aacgacaatg cgttcccgat gaagccgcag cgcatcctca acgatgtgcg caaagtcatg   1140
ggcccgcacg acatcgtgat ctccgatgtg ggcgcccata aaatgtggat cgcccgccac   1200
tataactgct acgagccgaa tacctgcatc atctcgaacg gcttcgccac gatgggcatc   1260
ggcgtcccgg gcgcgatcgc cgccaaactc atcaacccgg ataagaaggt cctggccatc   1320
gtcggcgacg gcggcttcat gatgaataac caggaactgg agacggcgct gcgcatcaaa   1380
acgcccatcg tggtcctcat cttcaacgac tccaattacg gcctcatcaa gtggaagcag   1440
gaggagcatt atggcaaatc gtgctatgtg gacttcacca acccggactt cgtgaagctg   1500
gccgagagca tgtacgccaa aggctatcgc gtggagaaag ccgaggatct gatcccgacc   1560
ctcgaagagg ccttcaagca gaatgtcccg gcggtcatcg actgccaggt ggactatggc   1620
gagaatatca agctcaccaa gcacctcaag gaggtctatg aaaacatgtg a             1671
```

```
<210> SEQ ID NO 5
<211> LENGTH: 239
<212> TYPE: PRT
<213> ORGANISM: Clostridium sp.

<400> SEQUENCE: 5

Met Asp Asp Glu Val Lys Val Pro Asn His Ile Tyr Gln Met Ser Thr
1               5                   10                  15

Ile Asn Ala Leu Val Ser Gly Leu Tyr Asp Gly Cys Val Ser Leu Ser
            20                  25                  30

Lys Leu Leu Lys Lys Gly Asn Phe Gly Ile Gly Thr Phe Lys Gly Leu
        35                  40                  45

Asp Gly Glu Leu Thr Leu Leu Asn Gly Thr Phe Tyr Arg Thr Lys Pro
    50                  55                  60

Asp Gly Ser Val Tyr Val Cys Ser Lys Asn Val Ser Val Pro Phe Ala
65                  70                  75                  80

Val Val Thr Glu Leu Glu Asn Tyr Asn Thr Tyr Asn Ile Gln Asn Arg
                85                  90                  95
```

```
Thr Ser Tyr Glu Asp Ile Arg Lys Glu Leu Asp Ser Phe Ile Glu Ser
            100                 105                 110

Lys Asn Ile Phe Tyr Ala Phe Tyr Met Glu Gly Lys Phe Asn Tyr Val
        115                 120                 125

Lys Thr Arg Thr Val Val Lys Gln Asn Met Pro Tyr Lys Pro Met Ala
    130                 135                 140

Glu Val Val Lys Asp Gln Pro Met Phe Glu Tyr Asn Gly Val Asp Gly
145                 150                 155                 160

Tyr Val Val Gly Phe Arg Cys Pro Asp Tyr Val Glu Gly Leu Asn Val
                165                 170                 175

Pro Gly Tyr His Phe His Phe Ile Asn Lys Asp Lys Lys Phe Gly Gly
            180                 185                 190

His Ile Ser Glu Phe Ser Ile Glu Asn Ala Lys Val Tyr Val Gln Asn
        195                 200                 205

Cys Ser Cys Phe Arg Met Glu Leu Pro Lys Asn Glu Ser Phe Tyr Asn
    210                 215                 220

Met Glu Val Gln Asp Arg Asn Asp Glu Ile Thr Ser Val Glu Lys
225                 230                 235


<210> SEQ ID NO 6
<211> LENGTH: 720
<212> TYPE: DNA
<213> ORGANISM: Clostridium sp.

<400> SEQUENCE: 6

atggatgatg aggtgaaagt cccgaaccac atctaccaga tgtcgaccat caatgccctg      60

gtcagcggcc tctacgacgg ctgtgtgtcg ctctcgaagc tcctgaaaaa gggcaatttc     120

ggcatcggca cgttcaaggg cctggatggc gagctgaccc tcctgaacgg cacgttctat     180

cgcaccaaac cggatggctc cgtgtacgtg tgcagcaaga acgtgagcgt ccccttcgcg     240

gtcgtcaccg agctggagaa ctacaatacc tataacatcc agaatcgcac ctcctatgag     300

gacatccgca aggagctgga ctcgttcatc gagtcgaaga acatcttcta tgccttctat     360

atggaaggca aattcaacta cgtcaaaacc cgcaccgtcg tgaagcagaa catgccgtac     420

aagccgatgg ccgaggtggt caaagaccag ccgatgttcg aatacaacgg cgtcgatggc     480

tacgtcgtcg gcttccggtg cccggattat gtggaaggcc tcaatgtgcc cggctaccat     540

ttccacttca tcaacaagga caaaaagttc ggcggccaca tctccgagtt ctcgatcgag     600

aacgccaaag tctacgtcca gaactgctcc tgtttccgca tggagctccc gaagaatgag     660

agcttctaca acatggaggt ccaggaccgc aacgacgaaa tcacgtccgt ggagaaatga     720


<210> SEQ ID NO 7
<211> LENGTH: 259
<212> TYPE: PRT
<213> ORGANISM: Klebsiella pneumoniae

<400> SEQUENCE: 7

Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60
```

```
Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser
```

```
<210> SEQ ID NO 8
<211> LENGTH: 780
<212> TYPE: DNA
<213> ORGANISM: Klebsiella pneumoniae

<400> SEQUENCE: 8

atgaaccact cggccgaatg cacctgcgaa gagagcctct gcgaaaccct ccgggccttc     60

tcggcccagc acccggagag cgtcctgtac cagacgagcc tgatgtcggc gctgctgtcg    120

ggcgtgtatg aaggctcgac gaccatcgcc gacctgctga agcatggcga cttcggcctg    180

ggcaccttca atgaactgga cggcgagctc atcgccttca gctcgcaggt gtatcagctc    240

cgggccgatg gctccgcccg gaaggcccag cccgaacaga agaccccgtt cgccgtgatg    300

acctggttcc agccgcagta tcggaagacc ttcgaccacc ccgtgagccg ccagcagctc    360

cacgaggtga tcgaccagca gatcccgagc gacaacctct tctgcgccct gcgcatcgac    420

ggccatttcc gccacgcgca tacccgcacc gtcccgcggc agaccccgcc ctaccgcgcc    480

atgaccgatg tcctggatga ccagccggtc ttccggttca accagcgcga gggcgtcctg    540

gtcggcttcc gcaccccgca gcacatgcag ggcatcaacg tcgcgggcta tcatgaacac    600

ttcatcaccg atgatcgcaa gggcggcggc cacctcctcg actaccagct ggaccacggc    660

gtcctgacct tcggcgaaat ccataagctg atgatcgacc tccccgccga cagcgccttc    720

ctgcaggcga atctgcatcc ggacaacctc gatgccgcca tccgctccgt cgagtcgtga    780
```

```
<210> SEQ ID NO 9
<211> LENGTH: 357
<212> TYPE: PRT
<213> ORGANISM: Clostridium sp.

<400> SEQUENCE: 9
```

```
Met Lys Ala Val Leu Trp Tyr Asp Lys Lys Asp Val Arg Val Glu Glu
1               5                   10                  15

Ile Glu Glu Pro Lys Val Lys Glu Asn Ala Val Lys Ile Lys Val Lys
            20                  25                  30

Trp Cys Gly Ile Cys Gly Ser Asp Leu His Glu Tyr Leu Gly Gly Pro
        35                  40                  45

Ile Phe Ile Pro Val Gly Thr Pro His Pro Leu Ser Lys Ser Thr Ala
    50                  55                  60

Pro Val Val Leu Gly His Glu Phe Ser Gly Glu Val Val Glu Ile Gly
65                  70                  75                  80

Ser Lys Val Thr Lys Phe Lys Ala Gly Asp Arg Val Ile Val Glu Pro
                85                  90                  95

Ile Val Ala Cys Gly Lys Cys Pro Ala Cys Leu Glu Gly Lys Tyr Asn
            100                 105                 110

Leu Cys Glu Ala Leu Gly Phe His Gly Leu Cys Gly Ser Gly Gly Gly
        115                 120                 125

Phe Ala Glu Tyr Thr Val Phe Pro Glu Asp Phe Val His Lys Ile Pro
    130                 135                 140

Asp Thr Met Asp Tyr Glu Gln Ala Ala Leu Val Glu Pro Met Ala Val
145                 150                 155                 160

Ala Leu His Ser Leu Arg Val Gly Asn Phe Thr Thr Gly Asn Thr Ala
                165                 170                 175

Leu Val Leu Gly Ala Gly Pro Ile Gly Leu Ala Thr Ile Gln Cys Leu
            180                 185                 190

Lys Ala Ser Gly Ala Arg Ile Val Ile Val Phe Gln Arg Lys Ser Val
        195                 200                 205

Arg Gln Glu Tyr Ala Lys Lys Phe Gly Ala Asp Val Val Leu Asp Pro
    210                 215                 220

Asn Glu Val Asp Val Ile Glu Glu Ile Lys Lys Leu Thr Gly Gly Val
225                 230                 235                 240

Gly Val Asp Thr Ser Phe Glu Thr Thr Gly Ala Asn Val Gly Ile Asn
                245                 250                 255

Thr Ala Ile Gln Ala Leu Lys Tyr Glu Gly Thr Ala Val Ile Thr Ser
            260                 265                 270

Val Trp Glu Lys Asn Ala Glu Ile Asn Pro Asn Asp Leu Val Phe Thr
        275                 280                 285

Glu Lys Lys Val Val Gly Thr Leu Ala Tyr Arg His Glu Phe Pro Ser
    290                 295                 300

Thr Ile Ala Leu Met Asn Asp Gly Arg Ile Lys Thr Asp Gly Tyr Ile
305                 310                 315                 320

Thr Lys Arg Ile Ala Leu Glu Asp Ile Val Lys Glu Gly Phe Glu Thr
                325                 330                 335

Leu Thr Gly Pro Glu Lys Lys Lys His Val Lys Ile Ile Val Thr Pro
            340                 345                 350

Asp Lys Ser Leu Leu
        355


<210> SEQ ID NO 10
<211> LENGTH: 1074
<212> TYPE: DNA
<213> ORGANISM: Clostridium sp.

<400> SEQUENCE: 10

atgaaggccg tcctgtggta cgacaaaaag gatgtccgcg tggaagaaat cgaggaaccg     60
```

```
aaggtgaaag aaaacgccgt gaagatcaaa gtcaagtggt gcggcatctg cggctcggac    120

ctgcatgagt atctcggcgg cccgatcttc atcccggtcg gcacccccca cccgctgtcg    180

aagagcaccg cgcccgtcgt gctgggccac gagttctcgg gcgaagtggt ggagatcggc    240

agcaaagtga ccaagttcaa ggcgggcgac cgcgtcatcg tggaaccgat cgtcgcctgc    300

ggcaaatgcc cggcctgcct ggaaggcaag tacaatctgt gcgaggcgct gggcttccac    360

ggcctgtgcg gcagcggcgg cggcttcgcc gagtacacgg tgttcccgga agatttcgtg    420

cacaagatcc ccgacacgat ggattatgaa caggccgcgc tggtggagcc gatggcggtc    480

gcgctgcact ccctgcgggt gggcaacttc accacgggca acaccgccct ggtcctgggc    540

gcgggcccga tcggcctggc caccatccag tgcctcaaag cgtcgggcgc ccggatcgtc    600

atcgtcttcc agcgcaaatc ggtgcggcag gaatacgcca agaagttcgg cgcggacgtg    660

gtcctcgacc cgaatgaggt ggacgtgatc gaggaaatca aaaagctgac cggcggcgtg    720

ggcgtggaca cgagcttcga aaccaccggc gccaacgtcg gcatcaacac cgcgatccag    780

gcgctgaaat atgagggcac cgccgtcatc acctccgtct gggagaagaa cgccgagatc    840

aatccgaacg acctggtctt caccgaaaag aaggtcgtcg gcaccctcgc gtaccggcac    900

gagttcccgt cgaccatcgc cctgatgaac gacggccgca tcaagaccga tggctatatc    960

accaagcgga tcgccctgga agacatcgtc aaggagggct tcgaaaccct gaccggcccg   1020

gagaagaaaa agcacgtcaa aatcatcgtc acgcccgata aaagcctcct gtga         1074


<210> SEQ ID NO 11
<211> LENGTH: 350
<212> TYPE: PRT
<213> ORGANISM: Bacillus subtilis

<400> SEQUENCE: 11

Met Lys Ala Leu Leu Trp His Asn Gln Arg Asp Val Arg Val Glu Glu
1               5                   10                  15

Val Pro Glu Pro Ala Val Arg Ser Gly Ala Val Lys Ile Lys Val Lys
            20                  25                  30

Trp Cys Gly Ile Cys Gly Thr Asp Leu His Glu Tyr Leu Ala Gly Pro
        35                  40                  45

Ile Phe Ile Pro Thr Glu Glu His Pro Leu Thr His Val Lys Ala Pro
    50                  55                  60

Val Ile Leu Gly His Glu Phe Ser Gly Glu Val Val Glu Ile Gly Glu
65                  70                  75                  80

Gly Val Thr Asn His Lys Val Gly Asp Arg Val Val Val Glu Pro Ile
                85                  90                  95

Tyr Ser Cys Gly Lys Cys Glu Ala Cys Lys His Gly His Tyr Asn Val
            100                 105                 110

Cys Glu Gln Leu Val Phe His Gly Leu Gly Gly Asp Gly Gly Gly Phe
        115                 120                 125

Ser Glu Tyr Thr Val Val Pro Ala Asp Met Val His His Ile Pro Asp
    130                 135                 140

Glu Met Thr Tyr Glu Gln Gly Ala Leu Val Glu Pro Ala Ala Val Ala
145                 150                 155                 160

Val His Ala Val Arg Gln Ser Lys Leu Lys Glu Gly Glu Ala Val Ala
                165                 170                 175

Val Phe Gly Cys Gly Pro Ile Gly Leu Leu Val Ile Gln Ala Ala Lys
            180                 185                 190
```

```
Ala Ala Gly Ala Thr Pro Val Ile Ala Val Glu Leu Ser Lys Glu Arg
        195                 200                 205

Gln Glu Leu Ala Lys Leu Ala Gly Ala Asp Tyr Val Leu Asn Pro Ala
    210                 215                 220

Glu Gln Asp Val Val Ala Glu Ile Arg Asn Leu Thr Asn Gly Leu Gly
225                 230                 235                 240

Val Asn Val Ser Phe Glu Val Thr Gly Val Glu Val Val Leu Arg Gln
                245                 250                 255

Ala Ile Glu Ser Thr Ser Phe Glu Gly Gln Thr Val Ile Val Ser Val
            260                 265                 270

Trp Glu Lys Asp Ala Thr Ile Thr Pro Asn Asn Leu Val Leu Lys Glu
        275                 280                 285

Lys Glu Val Val Gly Ile Leu Gly Tyr Arg His Ile Phe Pro Ser Val
    290                 295                 300

Ile Lys Leu Ile Ser Ser Gly Gln Ile Gln Ala Glu Lys Leu Ile Thr
305                 310                 315                 320

Lys Lys Ile Thr Val Asp Gln Val Val Glu Glu Gly Phe Glu Ala Leu
                325                 330                 335

Val Lys Asp Lys Lys Gln Val Lys Ile Leu Val Ser Pro Lys
            340                 345                 350
```

<210> SEQ ID NO 12
<211> LENGTH: 1053
<212> TYPE: DNA
<213> ORGANISM: Bacillus subtilis

<400> SEQUENCE: 12

```
atgaaagccc tgctgtggca taaccagcgc gacgtgcggg tggaagaggt cccggagccc     60

gccgtccgca gcggcgcggt gaaaatcaaa gtgaaatggt gcggcatctg tggcaccgac    120

ctgcatgaat atctggccgg ccccatcttc atcccgacgg aggaacatcc gctgacgcac    180

gtcaaggccc cggtcatcct cggccatgag ttcagcggcg aggtggtgga gatcggcgaa    240

ggcgtcacca atcacaaagt cggcgatcgc gtggtcgtcg aaccgatcta ctcgtgcggc    300

aagtgtgagg cgtgcaagca cggccactat aatgtctgcg agcagctggt gttccacggc    360

ctgggcggcg acggcggcgg cttctcggag tacaccgtgg tgccggcgga tatggtccac    420

cacatcccgg atgaaatgac ctacgagcag ggcgccctgg tcgagccggc cgccgtggcg    480

gtgcacgcgg tgcgccagag caaactcaag gagggcgaag ccgtggccgt cttcggctgc    540

ggcccgatcg gcctgctggt catccaggcg gccaaagcgg cgggcgcgac cccgtcatc    600

gcggtcgagc tgtcgaagga acgccaggag ctcgccaagc tggcgggcgc ggattatgtc    660

ctgaaccccg ccgaacagga cgtggtggcg gaaatccgga acctgaccaa cggcctgggc    720

gtcaacgtct ccttcgaggt caccggcgtg gaagtcgtcc tgcggcaggc gatcgaatcg    780

acctcgttcg agggccagac ggtcatcgtg tcggtctggg agaaggacgc caccatcacg    840

cccaataatc tggtcctgaa agagaaggaa gtggtcggca tcctcggcta ccggcatatc    900

ttcccgtccg tcatcaagct gatctcgtcg ggccagatcc aggccgagaa actcatcacc    960

aagaagatca cggtggacca ggtggtcgaa gaaggcttcg aagcgctggt caaggataag   1020

aagcaggtga agatcctcgt gtcgccgaag tga                                1053
```

<210> SEQ ID NO 13
<211> LENGTH: 350
<212> TYPE: PRT
<213> ORGANISM: Paenibacillus polymyxa

<400> SEQUENCE: 13

```
Met Gln Ala Leu Arg Trp His Gly Ile Lys Asp Leu Arg Leu Glu Asn
1               5                   10                  15

Ile Glu Gln Pro Ala Ala Leu Pro Gly Lys Val Lys Ile Lys Val Glu
            20                  25                  30

Trp Cys Gly Ile Cys Gly Ser Asp Leu His Glu Tyr Val Ala Gly Pro
        35                  40                  45

Ile Phe Ile Pro Glu Asn Ala Gln His Pro Leu Thr Gly Glu Lys Ser
    50                  55                  60

Pro Ile Val Met Gly His Glu Phe Ser Gly Gln Phe Phe Asp Phe Gly
65                  70                  75                  80

Glu Gly Val Thr Lys Ile Gln Val Gly Asp Arg Glu Val Val Glu Pro
                85                  90                  95

Val Phe Ala Cys Gly Glu Cys Asp Ala Cys Arg Gln Gly Lys Tyr Asn
            100                 105                 110

Leu Cys Asp Lys Met Gly Phe Leu Gly Leu Ala Gly Gly Gly Gly Gly
        115                 120                 125

Phe Ser Glu Tyr Val Ala Ala Asp Glu His Met Val His Lys Ile Pro
    130                 135                 140

Glu Ser Val Ser Phe Glu Gln Gly Ala Leu Val Glu Pro Ser Ala Val
145                 150                 155                 160

Ala Leu Tyr Ala Val Arg Gln Ile Gln Leu Lys Val Asp Asp Lys Ala
                165                 170                 175

Val Val Phe Gly Ala Gly Pro Ile Gly Leu Leu Val Ile Glu Ala Leu
            180                 185                 190

Asn Ala Ser Gly Ala Ser Glu Ile Tyr Ala Glu Glu Leu Ser Glu Glu
        195                 200                 205

Arg Thr Ala Lys Ala Glu Asp Leu Gly Ala Ile Val Leu Asp Pro Asn
    210                 215                 220

Thr Tyr Asp Val Val Glu Glu Leu His Lys Arg Thr Asn Gly Gly Val
225                 230                 235                 240

Tyr Val Pro Tyr Glu Val Thr Glu Val Pro Pro Val Leu Thr Gln Ala
                245                 250                 255

Ile Glu Ser Ala Lys Ile Ser Gly Glu Ile Met Ile Val Ile Ile Phe
            260                 265                 270

Glu Lys Glu Ala Leu Ile Lys Pro Asn Asn Ile Val Met Asn Glu Arg
        275                 280                 285

Asn Leu Thr Gly Leu Ile Cys Tyr Asp Asp Val Phe Pro Ala Leu Ile
    290                 295                 300

Ser Leu Met Glu Asn Gly Tyr Phe Pro Ala Asp Lys Leu Val Ile Lys
305                 310                 315                 320

Arg Ile Lys Leu Val Asp Val Ile Glu Ala Ala Phe Glu Ser Leu Leu
                325                 330                 335

Ile Glu Glu Tyr Gln Val Thr Ile Leu Val Ser Pro His Ala
            340                 345                 350
```

<210> SEQ ID NO 14
<211> LENGTH: 1053
<212> TYPE: DNA
<213> ORGANISM: Paenibacillus polymyxa

<400> SEQUENCE: 14

```
atgcaggcgc tgcgctggca cggcatcaag gacctgcggc tggagaacat cgagcagccc     60
```

```
gccgccctcc cgggcaaggt gaagatcaag gtggaatggt gcggcatctg cggcagcgac    120
ctgcatgaat atgtcgccgg cccgatcttc atccccgaaa acgcgcagca tccgctcacg    180
ggcgagaagt cgcccatcgt gatgggccat gagttctccg gccagttctt cgacttcggc    240
gaaggcgtga cgaaaatcca ggtgggcgac cgcgaagtgg tggagccggt cttcgcgtgt    300
ggcgaatgcg atgcgtgccg gcagggcaaa tataacctgt gcgataagat gggcttcctg    360
ggcctggccg gcggcggcgg cggcttctcg gaatatgtcg ccgcggatga gcatatggtg    420
cacaaaatcc ccgagtccgt gtccttcgaa cagggcgccc tggtcgagcc gtccgccgtc    480
gccctctacg cggtccgcca gatccagctg aaggtcgatg acaaggcggt ggtcttcggc    540
gccggcccca tcggcctgct cgtcatcgaa gcgctgaacg ccagcggcgc gagcgaaatc    600
tatgcggaag agctcagcga agagcgcacc gccaaagccg aagacctggg cgccatcgtg    660
ctcgacccca acacgtacga tgtcgtcgag gaactccata agcgcacgaa tggcggcgtc    720
tacgtcccct atgaggtcac ggaagtcccg cccgtgctga cccaggccat cgagtccgcc    780
aagatctccg gcgaaatcat gatcgtcatc atcttcgaaa aggaggccct catcaagccg    840
aacaacatcg tcatgaatga acggaacctg acgggcctga tctgctacga cgatgtgttc    900
ccggccctga tctccctcat ggagaatggc tacttccccg ccgacaagct ggtcatcaaa    960
cggatcaagc tggtggatgt catcgaagcg gccttcgagt cgctcctgat cgaggagtac   1020
caggtgacca tcctcgtgtc gccgcacgcc tga                                1053
```

<210> SEQ ID NO 15
<211> LENGTH: 4672
<212> TYPE: DNA
<213> ORGANISM: Methylococcus capsulatus

<400> SEQUENCE: 15

```
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcctacctg acgcttttta tcgcaactct ctactgtttc tccatacccg tttttttggg    300
ctaacaggag gaattaacca tgaccaaggc caccaaggaa cagaaaagcc tggtcaagaa    360
ccgcggtgct gaactggttg tggactgcct cgtggaacag ggcgtgaccc atgtcttcgg    420
catcccgggc gccaagatcg acgccgtctt cgacgccctg caggataaag gtccggaaat    480
catcgtggca cgccatgagc agaacgcagc cttcatggcc caggccgtcg gtcggctgac    540
gggtaagccc ggcgtggtgc tggtcacctc cggtccggga gcctcgaacc tggccacggg    600
actgctcacc gccaacaccg aaggcgaccc ggtggtcgcc ctggccggta atgtcatccg    660
ggcggatcgc ctgaagcgca cccatcagtc cctggataac gcggccctgt tccagccaat    720
caccaaatat agtgtcgaag tgcaggatgt gaagaacatc ccggaagccg tcaccaatgc    780
gttccgaatc gcgtccgccg gccaagcagg ggcagcattc gtgagcttcc cccaggacgt    840
ggtcaatgaa gtgaccaaca ccaaaaacgt cagagccgta gccgccccga agctgggccc    900
tgcagcagat gacgccatct ccgctgccat cgcgaagatc cagaccgcaa agctgccggt    960
cgtgctggtc ggaatgaagg gcggacgccc ggaggccatc aaggccgtgc gtaaactgct   1020
gaagaaggtg cagctaccgt tcgtggaaac ctaccaggcc gccggcaccc tgagtcggga   1080
cttggaagac cagtatttcg gccgtatcgg cctgttccgc aaccagccgg gcgacctgct   1140
```

```
cctggaacaa gccgatgtgg tgctgaccat cggctacgac ccgatcgaat atgacccgaa   1200
gttctggaac atcaatggcg accgcacgat catccatctg gacgaaatca tcgccgacat   1260
cgaccatgcc tatcagccgg acctggaact gatcggcgac atcccgagca ccatcaacca   1320
catcgaacac gatgccgtga aggtggaatt tgccgaacgc gaacagaaga tcctgtcgga   1380
cctgaagcag tatatgcatg agggcgaaca ggtgcctgcc gactggaagt cggacagagc   1440
ccatccgctg gaaatcgtga aggaactgcg taacgccgtc gacgaccatg tcaccgtcac   1500
ctgcgatatc ggcagccatg ccatttggat gagccgctac ttccggagct atgaaccgct   1560
gaccctgatg atctccaacg gtatgcagac cctcggcgtc gccctcccgt gggccatcgg   1620
cgcaagtctg gtgaagccgg gcgaaaaagt ggtcagcgtg tccggcgacg gcggcttcct   1680
gttctccgct atggaactgg aaaccgcggt ccgcctgaag gccccgatcg tgcatatcgt   1740
gtggaacgac agcacctacg acatggtcgc cttccagcag ctgaaaaagt acaaccgcac   1800
cagcgccgtg gacttcggca atatcgacat cgtgaagtat gccgaatcct tcggagccac   1860
cggactgcgc gtggaatccc cggaccagct ggcggacgtt ctgcgtcagg gcatgaatgc   1920
cgaaggtccc gtgattatcg atgtgcccgt cgactacagc gacaacatca acctggcctc   1980
ggacaaattg ccgaaggagt tcggcgaact gatgaaaaca aaagcactat aaaaaggagg   2040
tacgtatgaa ccactcggcc gaatgcacct gcgaagagag cctctgcgaa accctccggg   2100
ccttctcggc ccagcacccg gagagcgtcc tgtaccagac gagcctgatg tcggcgctgc   2160
tgtcgggcgt gtatgaaggc tcgacgacca tcgccgacct gctgaagcat ggcgacttcg   2220
gcctgggcac cttcaatgaa ctggacggcg agctcatcgc cttcagctcg caggtgtatc   2280
agctccgggc cgatggctcc gcccggaagg cccagcccga acagaagacc ccgttcgccg   2340
tgatgacctg gttccagccg cagtatcgga agaccttcga ccaccccgtg agccgccagc   2400
agctccacga ggtgatcgac cagcagatcc cgagcgacaa cctcttctgc gccctgcgca   2460
tcgacggcca tttccgccac gcgcataccc gcaccgtccc gcggcagacc ccgccctacc   2520
gcgccatgac cgatgtcctg gatgaccagc cggtcttccg gttcaaccag cgcgagggcg   2580
tcctggtcgg cttccgcacc ccgcagcaca tgcagggcat caacgtcgcg ggctatcatg   2640
aacacttcat caccgatgat cgcaagggcg gcggccacct cctcgactac cagctggacc   2700
acggcgtcct gaccttcggc gaaatccata agctgatgat cgacctcccc gccgacagcg   2760
ccttcctgca ggcgaatctg catccggaca acctcgatgc cgccatccgc tccgtcgagt   2820
cgtgatttca gcctgataca gattaaatca gaacgcagaa gcggtctgat aaaacagaat   2880
ttgcctggcg gcagtagcgc ggtggtccca cctgacccca tgccgaactc agaagtgaaa   2940
cgccgtagcg ccgatggtag tgtggggtct ccccatgcga gagtagggaa ctgccaggca   3000
tcaaataaaa cgaaaggctc agtcgaaaga ctgggccttt cgttttatct gttgtttgtc   3060
ggtgaacgct ctcctgagta ggacaaatcc gccgggagcg gatttgaacg ttgcgaagca   3120
acggcccgga gggtggcggg caggacgccc gccataaact gccaggcatc aaattaagca   3180
gaaggccatc ctgacggatg gcctttttgc gtttcgaggt tcaggcgaaa ccgcagactc   3240
aagggcgctt gctcccggga aagatcgtat tagtttgcct cgatcggcgg tccttgtgac   3300
agggagatat tcccgacgga tccggggcat tcgagcggaa ccgcccgccg tgggagtttt   3360
tccagcgagc attcgagagt tttcaaggc ggcttcgagg ggttattccg taacgccgcc   3420
gacatgatct gtcccagaat ctccgccgct gttcgtagag cgccgatgca gggtcggcat   3480
```

```
caatcattct tggaggagac acatgaaggc cgtcctgtgg tacgacaaaa aggatgtccg   3540
cgtggaagaa atcgaggaac cgaaggtgaa agaaaacgcc gtgaagatca aagtcaagtg   3600
gtgcggcatc tgcggctcgg acctgcatga gtatctcggc ggcccgatct tcatcccggt   3660
cggcaccccc cacccgctgt cgaagagcac cgcgcccgtc gtgctgggcc acgagttctc   3720
gggcgaagtg gtggagatcg gcagcaaagt gaccaagttc aaggcgggcg accgcgtcat   3780
cgtggaaccg atcgtcgcct gcggcaaatg cccggcctgc ctggaaggca agtacaatct   3840
gtgcgaggcg ctgggcttcc acggcctgtg cggcagcggc ggcggcttcg ccgagtacac   3900
ggtgttcccg gaagatttcg tgcacaagat ccccgacacg atggattatg aacaggccgc   3960
gctggtggag ccgatggcgg tcgcgctgca ctccctgcgg gtgggcaact tcaccacggg   4020
caacaccgcc ctggtcctgg gcgcgggccc gatcggcctg gccaccatcc agtgcctcaa   4080
agcgtcgggc gcccggatcg tcatcgtctt ccagcgcaaa tcggtgcggc aggaatacgc   4140
caagaagttc ggcgcggacg tggtcctcga cccgaatgag gtggacgtga tcgaggaaat   4200
caaaaagctg accggcggcg tgggcgtgga cacgagcttc gaaaccaccg gcgccaacgt   4260
cggcatcaac accgcgatcc aggcgctgaa atatgagggc accgccgtca tcacctccgt   4320
ctgggagaag aacgccgaga tcaatccgaa cgacctggtc ttcaccgaaa agaaggtcgt   4380
cggcaccctc gcgtaccggc acgagttccc gtcgaccatc gccctgatga acgacggccg   4440
catcaagacc gatggctata tcaccaagcg gatcgccctg gaagacatcg tcaaggaggg   4500
cttcgaaacc ctgaccggcc cggagaagaa aaagcacgtc aaaatcatcg tcacgcccga   4560
taaaagcctc ctgtgagact cctgttgata gatccagtaa tgacctcaga actccatctg   4620
gatttgttca gaacgctcgg ttgccgccgg gcgtttttta ttggtgagaa tc           4672
```

```
<210> SEQ ID NO 16
<211> LENGTH: 4651
<212> TYPE: DNA
<213> ORGANISM: Methylococcus capsulatus

<400> SEQUENCE: 16

aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcctacctg acgcttttta tcgcaactct ctactgtttc tccatacccg tttttttggg    300
ctaacaggag gaattaacca tgaccaaggc caccaaggaa cagaaaagcc tggtcaagaa    360
ccgcggtgct gaactggttg tggactgcct cgtggaacag ggcgtgaccc atgtcttcgg    420
catcccgggc gccaagatcg acgccgtctt cgacgccctg caggataaag gtccggaaat    480
catcgtggca cgccatgagc agaacgcagc cttcatggcc caggccgtcg gtcggctgac    540
gggtaagccc ggcgtggtgc tggtcacctc cggtccggga gcctcgaacc tggccacggg    600
actgctcacc gccaacaccg aaggcgaccc ggtggtcgcc ctggccggta atgtcatccg    660
ggcggatcgc ctgaagcgca cccatcagtc cctggataac gcggccctgt tccagccaat    720
caccaaatat agtgtcgaag tgcaggatgt gaagaacatc ccggaagccg tcaccaatgc    780
gttccgaatc gcgtccgccg gccaagcagg ggcagcattc gtgagcttcc cccaggacgt    840
ggtcaatgaa gtgaccaaca ccaaaaacgt cagagccgta gccgccccga agctgggccc    900
tgcagcagat gacgccatct ccgctgccat cgcgaagatc cagaccgcaa agctgccggt    960
```

```
cgtgctggtc ggaatgaagg gcggacgccc ggaggccatc aaggccgtgc gtaaactgct   1020
gaagaaggtg cagctaccgt tcgtggaaac ctaccaggcc gccggcaccc tgagtcggga   1080
cttggaagac cagtatttcg gccgtatcgg cctgttccgc aaccagccgg gcgacctgct   1140
cctggaacaa gccgatgtgg tgctgaccat cggctacgac ccgatcgaat atgacccgaa   1200
gttctggaac atcaatggcg accgcacgat catccatctg gacgaaatca tcgccgacat   1260
cgaccatgcc tatcagccgg acctggaact gatcggcgac atcccgagca ccatcaacca   1320
catcgaacac gatgccgtga aggtggaatt tgccgaacgc gaacagaaga tcctgtcgga   1380
cctgaagcag tatatgcatg agggcgaaca ggtgcctgcc gactggaagt cggacagagc   1440
ccatccgctg gaaatcgtga aggaactgcg taacgccgtc gacgaccatg tcaccgtcac   1500
ctgcgatatc ggcagccatg ccatttggat gagccgctac ttccggagct atgaaccgct   1560
gaccctgatg atctccaacg gtatgcagac cctcggcgtc gccctcccgt gggccatcgg   1620
cgcaagtctg gtgaagccgg gcgaaaaagt ggtcagcgtg tccggcgacg gcggcttcct   1680
gttctccgct atggaactgg aaaccgcggt ccgcctgaag gccccgatcg tgcatatcgt   1740
gtggaacgac agcacctacg acatggtcgc cttccagcag ctgaaaaagt acaaccgcac   1800
cagcgccgtg gacttcggca atatcgacat cgtgaagtat gccgaatcct tcggagccac   1860
cggactgcgc gtggaatccc cggaccagct ggcggacgtt ctgcgtcagg gcatgaatgc   1920
cgaaggtccc gtgattatcg atgtgcccgt cgactacagc gacaacatca acctggcctc   1980
ggacaaattg ccgaaggagt tcggcgaact gatgaaaaca aaagcactat aaaaaggagg   2040
tacgtatgaa ccactcggcc gaatgcacct gcgaagagag cctctgcgaa accctccggg   2100
ccttctcggc ccagcacccg gagagcgtcc tgtaccagac gagcctgatg tcggcgctgc   2160
tgtcgggcgt gtatgaaggc tcgacgacca tcgccgacct gctgaagcat ggcgacttcg   2220
gcctgggcac cttcaatgaa ctggacggcg agctcatcgc cttcagctcg caggtgtatc   2280
agctccgggc cgatggctcc gcccggaagg cccagcccga acagaagacc ccgttcgccg   2340
tgatgacctg gttccagccg cagtatcgga agaccttcga ccaccccgtg agccgccagc   2400
agctccacga ggtgatcgac cagcagatcc cgagcgacaa cctcttctgc gccctgcgca   2460
tcgacggcca tttccgccac gcgcataccc gcaccgtccc gcggcagacc ccgccctacc   2520
gcgccatgac cgatgtcctg gatgaccagc cggtcttccg gttcaaccag cgcgagggcg   2580
tcctggtcgg cttccgcacc ccgcagcaca tgcagggcat caacgtcgcg ggctatcatg   2640
aacacttcat caccgatgat cgcaagggcg gcggccacct cctcgactac cagctggacc   2700
acggcgtcct gaccttcggc gaaatccata agctgatgat cgacctcccc gccgacagcg   2760
ccttcctgca ggcgaatctg catccggaca acctcgatgc cgccatccgc tccgtcgagt   2820
cgtgatttca gcctgataca gattaaatca gaacgcagaa gcggtctgat aaaacagaat   2880
ttgcctggcg gcagtagcgc ggtggtccca cctgacccca tgccgaactc agaagtgaaa   2940
cgccgtagcg ccgatggtag tgtggggtct ccccatgcga gagtagggaa ctgccaggca   3000
tcaaataaaa cgaaaggctc agtcgaaaga ctgggccttt cgttttatct gttgtttgtc   3060
ggtgaacgct ctcctgagta ggacaaatcc gccgggagcg gatttgaacg ttgcgaagca   3120
acggcccgga gggtggcggg caggacgccc gccataaact gccaggcatc aaattaagca   3180
gaaggccatc ctgacggatg gcctttttgc gtttcgaggt tcaggcgaaa ccgcagactc   3240
aagggcgctt gctcccggga aagatcgtat tagtttgcct cgatcggcgg tccttgtgac   3300
```

```
agggagatat tcccgacgga tccggggcat tcgagcggaa ccgcccgccg tgggagtttt   3360
tccagcgagc attcgagagt tttcaaggc ggcttcgagg ggttattccg taacgccgcc   3420
gacatgatct gtcccagaat ctccgccgct gttcgtagag cgccgatgca gggtcggcat   3480
caatcattct tggaggagac acatgaaagc cctgctgtgg cataaccagc gcgacgtgcg   3540
ggtggaagag gtcccggagc ccgccgtccg cagcggcgcg gtgaaaatca aagtgaaatg   3600
gtgcggcatc tgtggcaccg acctgcatga atatctggcc ggccccatct tcatcccgac   3660
ggaggaacat ccgctgacgc acgtcaaggc cccggtcatc ctcggccatg agttcagcgg   3720
cgaggtggtg gagatcggcg aaggcgtcac caatcacaaa gtcggcgatc gcgtggtcgt   3780
cgaaccgatc tactcgtgcg gcaagtgtga ggcgtgcaag cacggccact ataatgtctg   3840
cgagcagctg gtgttccacg gcctgggcgg cgacggcggc ggcttctcgg agtacaccgt   3900
ggtgccggcg gatatggtcc accacatccc ggatgaaatg acctacgagc agggcgccct   3960
ggtcgagccg gccgccgtgg cggtgcacgc ggtgcgccag agcaaactca aggagggcga   4020
agccgtggcc gtcttcggct gcggcccgat cggcctgctg gtcatccagg cggccaaagc   4080
ggcgggcgcg acccccgtca tcgcggtcga gctgtcgaag gaacgccagg agctcgccaa   4140
gctggcgggc gcggattatg tcctgaaccc cgccgaacag gacgtggtgg cggaaatccg   4200
gaacctgacc aacggcctgg gcgtcaacgt ctccttcgag gtcaccggcg tggaagtcgt   4260
cctgcggcag gcgatcgaat cgacctcgtt cgagggccag acggtcatcg tgtcggtctg   4320
ggagaaggac gccaccatca cgcccaataa tctggtcctg aaagagaagg aagtggtcgg   4380
catcctcggc taccggcata tcttcccgtc cgtcatcaag ctgatctcgt cgggccagat   4440
ccaggccgag aaactcatca ccaagaagat cacggtggac caggtggtcg aagaaggctt   4500
cgaagcgctg gtcaaggata agaagcaggt gaagatcctc gtgtcgccga agtgagactc   4560
ctgttgatag atccagtaat gacctcagaa ctccatctgg atttgttcag aacgctcggt   4620
tgccgccggg cgttttttat tggtgagaat c                                  4651
```

<210> SEQ ID NO 17
<211> LENGTH: 4302
<212> TYPE: DNA
<213> ORGANISM: Methylococcus capsulatus

<400> SEQUENCE: 17

```
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcctacctg acgcttttta tcgcaactct ctactgtttc tccatacccg tttttttggg    300
ctaacaggag gaattaacca tgaccaaggc caccaaggaa cagaaaagcc tggtcaagaa    360
ccgcggtgct gaactggttg tggactgcct cgtggaacag ggcgtgaccc atgtcttcgg    420
catcccgggc gccaagatcg acgccgtctt cgacgccctg caggataaag gtccggaaat    480
catcgtggca cgccatgagc agaacgcagc cttcatggcc caggccgtcg gtcggctgac    540
gggtaagccc ggcgtggtgc tggtcacctc cggtccggga gcctcgaacc tggccacggg    600
actgctcacc gccaacaccg aaggcgaccc ggtggtcgcc ctggccggta atgtcatccg    660
ggcggatcgc ctgaagcgca cccatcagtc cctggataac gcggccctgt tccagccaat    720
caccaaatat agtgtcgaag tgcaggatgt gaagaacatc ccggaagccg tcaccaatgc    780
```

```
gttccgaatc gcgtccgccg gccaagcagg ggcagcattc gtgagcttcc cccaggacgt    840
ggtcaatgaa gtgaccaaca ccaaaaacgt cagagccgta gccgccccga agctgggccc    900
tgcagcagat gacgccatct ccgctgccat cgcgaagatc cagaccgcaa agctgccggt    960
cgtgctggtc ggaatgaagg gcggacgccc ggaggccatc aaggccgtgc gtaaactgct   1020
gaagaaggtg cagctaccgt tcgtggaaac ctaccaggcc gccggcaccc tgagtcggga   1080
cttggaagac cagtatttcg gccgtatcgg cctgttccgc aaccagccgg gcgacctgct   1140
cctggaacaa gccgatgtgg tgctgaccat cggctacgac ccgatcgaat atgacccgaa   1200
gttctggaac atcaatggcg accgcacgat catccatctg gacgaaatca tcgccgacat   1260
cgaccatgcc tatcagccgg acctggaact gatcggcgac atcccgagca ccatcaacca   1320
catcgaacac gatgccgtga aggtggaatt tgccgaacgc gaacagaaga tcctgtcgga   1380
cctgaagcag tatatgcatg agggcgaaca ggtgcctgcc gactggaagt cggacagagc   1440
ccatccgctg gaaatcgtga aggaactgcg taacgccgtc gacgaccatg tcaccgtcac   1500
ctgcgatatc ggcagccatg ccatttggat gagccgctac ttccggagct atgaaccgct   1560
gaccctgatg atctccaacg gtatgcagac cctcggcgtc gccctcccgt gggccatcgg   1620
cgcaagtctg gtgaagccgg gcgaaaaagt ggtcagcgtg tccggcgacg gcggcttcct   1680
gttctccgct atggaactgg aaaccgcggt ccgcctgaag gccccgatcg tgcatatcgt   1740
gtggaacgac agcacctacg acatggtcgc cttccagcag ctgaaaaagt acaaccgcac   1800
cagcgccgtg gacttcggca atatcgacat cgtgaagtat gccgaatcct tcggagccac   1860
cggactgcgc gtggaatccc cggaccagct ggcggacgtt ctgcgtcagg gcatgaatgc   1920
cgaaggtccc gtgattatcg atgtgcccgt cgactacagc gacaacatca acctggcctc   1980
ggacaaattg ccgaaggagt tcggcgaact gatgaaaaca aaagcactat aaaaaggagg   2040
tacgtatgaa ccactcggcc gaatgcacct gcgaagagag cctctgcgaa accctccggg   2100
ccttctcggc ccagcacccg gagagcgtcc tgtaccagac gagcctgatg tcggcgctgc   2160
tgtcgggcgt gtatgaaggc tcgacgacca tcgccgacct gctgaagcat ggcgacttcg   2220
gcctgggcac cttcaatgaa ctggacggcg agctcatcgc cttcagctcg caggtgtatc   2280
agctccgggc cgatggctcc gcccggaagg cccagcccga acagaagacc ccgttcgccg   2340
tgatgacctg gttccagccg cagtatcgga agaccttcga ccaccccgtg agccgccagc   2400
agctccacga ggtgatcgac cagcagatcc cgagcgacaa cctcttctgc gccctgcgca   2460
tcgacggcca tttccgccac gcgcataccc gcaccgtccc gcggcagacc ccgccctacc   2520
gcgccatgac cgatgtcctg gatgaccagc cggtcttccg gttcaaccag cgcgagggcg   2580
tcctggtcgg cttccgcacc ccgcagcaca tgcagggcat caacgtcgcg ggctatcatg   2640
aacacttcat caccgatgat cgcaagggcg gcggccacct cctcgactac cagctggacc   2700
acggcgtcct gaccttcggc gaaatccata agctgatgat cgacctcccc gccgacagcg   2760
ccttcctgca ggcgaatctg catccggaca acctcgatgc cgccatccgc tccgtcgagt   2820
cgtgaaaagg aggtacgtat gaaggccgtc ctgtggtacg acaaaaagga tgtccgcgtg   2880
gaagaaatcg aggaaccgaa ggtgaaagaa aacgccgtga agatcaaagt caagtggtgc   2940
ggcatctgcg gctcggacct gcatgagtat ctcggcggcc cgatcttcat cccggtcggc   3000
accccccacc cgctgtcgaa gagcaccgcg cccgtcgtgc tgggccacga gttctcgggc   3060
gaagtggtgg agatcggcag caaagtgacc aagttcaagg cgggcgaccg cgtcatcgtg   3120
```

```
gaaccgatcg tcgcctgcgg caaatgcccg gcctgcctgg aaggcaagta caatctgtgc   3180
gaggcgctgg gcttccacgg cctgtgcggc agcggcggcg gcttcgccga gtacacggtg   3240
ttcccggaag atttcgtgca caagatcccc gacacgatgg attatgaaca ggccgcgctg   3300
gtggagccga tggcggtcgc gctgcactcc ctgcgggtgg gcaacttcac cacgggcaac   3360
accgccctgg tcctgggcgc gggcccgatc ggcctggcca ccatccagtg cctcaaagcg   3420
tcgggcgccc ggatcgtcat cgtcttccag cgcaaatcgg tgcggcagga atacgccaag   3480
aagttcggcg cggacgtggt cctcgacccg aatgaggtgg acgtgatcga ggaaatcaaa   3540
aagctgaccg gcggcgtggg cgtggacacg agcttcgaaa ccaccggcgc caacgtcggc   3600
atcaacaccg cgatccaggc gctgaaatat gagggcaccg ccgtcatcac ctccgtctgg   3660
gagaagaacg ccgagatcaa tccgaacgac ctggtcttca ccgaaaagaa ggtcgtcggc   3720
accctcgcgt accggcacga gttcccgtcg accatcgccc tgatgaacga cggccgcatc   3780
aagaccgatg gctatatcac caagcggatc gccctggaag acatcgtcaa ggagggcttc   3840
gaaaccctga ccggcccgga gaagaaaaag cacgtcaaaa tcatcgtcac gcccgataaa   3900
agcctcctgt gatttcagcc tgatacagat taaatcagaa cgcagaagcg gtctgataaa   3960
acagaatttg cctggcggca gtagcgcggt ggtcccacct gaccccatgc cgaactcaga   4020
agtgaaacgc cgtagcgccg atggtagtgt ggggtctccc catgcgagag tagggaactg   4080
ccaggcatca aataaaacga aaggctcagt cgaaagactg ggcctttcgt tttatctgtt   4140
gtttgtcggt gaacgctctc ctgagtagga caaatccgcc gggagcggat ttgaacgttg   4200
cgaagcaacg gcccggaggg tggcgggcag gacgcccgcc ataaactgcc aggcatcaaa   4260
ttaagcagaa ggccatcctg acggatggcc tttttgcgtt tc                       4302
```

<210> SEQ ID NO 18
<211> LENGTH: 4281
<212> TYPE: DNA
<213> ORGANISM: Methylococcus capsulatus

<400> SEQUENCE: 18

```
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcctacctg acgcttttta tcgcaactct ctactgtttc tccatacccg tttttttggg    300
ctaacaggag gaattaacca tgaccaaggc caccaaggaa cagaaaagcc tggtcaagaa    360
ccgcggtgct gaactggttg tggactgcct cgtggaacag ggcgtgaccc atgtcttcgg    420
catcccgggc gccaagatcg acgccgtctt cgacgccctg caggataaag gtccggaaat    480
catcgtggca cgccatgagc agaacgcagc cttcatggcc caggccgtcg gtcggctgac    540
gggtaagccc ggcgtggtgc tggtcacctc cggtccggga gcctcgaacc tggccacggg    600
actgctcacc gccaacaccg aaggcgaccc ggtggtcgcc ctggccggta atgtcatccg    660
ggcggatcgc ctgaagcgca cccatcagtc cctggataac gcggccctgt tccagccaat    720
caccaaatat agtgtcgaag tgcaggatgt gaagaacatc ccggaagccg tcaccaatgc    780
gttccgaatc gcgtccgccg gccaagcagg ggcagcattc gtgagcttcc cccaggacgt    840
ggtcaatgaa gtgaccaaca ccaaaaacgt cagagccgta gccgccccga agctgggccc    900
tgcagcagat gacgccatct ccgctgccat cgcgaagatc cagaccgcaa agctgccggt    960
```

-continued cgtgctggtc ggaatgaagg gcggacgccc ggaggccatc aaggccgtgc gtaaactgct 1020
gaagaaggtg cagctaccgt tcgtggaaac ctaccaggcc gccggcaccc tgagtcggga 1080
cttggaagac cagtatttcg gccgtatcgg cctgttccgc aaccagccgg gcgacctgct 1140
cctggaacaa gccgatgtgg tgctgaccat cggctacgac ccgatcgaat atgacccgaa 1200
gttctggaac atcaatggcg accgcacgat catccatctg gacgaaatca tcgccgacat 1260
cgaccatgcc tatcagccgg acctggaact gatcggcgac atcccgagca ccatcaacca 1320
catcgaacac gatgccgtga aggtggaatt tgccgaacgc gaacagaaga tcctgtcgga 1380
cctgaagcag tatatgcatg agggcgaaca ggtgcctgcc gactggaagt cggacagagc 1440
ccatccgctg gaaatcgtga aggaactgcg taacgccgtc gacgaccatg tcaccgtcac 1500
ctgcgatatc ggcagccatg ccatttggat gagccgctac ttccggagct atgaaccgct 1560
gaccctgatg atctccaacg gtatgcagac cctcggcgtc gccctcccgt gggccatcgg 1620
cgcaagtctg gtgaagccgg gcgaaaaagt ggtcagcgtg tccggcgacg gcggcttcct 1680
gttctccgct atggaactgg aaaccgcggt ccgcctgaag gccccgatcg tgcatatcgt 1740
gtggaacgac agcacctacg acatggtcgc cttccagcag ctgaaaaagt acaaccgcac 1800
cagcgccgtg gacttcggca atatcgacat cgtgaagtat gccgaatcct tcggagccac 1860
cggactgcgc gtggaatccc cggaccagct ggcggacgtt ctgcgtcagg gcatgaatgc 1920
cgaaggtccc gtgattatcg atgtgcccgt cgactacagc gacaacatca acctggcctc 1980
ggacaaattg ccgaaggagt tcggcgaact gatgaaaaca aaagcactat aaaaaggagg 2040
tacgtatgaa ccactcggcc gaatgcacct gcgaagagag cctctgcgaa accctccggg 2100
ccttctcggc ccagcacccg gagagcgtcc tgtaccagac gagcctgatg tcggcgctgc 2160
tgtcgggcgt gtatgaaggc tcgacgacca tcgccgacct gctgaagcat ggcgacttcg 2220
gcctgggcac cttcaatgaa ctggacggcg agctcatcgc cttcagctcg caggtgtatc 2280
agctccgggc cgatggctcc gcccggaagg cccagcccga acagaagacc ccgttcgccg 2340
tgatgacctg gttccagccg cagtatcgga agaccttcga ccaccccgtg agccgccagc 2400
agctccacga ggtgatcgac cagcagatcc cgagcgacaa cctcttctgc gccctgcgca 2460
tcgacggcca tttccgccac gcgcataccc gcaccgtccc gcggcagacc ccgccctacc 2520
gcgccatgac cgatgtcctg gatgaccagc cggtcttccg gttcaaccag cgcgagggcg 2580
tcctggtcgg cttccgcacc ccgcagcaca tgcagggcat caacgtcgcg ggctatcatg 2640
aacacttcat caccgatgat cgcaagggcg gcggccacct cctcgactac cagctggacc 2700
acggcgtcct gaccttcggc gaaatccata agctgatgat cgacctcccc gccgacagcg 2760
ccttcctgca ggcgaatctg catccggaca acctcgatgc cgccatccgc tccgtcgagt 2820
cgtgaaaagg aggtacgtat gaaagccctg ctgtggcata accagcgcga cgtgcgggtg 2880
gaagaggtcc cggagcccgc cgtccgcagc ggcgcggtga aaatcaaagt gaaatggtgc 2940
ggcatctgtg gcaccgacct gcatgaatat ctggccggcc ccatcttcat cccgacggag 3000
gaacatccgc tgacgcacgt caaggccccg gtcatcctcg gccatgagtt cagcggcgag 3060
gtggtggaga tcggcgaagg cgtcaccaat cacaaagtcg gcgatcgcgt ggtcgtcgaa 3120
ccgatctact cgtgcggcaa gtgtgaggcg tgcaagcacg gccactataa tgtctgcgag 3180
cagctggtgt tccacggcct gggcggcgac ggcggcggct tctcggagta caccgtggtg 3240
ccggcggata tggtccacca catcccggat gaaatgacct acgagcaggg cgccctggtc 3300

```
gagccggccg ccgtggcggt gcacgcggtg cgccagagca aactcaagga gggcgaagcc   3360

gtggccgtct tcggctgcgg cccgatcggc ctgctggtca tccaggcggc caaagcggcg   3420

ggcgcgaccc ccgtcatcgc ggtcgagctg tcgaaggaac gccaggagct cgccaagctg   3480

gcgggcgcgg attatgtcct gaaccccgcc gaacaggacg tggtggcgga aatccggaac   3540

ctgaccaacg gcctgggcgt caacgtctcc ttcgaggtca ccggcgtgga agtcgtcctg   3600

cggcaggcga tcgaatcgac ctcgttcgag ggccagacgg tcatcgtgtc ggtctgggag   3660

aaggacgcca ccatcacgcc caataatctg gtcctgaaag agaaggaagt ggtcggcatc   3720

ctcggctacc ggcatatctt cccgtccgtc atcaagctga tctcgtcggg ccagatccag   3780

gccgagaaac tcatcaccaa gaagatcacg gtggaccagg tggtcgaaga aggcttcgaa   3840

gcgctggtca aggataagaa gcaggtgaag atcctcgtgt cgccgaagtg atttcagcct   3900

gatacagatt aaatcagaac gcagaagcgg tctgataaaa cagaatttgc ctggcggcag   3960

tagcgcggtg gtcccacctg accccatgcc gaactcagaa gtgaaacgcc gtagcgccga   4020

tggtagtgtg gggtctcccc atgcgagagt agggaactgc caggcatcaa ataaaacgaa   4080

aggctcagtc gaaagactgg gcctttcgtt ttatctgttg tttgtcggtg aacgctctcc   4140

tgagtaggac aaatccgccg ggagcggatt tgaacgttgc gaagcaacgg cccggagggt   4200

ggcgggcagg acgcccgcca taaactgcca ggcatcaaat taagcagaag gccatcctga   4260

cggatggcct ttttgcgttt c                                               4281
```

<210> SEQ ID NO 19
<211> LENGTH: 572
<212> TYPE: PRT
<213> ORGANISM: Bacillus licheniformis

<400> SEQUENCE: 19

```
Met Asn Asn Val Ala Ala Lys Asn Glu Thr Leu Thr Val Arg Gly Ala
1               5                   10                  15

Glu Leu Val Val Asp Ser Leu Ile Gln Gln Gly Val Thr His Val Phe
            20                  25                  30

Gly Ile Pro Gly Ala Lys Ile Asp Ala Val Phe Asp Val Leu Lys Asp
        35                  40                  45

Lys Gly Pro Glu Leu Ile Val Cys Arg His Glu Gln Asn Ala Ala Phe
    50                  55                  60

Met Ala Ala Ala Val Gly Arg Leu Thr Gly Lys Pro Gly Val Cys Leu
65                  70                  75                  80

Val Thr Ser Gly Pro Gly Ala Ser Asn Leu Ala Thr Gly Leu Val Thr
                85                  90                  95

Ala Asn Thr Glu Gly Asp Pro Val Val Ala Leu Ala Gly Ala Val Lys
            100                 105                 110

Arg Ala Asp Arg Leu Lys Lys Thr His Gln Ser Met Asp Asn Ala Ala
        115                 120                 125

Leu Phe Gln Pro Ile Thr Lys Tyr Ser Ala Glu Val Glu Asp Ala Asn
    130                 135                 140

Asn Ile Pro Glu Ala Val Thr Asn Ala Phe Arg Ala Ala Ala Ser Gly
145                 150                 155                 160

Gln Ala Gly Ala Ala Phe Leu Ser Phe Pro Gln Asp Val Thr Ala Gly
                165                 170                 175

Pro Ala Thr Ala Lys Pro Val Lys Thr Met Pro Ala Pro Lys Leu Gly
            180                 185                 190

Ala Ala Ser Asp Glu Gln Ile Ser Ala Ala Ile Ala Lys Ile His Asn
```

```
        195                 200                 205

Ala Asn Leu Pro Val Val Leu Val Gly Met Lys Gly Gly Arg Pro Glu
    210                 215                 220

Ala Ile Glu Ala Val Arg Arg Leu Leu Arg Lys Val Lys Leu Pro Phe
225                 230                 235                 240

Val Glu Thr Tyr Gln Ala Ala Gly Thr Leu Ser His Asp Leu Glu Asp
                245                 250                 255

Gln Tyr Phe Gly Arg Ile Gly Leu Phe Arg Asn Gln Pro Gly Asp Met
            260                 265                 270

Leu Leu Glu Lys Ala Asp Val Val Leu Thr Val Gly Tyr Asp Pro Ile
        275                 280                 285

Glu Tyr Asp Pro Val Phe Trp Asn Gly Lys Gly Glu Arg Ser Val Ile
    290                 295                 300

His Leu Asp Glu Ile Gln Ala Asp Ile Asp His Asp Tyr Gln Pro Glu
305                 310                 315                 320

Ile Glu Leu Ile Gly Asp Ile Ala Glu Thr Leu Asn His Ile Glu His
                325                 330                 335

Asp Ser Leu Pro Val Ser Ile Asp Glu Ser Phe Ala Pro Val Leu Asp
            340                 345                 350

Tyr Leu Lys Lys Ala Leu Glu Glu Gln Ser Glu Pro Pro Lys Glu Thr
        355                 360                 365

Lys Thr Asp Leu Val His Pro Leu Gln Ile Val Arg Asp Leu Arg Glu
    370                 375                 380

Leu Leu Ser Asp Asp Ile Thr Val Thr Cys Asp Ile Gly Ser His Ala
385                 390                 395                 400

Ile Trp Met Ser Arg Tyr Phe Arg Thr Tyr Arg Pro His Gly Leu Leu
                405                 410                 415

Ile Ser Asn Gly Met Gln Thr Leu Gly Val Ala Leu Pro Trp Ala Ile
            420                 425                 430

Ala Ala Thr Leu Val Asn Pro Gly Gln Lys Val Val Ser Val Ser Gly
        435                 440                 445

Asp Gly Gly Phe Leu Phe Ser Ala Met Glu Leu Glu Thr Ala Val Arg
    450                 455                 460

Leu Lys Ala Pro Ile Val His Ile Val Trp Asn Asp Ser Thr Tyr Asp
465                 470                 475                 480

Met Val Ala Phe Gln Gln Glu Met Lys Tyr Lys Arg Thr Ser Gly Val
                485                 490                 495

Asp Phe Gly Gly Ile Asp Ile Val Lys Tyr Ala Glu Ser Phe Gly Ala
            500                 505                 510

Lys Gly Leu Arg Val Asn Ser Pro Asp Glu Leu Ala Glu Val Leu Lys
        515                 520                 525

Ala Gly Leu Asp Ala Glu Gly Pro Val Val Ile Asp Ile Pro Val Asp
    530                 535                 540

Tyr Ser Asp Asn Ile His Leu Ala Asp Gln Arg Phe Pro Lys Lys Phe
545                 550                 555                 560

Glu Glu His Phe Asn Lys Glu Ala Ser Lys Gln Ser
                565                 570
```

<210> SEQ ID NO 20
<211> LENGTH: 1719
<212> TYPE: DNA
<213> ORGANISM: Bacillus licheniformis

<400> SEQUENCE: 20

-continued

```
atgaataacg tcgcggccaa gaacgaaacc ctgaccgtcc ggggcgccga actcgtggtg     60
gatagcctga tccagcaggg cgtgacccat gtcttcggca tcccgggcgc caaaatcgac    120
gcggtcttcg acgtgctgaa ggataagggc cccgaactga tcgtctgccg ccatgagcag    180
aacgcggcct tcatggccgc cgccgtcggc cgcctgacgg gcaagccggg cgtctgcctg    240
gtcacctccg gcccgggcgc ctcgaatctc gcgaccggcc tggtcaccgc gaacacggaa    300
ggcgacccgg tggtcgccct ggcgggcgcc gtgaagcggg cggatcggct gaagaagacg    360
caccagtcga tggataacgc cgccctgttc cagcccatca cgaagtacag cgcggaggtg    420
gaagacgcga acaacatccc ggaggccgtg acgaacgcct tccgcgccgc ggcgtccggc    480
caggccggcg cggccttcct cagcttcccc caggatgtca ccgccggccc ggccaccgcc    540
aagccggtca aaaccatgcc cgccccgaag ctgggcgccg cgagcgatga acagatctcc    600
gccgcgatcg cgaagatcca caacgcgaat ctgccggtgg tcctcgtggg catgaagggc    660
ggccggccgg aagccatcga agccgtgcgc cgcctgctcc gcaaggtcaa gctcccgttc    720
gtggaaacct accaggcggc cggcacgctg tcgcacgatc tggaggatca gtacttcggc    780
cggatcggcc tgttccggaa ccagccgggc gacatgctcc tggaaaaggc cgacgtggtc    840
ctgaccgtgg gctacgaccc gatcgagtac gatccggtgt tctggaatgg caaaggcgaa    900
cgctcggtca tccacctcga cgaaatccag gccgatatcg atcacgacta ccagcccgag    960
atcgaactca tcggcgacat cgcggaaacc ctcaatcaca tcgagcatga ctcgctgccg   1020
gtgtccatcg acgaatcctt cgcgcccgtg ctcgactatc tcaagaaggc gctcgaagaa   1080
cagtcggagc cccgaagga aacgaagacc gatctggtcc acccgctcca gatcgtgcgc   1140
gacctgcgcg agctgctctc cgatgacatc accgtcacct gcgacatcgg cagccacgcc   1200
atctggatgt cccgctattt ccgcacctat cgcccgcatg gcctcctgat ctccaacggc   1260
atgcagacgc tgggcgtcgc cctgccgtgg gcgatcgccg cgaccctggt gaacccgggc   1320
cagaaggtgg tgtcggtcag cggcgatggc ggcttcctct tctccgcgat ggaactcgaa   1380
accgccgtcc gcctcaaggc gccgatcgtg cacatcgtgt ggaacgactc cacgtacgac   1440
atggtcgcgt tccagcagga aatgaagtac aagcgcacct ccggcgtcga tttcggcggc   1500
atcgacatcg tcaagtatgc ggaatccttc ggcgccaaag gcctccgcgt gaatagcccc   1560
gatgaactgg ccgaggtcct gaaggccggc ctcgacgcgg agggcccggt ggtcatcgac   1620
atccccgtcg actactcgga taacatccac ctggccgacc agcgcttccc gaagaagttc   1680
gaggagcact tcaacaagga agcgtcgaag cagtcctga                          1719
```